(12) United States Patent
Verhaegh et al.

(10) Patent No.: US 11,649,488 B2
(45) Date of Patent: May 16, 2023

(54) DETERMINATION OF JAK-STAT1/2 PATHWAY ACTIVITY USING UNIQUE COMBINATION OF TARGET GENES

(71) Applicant: InnoSIGN B.V., Eindhoven (NL)

(72) Inventors: Wilhelmus Franciscus Johannes Verhaegh, Heusden gem. Asten (NL); Meng Dou, Eindhoven (NL); Anja Van De Stolpe, Vught (NL); Rick Velter, Eindhoven (NL)

(73) Assignee: InnoSIGN B.V., Eindhoven (NL)

( * ) Notice: Subject to any disclaimer, the term of this patent is extended or adjusted under 35 U.S.C. 154(b) by 1267 days.

(21) Appl. No.: 16/143,885

(22) Filed: Sep. 27, 2018

(65) Prior Publication Data

US 2019/0100795 A1 Apr. 4, 2019

(30) Foreign Application Priority Data

Oct. 2, 2017 (EP) ..................................... 17194291

(51) Int. Cl.
| | |
|---|---|
| *C12Q 1/6886* | (2018.01) |
| *G16B 25/10* | (2019.01) |
| *C12Q 1/6851* | (2018.01) |
| *C12Q 1/6844* | (2018.01) |
| *G16B 5/20* | (2019.01) |
| *G16B 25/00* | (2019.01) |
| *G16B 50/00* | (2019.01) |
| *C12Q 1/6809* | (2018.01) |
| *G06N 7/00* | (2023.01) |

(52) U.S. Cl.
CPC ......... *C12Q 1/6851* (2013.01); *C12Q 1/6809* (2013.01); *C12Q 1/6844* (2013.01); *C12Q 1/6886* (2013.01); *G06N 7/005* (2013.01); *G16B 5/20* (2019.02); *G16B 25/00* (2019.02); *G16B 50/00* (2019.02); *C12Q 2600/158* (2013.01); *G16B 25/10* (2019.02)

(58) Field of Classification Search
CPC .. C12Q 1/6851; C12Q 1/6809; C12Q 1/6844; C12Q 1/6886; G16B 5/20; G16B 25/00; G16B 50/00; G06N 7/005
USPC ......................................................... 702/19
See application file for complete search history.

(56) References Cited

U.S. PATENT DOCUMENTS

| | | | |
|---|---|---|---|
| 5,436,134 A | 7/1995 | Haugland | |
| 5,476,928 A | 12/1995 | Langer | |
| 5,658,751 A | 8/1997 | Haugland | |
| 5,874,219 A | 2/1999 | Fodor | |
| 5,958,691 A | 9/1999 | Biesecker | |
| 6,004,761 A | 12/1999 | Brown | |
| 6,146,897 A | 11/2000 | Bhandare | |
| 6,171,798 B1 | 1/2001 | Gish | |
| 6,225,047 B1 | 5/2001 | Hutchens | |
| 6,308,170 B1 | 10/2001 | Baid | |
| 6,391,550 B1 | 5/2002 | Langer-Safer | |
| 6,675,104 B2 | 1/2004 | Braginsky | |
| 6,713,297 B2 | 3/2004 | Borkholder | |
| 6,720,149 B1 | 4/2004 | Fodor | |
| 6,844,165 B2 | 1/2005 | Hutchens | |
| 6,884,578 B2 | 4/2005 | Mahadevappa | |
| 7,056,674 B2 | 6/2006 | Baker | |
| 7,081,340 B2 | 7/2006 | Baker | |
| 7,160,734 B2 | 1/2007 | Hutchens | |
| 7,208,470 B2 | 4/2007 | Duan | |
| 7,299,134 B2 | 11/2007 | Hutchens | |
| 7,526,637 B2 | 4/2009 | Han | |
| 7,569,345 B2 | 8/2009 | Baker | |
| 7,695,913 B2 | 4/2010 | Baker | |
| 7,723,033 B2 | 5/2010 | Baker | |
| 7,754,431 B2 | 7/2010 | Beck | |
| 7,754,861 B2 | 7/2010 | Boschetti | |
| 7,816,084 B2 | 10/2010 | Beck | |
| 7,838,224 B2 | 11/2010 | Baker | |

(Continued)

FOREIGN PATENT DOCUMENTS

| | | |
|---|---|---|
| JP | 2005176804 A | 7/2005 |
| WO | 2013011479 A2 | 1/2013 |

(Continued)

OTHER PUBLICATIONS

Nancy Au-Yeung, Roli Mandhana & Curt M Horvath (2013) Transcriptional regulation by STAT1 and STAT2 in the interferon JAK-STAT pathway, JAK-STAT, 2:3, e23931, DOI: 10.4161/jkst. 23931 (Year: 2013).*

(Continued)

*Primary Examiner* — G Steven Vanni
*Assistant Examiner* — Guozhen Liu
(74) *Attorney, Agent, or Firm* — Bond, Schoeneck & King, PLLC

(57) ABSTRACT

A bioinformatics process which provides an improved means to detect a JAK-STAT1/2 cellular signaling pathway in a subject, such as a human, based on the expression levels of at least three unique target genes of the JAK-STAT1/2 cellular signaling pathway measured in a sample. The invention includes an apparatus comprising a digital processor configured to perform such a method, a non-transitory storage medium storing instructions that are executable by a digital processing device to perform such a method, and a computer program comprising program code means for causing a digital processing device to perform such a method. Kits are also provided for measuring expression levels of unique sets of JAK-STAT1/2 cellular signaling pathway target genes.

8 Claims, 20 Drawing Sheets

Specification includes a Sequence Listing.

(56) References Cited

U.S. PATENT DOCUMENTS

| | | | |
|---|---|---|---|
| 7,858,304 | B2 | 12/2010 | Baker |
| 7,888,019 | B2 | 2/2011 | Baker |
| 7,919,261 | B2 | 4/2011 | Fantin |
| 7,930,104 | B2 | 4/2011 | Baker |
| 7,939,261 | B2 | 5/2011 | Baker |
| 8,008,003 | B2 | 8/2011 | Baker |
| 8,021,894 | B2 | 9/2011 | Hutchens |
| 8,026,060 | B2 | 9/2011 | Baker |
| 8,029,995 | B2 | 10/2011 | Baker |
| 8,029,997 | B2 | 10/2011 | Kennedy |
| 8,034,565 | B2 | 10/2011 | Baker |
| 8,067,178 | B2 | 11/2011 | Baker |
| 8,071,286 | B2 | 12/2011 | Baker |
| 8,148,076 | B2 | 4/2012 | Baker |
| 8,153,378 | B2 | 4/2012 | Baker |
| 8,153,379 | B2 | 4/2012 | Baker |
| 8,153,380 | B2 | 4/2012 | Baker |
| 8,198,024 | B2 | 6/2012 | Baker |
| 8,206,919 | B2 | 6/2012 | Baker |
| 8,273,537 | B2 | 9/2012 | Baker |
| 8,367,345 | B2 | 2/2013 | Baker |
| 8,451,450 | B2 | 5/2013 | Heng |
| 8,518,639 | B2 | 8/2013 | Rihet |
| 8,541,170 | B2 | 9/2013 | Kennedy |
| 8,632,980 | B2 | 1/2014 | Baker |
| 8,703,736 | B2 | 4/2014 | Han |
| 8,725,426 | B2 | 5/2014 | Cherbavaz |
| 8,741,605 | B2 | 6/2014 | Baker |
| 8,765,383 | B2 | 7/2014 | Collin |
| 8,808,994 | B2 | 8/2014 | Baker |
| 8,868,352 | B2 | 10/2014 | Baker |
| 8,906,625 | B2 | 12/2014 | Baker |
| 8,911,940 | B2 | 12/2014 | Kim |
| 9,076,104 | B2 | 7/2015 | Chang |
| 2013/0042333 | A1 | 2/2013 | Cairo |
| 2014/0342924 | A1 | 11/2014 | Harkin |
| 2015/0232926 | A1 | 8/2015 | Wu |
| 2016/0117439 | A1 | 4/2016 | Brussel |
| 2016/0296480 | A1 | 10/2016 | Frank |
| 2016/0298196 | A1* | 10/2016 | Van Ooijen .......... C12Q 1/6886 |

FOREIGN PATENT DOCUMENTS

| | | |
|---|---|---|
| WO | 2014102668 A2 | 7/2014 |
| WO | 2014174003 A1 | 10/2014 |
| WO | 2015101635 A1 | 7/2015 |
| WO | 2015193212 A1 | 12/2015 |
| WO | 2016062891 A1 | 4/2016 |

OTHER PUBLICATIONS

Sally Thomas, Katherine H. Fisher, John A. Snowden, Sarah J. Danson, Stephen Brown, Martin P. Zeidl: Methotrexate Is a JAK/STAT Pathway Inhibitor. PLoS ONE 10(7): e0130078. doi:10.1371/journal.pone.0130078. Received: Jan. 21, 2015, Accepted: May 15, 2015, Published: Jul. 1, 2015 (Year: 2015).*

Robertson, G., Hirst, M., Bainbridge, M. et al. Genome-wide profiles of STAT1 DNA association using chromatin immunoprecipitation and massively parallel sequencing. Nat Methods 4, 651-657 (2007). https://doi.org/10.1038/nmeth1068 (Year: 2007).*

Platanias, L. Mechanisms of type-I- and type-II-interferon-mediated signaling. Nat Rev Immunol 5, 375-386 (2005). https://doi.org/10.1038/nri1604 (Year: 2005).*

"GeneChip Human Genome Arrays", AFFYMETRIX, 2013.

Liu, Yu-Shu et al "Chemoattraction of Macrophages by Secretory Molecules derived from Cells Expressing the Signal Peptide of Eosinophil Cationic Protein", BMC SYSTEMS BIOLOGY, vol. 6, No. 1, pp. 105, 2012.

Chistiakov, Dimitry A. et al "Immune-Inflammatory Responses in Atherosclerosis: Role of an Adaptive Immunity mainly Driven by T and B Cells", IMMUNOGIOLOGY, vol. 221, No. 9, pp. 1014-1033, 2016.

Bedard, Philippe L. et al Nature Insight: Tumor Heterogeneity, Sep. 19, 2013, vol. 501.

Zellmer, Victoria et al "Evolving concepts of tumor heterogeneity", Cell and Bioscience 2014, 4:69.

Liu, Bin et al ., "Inhibition of Stat1-mediated gene activation by PIAS1", Cell Biology, vol. 95, Sep. 1998, pp. 10626 to 10631.

Platanias, L.C., "Mechanisms of type-I- and type-II-interferon-mediated signaling", Nature Reviews Immunology, vol. 5, May 2015, pp. 375 to 386—Abstract Only.

Verhaegh, W. et al., "Selection of personalized patient therapy through the use of knowledge-based computational models that identify tumor-driving signal transduction pathways", Cancer Research, vol. 74, No. 11, 2014, pp. 2936 to 2945.

Miklossy, Gabriella et al., "Therapeutic modulators of STAT signaling for human diseases", Nature Reviews Drug Discovery, vol. 12, No. 8, Aug. 2013, pp. 611 to 629.

Yue, Peibin et al "Targeting STAT3 in cancer: how successful are we?", Expert Opinion on Investigational Drugs, vol. 18, No. 1, pp. 45 to 56.

Yu, Hus et al , "STATs in cancer inflammation and immunity: a leading role for STAT3", Nature Reviews Cancer, vol. 9, No. 11, Nov. 2009, pp. 798 to 809.

* cited by examiner

SEQUENCE LISTING

<160> NUMBER OF SEQ ID NOS: 23

<210> SEQ ID NO 1
<211> LENGTH: 2535
<212> TYPE: DNA
<213> ORGANISM: Homo sapiens

<400> SEQUENCE: 1

| gagggccga | ggccagcccc | ggagaggaga | aaaccgcgg | gcctggccgg | gtgcaggcca | 60 |
| ccttgccgg | cggatcggaa | tccccgccca | caccgtggtc | tttccagcac | cgcagacacc | 120 |
| tgccggctcc | tcccgagcgg | agctcagggc | tgacaaagcg | cggtcagagc | ggccgcttac | 180 |
| tggggctcgc | ccgctcctta | gagcactggc | aatgatgtgc | ggatcctcgc | tgctgctgct | 240 |
| gggaaactgt | tgagtggctg | aatgacccca | ggggaccctg | ggagagctct | gaagccctca | 300 |
| gccaccaagt | ggctgggctg | gcaagggttc | attcattcat | tcaacaaata | cgaatgtgca | 360 |

```
gcggtgctgg ggtcatgatg gctcggtggg cagcgagggg ccgggccggc tggaggagca    420
cagtgcggat tctgtcgcca ctgggacact gtgaaccagg agtgagtcgg agctgccgcg    480
ctgcccaggc catggactgt gaggtcaaca acggttccag cctcagggat gagtgcatca    540
caaacctact ggtgtttggc ttcctccaaa gctgttctga caacagcttc cgcagagagc    600
tggacgcact gggccacgag ctgccagtgc tggctcccca gtgggagggc tacgatgagc    660
tgcagactga tggcaaccgc agcagccact cccgcttggg aagaatagag gcagattctg    720
aaagtcaaga agacatcatc cggaatattg ccaggcacct cgcccaggtc ggggacagca    780
tggaccgtag catccctccg ggcctggtga acggcctggc cctgcagctc aggaacacca    840
gccggtcgga ggaggaccgg aacagggacc tggccactgc cctggagcag ctgctgcagg    900
cctaccctag agacatggag aaggagaaga ccatgctggt gctggccctg ctgctggcca    960
agaaggtggc cagtcacacg ccgtccttgc tccgtgatgt ctttcacaca acagtgaatt   1020
ttattaacca gaacctacgc acctacgtga ggagcttagc cagaaatggg atggactgaa   1080
cggacagttc cagaagtgtg actggctaaa gctcgatgtg gtcacagctg tatagctgct   1140
tccagtgtag acggagccct ggcatgtcaa cagcgttcct agagaagaca ggctggaaga   1200
tagctgtgac ttctatttta aagacaatgt taaacttata acccacttta aaatatctac   1260
attaatatac ttgaatgaaa atgtccattt cacacgtatt gaatggcctt catatcatcc   1320
acacatgaat ctgcacatct gtaaatctac acacggtgcc tttatttcca ctgtgcaggt   1380
tcccacttaa aaattaaatt ggaaagcagg tttcaaggaa gtagaaacaa aatacaattt   1440
ttttggtaaa aaaaaattac tgtttattaa agtacaacca tagaggatgg tcttacagca   1500
ggcagtatcc tgtttgagga aagcaagaat cagagaagga acatacccct tacaaatgaa   1560
aaattccact caaaataggg actatctatc ttaatactaa ggaaccaaca atcttcctgt   1620
ttaaaaaacc acatggcaca gagattctga actaaagtgc tgcactcaaa tgatgggaag   1680
tccggcccca gtacacaggg gcttgacttt ttcaacttcg tttcctttgt tggagtcaaa   1740
aagaaccact tgtggttcta aaaggtgtga aggtgattta agggcccagg tcagccactg   1800
tttgtttaca aaatcaggta actaactgca tacactttt ctctttccat gacatcaaga   1860
ctttgctaaa gacatgaagc cacgggtgcc agaagctact gcgatgcccc gggagttagc   1920
cccctggtaa tagctgtaaa cttccaattt ctagccatac gctcagctca tccatgcctc   1980
agaagtgcat ctggagagaa caggtttcta agcataaaag atgaaagagc agttggactt   2040
tttaaaaatt cagcaaagtg gttccctctc ttagggacag tcaaaaccaa gtcacttagg   2100
tagtaccaaa ataaataagg aaaagcttag ctttagaaac agtgcaacac tggtctgctg   2160
ttccagtggt aagctatgtc ccaggaatca gtttaaaagc acgacagtgg atgctgggtc   2220
catatcacac acattgctgt gaacaggaaa ctcctgtgac cacaacatga ggccactgga   2280
gacgcatatg agtaagggca ctgacggact catgatttct tcttaccaga tgcttttcctg   2340 ttctttaaga gtttaaaatc atcagaaagg aaaaacaaac tctatattgt tcagcatgca   2400
atacatacca cgctagggct ggctcaattg aaagtgggca aaagcttaca aatactaaaa   2460
agaagtgctg ccgcgcagtg tggaggccac tgtttggaaa taaatcttcc taacactaca   2520
aaaaaaaaaa aaaaa                                                    2535

<210> SEQ ID NO 2
<211> LENGTH: 3362
<212> TYPE: DNA
```

<213> ORGANISM: Homo sapiens

<400> SEQUENCE: 2

```
ggactggcgg cgggcggcgg gcggcgggcg gcgcgggagg gcgggcggag ggaaccaggc    60
cggccggagc gtgtgcgccg cccgcggtcc ggtcacgtcc ccgcgtgggc gccgctgccc   120
gcgtcgtacg gaacgagggc gccgcggccc cgtgctcgcc gccccgcccc gccccgccct   180
gcccggagca gctcggcaga tgctctgtgc tgcggcccgg aggtgaaggg ctggatgcac   240
agtgggagcc ggaggcgggg ggctgcaggg agcacaccag cgaccggccc tccaaccctc   300
cagccactca gcaacatcgc cacagcaacc agcaaccaga cggcagcagc cgaggcaaac   360
acaagcggac ggcttccac cgtcgccgag gacagggaat gactacggca aatcaggcca    420
ctttgccaac tagggaggtg gagtgtcact agtggggagg ggcggccacc gcccgctgca   480
cagagcgcca tgccggctgg agaagaggcg ctggggcagg ggctgcagtg tggctcggcc   540
tcacccccct gctggcactg agtgcctcca gggcagctgg gctcttgtct gcctggtctc   600
agtgtcccct gtgcaagag ggagaggtgc cccatcccgt gctccttgtc tgggcccgct    660
gctgccagac catgggatgt cggcaaagct cagaggaaaa agaagcagcc cggcggtccc   720
ggagaattga ccgccacctg cgctcagaga gccagcggac acgccgcgaa atcaagctgc   780
tcctgctggg caccagcaac tcaggcaaga gcaccatcgt caaacagatg aagatcatcc   840
acagcggcg cttcaacctg gaggcctgca aggagtacaa gccctcatc atctacaatg     900
ccatcgactc gctgacccgc atcatccggg ccctggccgc cctcaggatc gacttccaca   960
accccgaccg cgcctacgac gctgtgcagc tctttgcgct gacgggcccc gctgagagca  1020
agggcgagat cacacccgag ctgctgggtg tcatgcgacg gctctgggcc gacccagggg  1080
cacaggcctg cttcagccgc tccagcgagt accacctgga ggacaacgcg gcctactacc  1140
tgaacgacct ggagcgcatc gccgcagctg actatatccc cactgtcgag gacatcctgc  1200
gctcccggga catgaccacg ggcattgtgg agaacaagtt caccttcaag gagctcacct  1260
tcaagatggt ggacgtgggg gggcagaggt cagagcgcaa aaagtggatc cactgcttcg  1320
agggcgtcac agccatcatc ttctgtgtgg agctcagcgg ctacgacctg aaactctacg  1380
aggataacca gacaagtcgg atggcagaga gcttgcgcct ctttgactcc atctgcaaca  1440
acaactggtt catcaacacc tcactcatcc tcttcctgaa caagaaggac ctgctggcag  1500
agaagatccg ccgcatcccg ctcaccatct gctttcccga gtacaagggc cagaacacgt  1560
acgaggaggc cgctgtctac atccagcggc agtttgaaga cctgaaccgc aacaaggaga  1620
ccaaggagat ctactcccac ttcacctgcg ccaccgacac cagtaacatc cagtttgtct  1680
tcgacgcggt gacagacgtc atcatacaga acaatctcaa gtacattggc ctttgctgag  1740
gagctgggcc cggggcccgc ctgcctatgg tgaaacccac ggggtgtcat gccccaacgc  1800
gtgctagaga ggcccaatcc aggggcagaa acaggggc ctaaagaatg tcccccaccc    1860
cttggcctct gcctccttgg ccccacattt ctgcaaacat aaatatttac ggatagattg  1920
ctaggtagat agacacacac acatgcacac acacacatct ggagatggca aaatcctcta  1980
aaatgtcgag gtctcttgaa gacttgagaa gctgtcacaa ggtcactaca agcccaacct  2040
gccccttcac tttgccttcc tgagttggcc ccactccact tgggggtctg cattggattg  2100
ttagggatag gcagcagggc tgaggcaagg taggccaact gcacccctgt cgcctggagg  2160
agggccagct cgctgcccga gctctggcct agggaccttg ccgctgacca agagggagga  2220
ccagtgcagg gtctgtgcac cttccctgct ggcctgcaca cagctgctca gcaccacttt  2280
```

```
cattctggac ctgggacctt aggagccggg tgacagcact aaccagacct ccagccactc    2340
acagctcttt ttaaaaaaca gcttcaaaat atgcagcaaa aaccaataca acaaaacgag    2400
tggcacgatt tatttcaaac taggccagct gggattccag cttttcttct actagtctga    2460
tgttttataa atcaaaacct ggttttcctt ctctgacatt ttttttttgt tttgtttttt    2520 ggttttttt tttttttggc caaatctcgt ggtgtttcgc agaaaaaaat ccagaaaatt    2580
tcaaatgcag ttgagtattc tttttaaat gcagattttc aaaacatatt ttttttcagg    2640
tggtcttttt tgtgtctggc ttgctgagtg taaaagttgt tatctggacg atctgtctct    2700
ctgctccaaa gaaattttgg agtgagtggc agtcctgcgc cagcctcgcg ggacacgtgt    2760
tgtacataag cctctgcagt gtcctcttgt taatggtggg gttttctgct ttgtttttat    2820
ttaagaaaat aaacacgaca tatttaaaga aggttctttc acctgggagc aaatgaacaa    2880
tagctaagtg tcttggtatt taaagagtaa attatttgtg gctttgctga gtgaaggaag    2940
gggagcaagg ggtggtgccc ctggtccag catgccccgc gcctgagact ggctggaaat    3000
gctctgactc ctgtgaaggc acagccagcg ttgtggcctg agggaggccc tgctgggacc    3060
ctgatctggg ccttcctgtc ccagggccta tgggcaactg cgttgaaagg acgttcgcca    3120
agggccgtgt gtaaatacga actgcgccat ggagaggaga ggcactgccg gagcccttgc    3180
cagatctccc tccctctctc cgtgcagtag ctgtgtgtcc gaggtcagtg tgcggaatca    3240
cagccaagga cgtgaagaga tgtacggggg aagagaagc tggggattgg atgaaagtca    3300
aaggttgtct actttaagaa aataaaatac cctgaatgga gcccaaaaaa aaaaaaaaa    3360 aa                                                                  3362
```

<210> SEQ ID NO 3
<211> LENGTH: 3567
<212> TYPE: DNA
<213> ORGANISM: Homo sapiens

<400> SEQUENCE: 3

```
agagctcgcc actccttagt cgaggcaaga cgtgcgcccg agcccgccg aaccgaggcc     60 acccggagcc gtgcccagtc cacgccggcc gtgcccggcg gccttaagaa cccggcaacc    120
tctgccttct tccctcttcc actcggagtc gcgctccgcg cgccctcact gcagccctg    180 cgtcgccggg accctcgcgc gcgaccgccg aatcgctcct gcagcagagc caacatgccc    240
atcactcgga tgcgcatgag accctggcta gagatgcaga ttaattccaa ccaaatcccg    300
gggctcatct ggattaataa agaggagatg atcttccaga tcccatggaa gcatgctgcc    360
aagcatggct gggacatcaa caaggatgcc tgtttgttcc ggagctgggc cattcacaca    420
ggccgataca aagcagggga aaaggagcca gatcccaaga cgtggaaggc caactttcgc    480
tgtgccatga actccctgcc agatatcgag gaggtgaaag accagagcag gaacaagggc    540
agctcagctg tgcgagtgta ccggatgctt ccacctctca ccaagaacca gagaaaagaa    600
agaaagtcga agtccagccg agatgctaag agcaaggcca gaggaagtc atgtggggat    660 tccagccctg taccttctc tgatggactc agcagctcca ctctgcctga tgaccacagc    720
agctacacag ttccaggcta catgcaggac ttggaggtgg agcaggccct gactccagca    780
ctgtcgccat gtgctgtcag cagcactctc cccgactggc acatcccagt ggaagttgtg    840
ccggacagca ccagtgatct gtacaacttc caggtgtcac ccatgccctc cacctctgaa    900
gctacaacag atgaggatga ggaagggaaa ttacctgagg acatcatgaa gctcttggag    960
```

-continued

```
cagtcggagt ggcagccaac aaacgtggat gggaaggggt acctactcaa tgaacctgga      1020
gtccagccca cctctgtcta tggagacttt agctgtaagg aggagccaga aattgacagc      1080
ccagggggg  atattgggct gagtctacag cgtgtcttca cagatctgaa gaacatggat      1140
gccacctggc tggacagcct gctgacccca gtccggttgc cctccatcca ggccattccc      1200
tgtgcaccgt agcagggccc ctgggcccct cttattcctc taggcaagca ggacctggca      1260
tcatggtgga tatggtgcag agaagctgga cttctgtggg cccctcaaca gccaagtgtg      1320
accccactgc caagtgggga tggggcctcc ctccttgggt cattgacctc tcagggcctg      1380
gcaggccagt gtctgggttt tcttgtggt gtaaagctgg ccctgcctcc tgggaagatg       1440
aggttctgag accagtgtat caggtcaggg acttggacag gagtcagtgt ctggcttttt      1500
cctctgagcc cagctgcctg gagagggtct cgctgtcact ggctggctcc taggggaaca      1560
gaccagtgac cccagaaaag cataacacca atcccagggc tggctctgca ctaagagaaa      1620
attgcactaa atgaatctcg ttcccaaaga actacccct tttcagctga gccctgggga       1680
ctgttccaaa gccagtgaaa tgtgaaggaa agtggggtcc ttcggggcga tgctccctca      1740
gcctcagagg agctctaccc tgctccctgc tttggctgag gggcttggga aaaaaacttg      1800
gcacttttc gtgtggatct tgccacattt ctgatcagag gtgtacacta acatttcccc       1860
cgagctcttg gcctttgcat ttatttatac agtgccttgc tcggcgccca ccaccccctc      1920
aagcccagc agccctcaac aggcccaggg agggaagtgt gagcgccttg gtatgactta       1980
aaattggaaa tgtcatctaa ccattaagtc atgtgtgaac acataaggac gtgtgtaaat      2040
atgtacattt gtcttttat aaaaagtaaa ttgtttataa ggggtgtggc cttttagag       2100
agaaatttaa cttgtagatg atttactttt ttatggaaac actgatggac ttattattgg     2160
catcccgcct gaacttgact ttggggtgaa cagggacatg catctattat aaaatccttt     2220
cggccaggcg cggtggctca cacctgtaat cccagcactt tgggaggccg agatgggtgg     2280
atcacctgag gtcaggagtt cgagaccagc ctggtgaaac tccatttcta ctaaaaatgc     2340
aaaaattagc tgggcgtggt tgcgggtgct tgtaatccca gctactcagg aggctgaggc     2400
aagagaatcg cttgaacctg ggaggtggag gttgcagtga gccgagaaca tgccattgca     2460
ctccagcccg ggcaccaaaa aaaaaaaaa aaaaaaaac ctttcatttg gccgggcatg       2520
gtggcttatg cctgtaatcc tggcactttg ggaggccaag gtgggcagat cacctgaggt     2580
caggagtttg agaccagcct ggccaacatg gtgaaacctc atctctacta aaaatacaaa     2640
aattaggccg ggcacggtgg ctcacgcctg taatcccagc actttgggag gcagaggcgg     2700
gcggatcacg aggtcaggag atcaagacca tcctggctaa cacggtgaaa ccccgtctct     2760
actaaaaata taaaaaatta gccgggccta gtggcgggtg cctgtagtcc cagctactcg     2820
ggaggctgag gcaggagaat ggcatgaacc ccggaggcag agcttgcagt gagccgagat     2880
tgcaccactg cactcagcc tgggcgacag agcgagactc cgtctcaaaa aaaaaaaaa       2940
aaattagccg ggcctggtgg cgggcgcctg taatcccagc tactgtggag gctgaagcac     3000
aagaatcact tgaacccggg agatggaggt tgcagtgagc tgagactgtg ccactgcact     3060
ccagcctggg tgacaagagt gagactttgt ctcaaaaaaa aaaaaatcct tttgtttatg     3120
ttcacataga caatggcaga aggaggggac attcctgtca taggaacatg cttatataaa     3180
catagtcacc tgtccttgac tatcaccagg gctgtcagtt gattctgggc tcctggggcc     3240
caaggagtgt taagttttga ggcatgtgcc ataggtgatg tgtcctgcta acacacagat     3300
gctgctccaa aaagtcagtt gatatgacac agtcacagac agaacagtca gcagcccaag     3360
```

```
aaaggtcctc acggctgctg tgctgggtag cacttgccat ccagtttcta gagtgatgaa    3420
atgctctgtc tgtaccgttc aatacagtag gcactgcac tagccacatg tgccagctaa     3480
gcacttgaaa tgtggccagt gcaataagga attgaactt taattgcatt taataaactg     3540
tatgtaaata gtcaaaaaaa aaaaaaa                                         3567

<210> SEQ ID NO 4
<211> LENGTH: 1972
<212> TYPE: DNA
<213> ORGANISM: Homo sapiens

<400> SEQUENCE: 4
gaaactcccg cctggccacc ataaaagcgc cggccctccg cttccccgcg agacgaaact       60
tcccgtcccg gcggctctgg cacccagggt ccggcctgcg ccttcccgcc aggcctggac      120
actggttcaa cacctgtgac ttcatgtgtg cgcgccggcc acacctgcag tcacacctgt      180 agcccctct gccaagagat ccataccgag gcagcgtcgg tggctacaag ccctcagtcc       240
acacctgtgg acacctgtga cacctggcca cacgacctgt ggccgcggcc tggcgtctgc     300
tgcgacagga gcccttacct ccctgttat aacacctgac cgccacctaa ctgcccctgc      360
agaaggagca atggccttgg ctcctgagag ggcagcccca cgcgtgctgt cggagagtg       420 gctccttgga gagatcagca gcggctgcta tgaggggctg cagtggctgg acgaggcccg     480
cacctgtttc cgcgtgccct ggaagcactt cgcgcgcaag gacctgagcg aggccgacgc     540
gcgcatcttc aaggcctggg ctgtggcccg cggcaggtgg ccgcctagca gcaggggagg     600
tggcccgccc cccgaggctg agactgcgga gcgcgccggc tggaaaacca acttccgctg     660
cgcactgcgc agcacgcgtc gcttcgtgat gctgcgggat aactcggggg acccggccga    720
cccgcacaag gtgtacgcgc tcagccggga gctgtgctgg cgagaaggcc caggcacgga    780
ccagactgag gcagaggccc ccgcagctgt cccaccacca cagggtgggc cccagggcc      840 attcctggca cacacacatg ctggactcca agccccaggc cccctccctg ccccagctgg    900
tgacaagggg gacctcctgc tccaggcagt gcaacagagc tgcctggcag accatctgct    960
gacagcgtca tggggggcag atccagtccc aaccaaggct cctggagagg gacaagaagg   1020
gcttcccctg actggggcct gtgctggagg cccagggctc cctgctgggg agctgtacgg   1080
gtgggcagta gagacgaccc ccagccccgg gccccagccc gcggcactaa cgacaggcga   1140
ggccgcggcc ccagagtccc cgcaccaggc agagccgtac ctgtcaccct cccaagcgc    1200 ctgcaccgcg gtgcaagagc ccagcccagg ggcgctggac gtgaccatca tgtacaaggg   1260
ccgcacggtg ctgcagaagg tggtgggaca cccgagctgc acgttcctat acggcccccc   1320
agacccagct gtccgggcca cagacccca gcaggtagca ttccccagcc ctgccgagct   1380
cccggaccag aagcagctgc gctacacgga ggaactgctg cggcacgtgg ccctgggtt    1440 gcacctggag cttcggggc cacagctgtg ggccgcgc atgggcaagt gcaaggtgta      1500
ctgggaggtg ggcggacccc caggctccgc cagcccctcc accccagcct gctgctgcc    1560 tcggaactgt gacaccccca tcttcgactt cagagtcttc ttccaagagc tggtggaatt   1620
ccgggcacgg cagcgccgtg gctccccacg ctataccatc tacctgggct cgggcagga   1680 cctgtcagct gggaggccca aggagaagag cctggtcctg gtgaagctgg aaccctggct   1740
gtgccgagtg cacctagagg gcacgcagcg tgagggtgtg tcttccctgg atagcagcag   1800
cctcagcctc tgcctgtcca gcgccaacag cctctatgac gacatcgagt gcttccttat   1860
```

| | |
|---|---|
| ggagctggag cagcccgcct agaacccagt ctaatgagaa ctccagaaag ctggagcagc | 1920 |
| ccacctagag ctggccgcgg ccgcccagtc taataaaaag aactccagaa ca | 1972 |

<210> SEQ ID NO 5
<211> LENGTH: 2678
<212> TYPE: DNA
<213> ORGANISM: Homo sapiens

<400> SEQUENCE: 5

| | |
|---|---|
| agcgcggcag caagcgtggg aacgcgggcg gcgagacggc ggcaggacgg cggcaggatg | 60 |
| tgtgaccgga atggtggtcg gcggcttcga cagtggctga tcgagcagat tgacagtagc | 120 |
| atgtatccag gactgatttg ggagaatgag gagaagagca tgttccggat cccttggaaa | 180 |
| cacgctggca agcaagatta taatcaggaa gtggatgcct ccattttaa ggcctgggca | 240 |
| gttttaaag ggaagtttaa agaaggggac aaagctgaac cagccacttg gaagacgagg | 300 |
| ttacgctgtg ctttgaataa gagcccagat tttgaggaag tgacggaccg gtcccaactg | 360 |
| gacatttccg agccatacaa agtttaccga attgttcctg aggaagagca aaaatgcaaa | 420 |
| ctaggcgtgg caactgctgg ctgcgtgaat gaagttacag agatggagtg cggtcgctct | 480 |
| gaaatcgacag agctgatcaa ggagccttct gtggacgatt acatggggat gatcaaaagg | 540 |
| agcccttccc cgccggaggc ctgtcggagt cagctccttc cagactggtg ggcgcagcag | 600 |
| cccagcacag gcgtgccgct ggtgacgggg tacaccacct acgacgcgca ccattcagca | 660 |
| ttctcccaga tggtgatcag cttctactat gggggcaagc tggtgggcca ggccaccacc | 720 |
| acctgccccg agggctgccg cctgtccctg agccagcctg gctgcccgg caccaagctg | 780 |
| tatgggcccg agggcctgga gctggtgcgc ttcccgccgg ccgacgccat ccccagcgag | 840 |
| cgacagaggc aggtgacgcg gaagctgttc gggcacctgg agcgcgggt gctgctgcac | 900 |
| agcagccggc agggcgtgtt cgtcaagcgg ctgtgccagg gccgcgtgtt ctgcagcggc | 960 |
| aacgccgtgg tgtgcaaagg caggcccaac aagctggagc gtgatgaggt ggtccaggtc | 1020 |
| ttcgacacca gccagttctt ccgagagctg cagcagttct ataacagcca gggccggctt | 1080 |
| cctgacggca gggtggtgct gtgctttggg gaagagtttc cggatatggc cccttgcgc | 1140 |
| tccaaactca ttctcgtgca gattgagcag ctgtatgtcc ggcaactggc agaagaggct | 1200 |
| gggaagagct gtggagccgg ctctgtgatg caggcccccg aggagccgcc gccagaccag | 1260 |
| gtcttccgga tgtttccaga tatttgtgcc tcacaccaga gatcattttt cagagaaaac | 1320 |
| caacagatca ccgtctaagt gcgtcgcttg ggcgccccac ccgtctgcg tcctgcatcc | 1380 |
| atctccctgt tacagtggcc cgcatcatga ttaaagaatg tggatccctc tgtctggggt | 1440 |
| gggatgcctt actttgcact taatttaata agggcattct cggaggagta acgtttaat | 1500 |
| acgaagtggc ggcatagccc tgccgagatg tcggtgatgg cctggatgct gtaaccacaa | 1560 |
| cctgtggcta aaaatttat tttctatcct ttacccgtca ttatcattag ttgctatgat | 1620 |
| tctttctgca ttttcggtta actatcattt ccaaagactt gtcattcagt aatattagca | 1680 |
| gatagctgct tcgataaagg aatttggagt ttaaaaatca acttgtgaaa acaaggttgt | 1740 |
| ttttgtcttt atcgtttgtt agagttatag atttatgatt tcataggctt gattctatgt | 1800 |
| gaaatatctt tttacttta tgcattttaa taagatttaa aaatatttag attaaagccc | 1860 |
| cctttaatga gtacaagaaa aactcttggc ttgttagaag aaagtatatt ctttctagaa | 1920 |
| tttggtgcag gaatatgtgt tcatatccag gcaaacgggt gtgttttat cttcagacaa | 1980 |
| tgaaaccttc tcctctgggg ctttgttgcc aggaagatta gaactaaatt tattttttc | 2040 |

```
atttctgtca tgaaatcatt ccagatacct cttttcttct ttccaaatgg ttttcacatg    2100
tgtttgaaat atttgtactt cgaattgtcg gattttccat gtcctccttt ctcctttgtg    2160
cccagcctga gtcagcacca atcccgcatt cagaacctcc cagtgaaagg gcagccttca    2220
ttttgagaag gtggaaggtg ttagggtttg ggagacagct catccaatct cccaagtctc    2280
atggtggatt tgtgactgtg agagtttccg gtttaaaatc tgaaaagcca gatatgcctg    2340 tttcctttc ccagcaccat gcctgtggag gggacagtca gacccagagg tcctttacgt    2400
gtggatggag ttcacaggcg aatagaggag aggaccaggg gacgtggctt gtccctttg    2460 tccaacaaag cattatattt ttaagaatgg cagacctgtt tgctgaagtg ttcataagat    2520
aacaataggc ttgaatctcc aattcaaatg aatgtcaaag cacatatctt taatatgctg    2580
aatgaatatt tattttgta tccattaaaa cagtatattg atctctttta ttctttatta    2640
aaataaaatg ctctttttta aaaaaaaaaa aaaaaaa                              2678

<210> SEQ ID NO 6
<211> LENGTH: 1699
<212> TYPE: DNA
<213> ORGANISM: Homo sapiens

<400> SEQUENCE: 6
ggccctccct ggaggagaac tgaaacttag ggtggggact gtagaaaggg gcggagagat      60
cagccgccca gccaggagtt aagctgaggt cgtctgagcc ctgcgacagc ctggacagca     120
actcaggatg gcatcaggca gggcacgctg caccccgaaaa ctccggaact gggtggtgga    180
gcaagtggag agtgggcagt ttcccggagt gtgctgggat gatacagcta agaccatgtt    240
ccggattccc tggaaacatg caggcaagca ggacttccgg gaggaccagg atgctgcctt    300
cttcaaggcc tgggcaatat ttaagggaaa gtataaggag ggggacacag gaggtccagc    360
tgtctggaag actcgcctgc gctgtgcact caacaagagt tctgaattta aggaggttcc    420
tgagaggggc cgcatggatg ttgctgagcc ctacaaggtg tatcagttgc tgccaccagg    480
aatcgtctct ggccagccag ggactcagaa agtaccatca aagcgacagc acagttctgt    540
gtcctctgag aggaaggagg aagaggatgc catgcagaac tgcacactca gtccctctgt    600
gctccaggac tccctcaata atgaggagga ggggccagt gggggagcag tccattcaga    660
cattgggagc agcagcagca gcagcagccc tgagccacag gaagttacag acacaactga    720 ggccccttt caaggggatc agaggtccct ggagtttctg cttcctccag agccagacta    780
ctcactgctg ctcaccttca tctacaacgg gcgcgtggtg ggcgaggccc aggtgcaaag    840
cctggattgc cgccttgtgg ctgagccctc aggctctgag agcagcatgg agcaggtgct    900
gttccccaag cctggcccac tggagcccac gcagcgcctg ctgagccagc ttgagagggg    960
catcctagtg gccagcaacc cccgaggcct cttcgtgcag cgcctttgcc ccatccccat   1020
ctcctggaat gcaccccagg ctccacctgg gccaggcccg catctgctgc cagcaacga    1080 gtgcgtggag ctcttcagaa ccgcctactt ctgcagagac ttggtcaggt actttcaggg    1140
cctgggcccc ccaccgaagt tccaggtaac actgaatttc tgggaagaga gccatggctc    1200
cagccatact ccacagaatc ttatcacagt gaagatggag caggcctttg cccgatactt   1260
gctggagcag actccagagc agcaggcagc cattctgtcc ctggtgtaga gctgggggga    1320
cccatcttcc acctcacctc tttgttcttc ctgtctcctt tgaagtagac tcattcttca    1380
cacgattgac ctgtcctctt tgtgataatt ctcagtagtt gtccgtgata atcgtgtcct   1440
```

| | |
|---|---|
| gaaaatcctc gcacacactg gctggtggag aactcaaggc taatttttta tccttttttt | 1500 |
| tttttaattt tgagatatac gccctctttc atctgtaagg gactaggaaa ttccaaatgg | 1560 |
| tgtgaaccca gggggccttt ccctcttccc tgacctccca actctaaagc caagcacttt | 1620 |
| atattttcct cttagatatt cactaaggac ttaaaataaa attttattga agaggaaaa | 1680 |
| aaaaaaaaaa aaaaaaaa | 1699 |

<210> SEQ ID NO 7
<211> LENGTH: 586
<212> TYPE: DNA
<213> ORGANISM: Homo sapiens

<400> SEQUENCE: 7

| | |
|---|---|
| agttaaaagg gtgggagcgt ccggggggccc atctctctcg ggtggagtct tctgacagct | 60 |
| ggtgcgcctg cccgggaaca tcctcctgga ctcaatcatg gcttgtggtc tggtcgccag | 120 |
| caacctgaat ctcaaacctg agagtgcctc tcgagtgcga ggcgaggtgg ctcctgacgc | 180 |
| taagagcttc gtgctgaacc tgggcaaaga cagcaacaac ctgtgcctgc acttcaaccc | 240 |
| tcgcttcaac gcccacggcg acgccaacac catcgtgtgc aacagcaagg acggcggggc | 300 |
| ctgggggacc gagcagcggg aggctgtctt tcccttccag cctggaagtg ttgcagaggt | 360 |
| gtgcatcacc ttcgaccagg ccaacctgac cgtcaagctg ccagatggat acgaattcaa | 420 |
| gttccccaac cgcctcaacc tggaggccat caactacatg gcagctgacg tgacttcaa | 480 |
| gatcaaatgt gtggcctttg actgaaatca gccagcccat ggcccccaat aaaggcagct | 540 |
| gcctctgctc cctctgaaaa aaaaaaaaa aaaaaaaaa aaaaa | 586 |

<210> SEQ ID NO 8
<211> LENGTH: 1401
<212> TYPE: DNA
<213> ORGANISM: Homo sapiens

<400> SEQUENCE: 8

| | |
|---|---|
| ggaggaggag cctctgccag actggagaga agcaggcctg agcctcccca aaggcagctc | 60 |
| ctggggactc ccaggaccac aggctgagac gagacgcagg gtggctggag gaagtgagag | 120 |
| gtgaactcag cctgggactg gctgggcgag actctccacc tgctccctgg gaccatcgcc | 180 |
| caccatggct gtggcccagc agctgcgggc cgagagtgac tttgaacagc ttccggatga | 240 |
| tgttgccatc tcggccaaca ttgctgacat cgaggagaag agaggcttca ccagccactt | 300 |
| tgttttcgtc atcgaggtga agacaaaagg aggatccaag tacctcatct accgccgcta | 360 |
| ccgccagttc catgctttgc agagcaagct ggaggagcgc ttcgggccag acagcaagag | 420 |
| cagtgccctg gcctgtaccc tgcccacact cccagccaaa gtctacgtgg gtgtgaaaca | 480 |
| ggagatcgcc gagatgcgga tacctgccct caacgcctac atgaagagcc tgctcagcct | 540 |
| gccggtctgg gtgctgatgg atgaggacgt ccggatcttc ttttaccagt cgccctatga | 600 |
| ctcagagcag gtgccccagg cactccgccg gctccgcccg cgcacccgga agtcaagag | 660 |
| cgtgtcccca cagggcaaca gcgttgaccg catggcagct ccgagagcag aggctctatt | 720 |
| tgacttcact ggaaacagca aactggagct gaatttcaaa gctggagatg tgatcttcct | 780 |
| cctcagtcgg atcaacaaag actggctgga gggcactgtc cggggagcca cgggcatctt | 840 |
| ccctctctcc ttcgtgaaga tcctcaaaga cttccctgag gaggacgacc ccaccaactg | 900 |
| gctgcgttgc tactactacg aagacaccat cagcaccatc aaggacatcg cggtggagga | 960 |
| agatctcagc agcactcccc tattgaaaga cctgctggag ctcacaaggc gggagttcca | 1020 |

-continued

| | |
|---|---|
| gagagaggac atagctctga attaccggga cgctgagggg gatctggttc ggctgctgtc | 1080 |
| ggatgaggac gtagcgctca tggtgcggca ggctcgtggc ctcccctccc agaagcgcct | 1140 |
| cttcccctgg aagctgcaca tcacgcagaa ggacaactac agggtctaca acacgatgcc | 1200 |
| atgagctgac ggtgtccctg gagcagtgag gggacaccag caaaaacctt cagctctcag | 1260 |
| aggagattgg gaccaggaaa acctgggagg atgggcagac ttcctgtctt tgaggctaat | 1320 |
| ggacccgtgg ggcttgtaat ctgtctcttt ctactattta catctgattt aaataaacca | 1380 |
| ttccatctga aagggcaaa a | 1401 |

<210> SEQ ID NO 9
<211> LENGTH: 5620
<212> TYPE: DNA
<213> ORGANISM: Homo sapiens

<400> SEQUENCE: 9

| | |
|---|---|
| gtgaactaaa gagtcgccgc agacaagcag gcccccagat ggagaaccag cctgtgaggt | 60 |
| ggcgggccct gccaggcctc ccacgccctc ctgggctccc cgcagccccc tggctcctcc | 120 |
| ttggcgtgct gctgctgccc gggaccctgc gactggcagg aggacagtca gtgacccaca | 180 |
| ccggcctgcc catcatggcc tccctggcca acacagctat ctccttcagc tgcaggatca | 240 |
| cctatccata cactcccaa ttcaaggttt tcacagtcag ctactttcat gaagatctcc | 300 |
| agggacagag gagccctaag aagccaacaa actgccaccc tggactgggc acagagaacc | 360 |
| agagccacac cctggactgc caggtcaccc ttgtgctgcc gggagcatcg gccactggca | 420 |
| cctactactg ctctgtccac tggccacact ccacggtgag aggcagcggc accttcatcc | 480 |
| tggtcagaga cgcagggtac cgagagcccc cgcagagtcc acagaagctc ctgctctttg | 540 |
| gcttcaccgg cctcctgagt gtcctgagtg tagtgggcac ggccctgctg ctctggaaca | 600 |
| agaagcggat gcggggtcca gggaaggacc ccaccaggaa gtgccagat ccaagatctg | 660 |
| ccagcagccc caagcagcat ccttcagaat ctgtctacac agctctgcag cgccgcgaga | 720 |
| ccgaggtcta tgcctgcatc gagaatgagg atggcagctc acccaccgcc aagcagagcc | 780 |
| ccctctccca ggagagaccg catagattcg aagatgatgg cgaacttaac ctggtctatg | 840 |
| aaaatctcta ggatgggctc caccgctcat agagcttgcc ctgggtcaga ggaccggggc | 900 |
| agcccctgcc accaaaggac ttgatctgag ttgggagtaa ggccccccagg gacacccccat | 960 |
| catttcaccc tcacattcaa ggcccttcct gtcttggccg gcccactgc cccccattc | 1020 |
| tatgccccaa ccaccaaggc tttcccatct tggggccttt gcccaggctg ttccttctgc | 1080 |
| caggcaggcc cttcctcccct tggcccaacc agcaaagcgc ccctcagtct tcaagggctt | 1140 |
| tcctggatgc caccccttgcc cagagccctg ctcactgcct catgctgaca gagcagcatg | 1200 |
| ctctcttggc accagcctgc acctcagcca gtagggcagc ctctgagctg agggaggacc | 1260 |
| ctgcaggggc gcctagcagt gctgtgtggg gagccgaggt atggaggagc tggggagcag | 1320 |
| ctatgcaaat ccctacctac ccagctgggc cagaggcacg aggcagccag gcagggtggg | 1380 |
| agcaggggct ggcgtgggag gtctggggga cagacaagga tgatggaccc ctcagaggca | 1440 |
| agactaggat cagggacaga tctggaggcc caggacatgg ctgagaggtg gtcagcaggc | 1500 |
| tgggggcatg gagcagagag ggcttgggta caagctggag aggaaggaga ttctggcatg | 1560 |
| ttggggtgag ggcagaggga cagatgaggg gaggagggtg ctggctaaac aggaactgaa | 1620 |
| tgaatggcct gaagctccct ctcccaaggg ttcccactcc cattggcctg gccctgtacg | 1680 |

```
tgcactctgt catctccttg gtcaccctct gctccaggcc ttctccacca caggacctca    1740
gctgtccctc cttctaccca aggtggagtc ccccaaagtc ccttctgtct ggcctatcct    1800
gtgcccacca cctgtggctt catccagccc tcctcctcta tctttatctg ccataggccg    1860
cagccctggc ccctgtggga ttgaggtccc aagtggtcca gctgtggggt ttggtgctgg    1920
gaccctcaat ggcagccgga aggtccctct gaggcagaag ctcaagcccc atggggacag    1980
tggctcccca gtgcctggcc ctgagccatt tctgctgttt caggtgccca catcaccctc    2040
atttcctcct cgcagtagcc ctgcaccgtg ccagaaacc catccacagg caggcagtgg     2100
ctggggtccg ggtgccccgg gctgttgggc tctgcttcct ccctctgctc ccccatgtct    2160
ccctgagttc tcccaccttt gctcatttgt aaaatgggca ggtcaatctt cccaccccac    2220
cgtgtgggct gccccaaccc caaatgtgcc cagggagggg ggggaaccca aggcacaggc    2280
cccgcccctg cccccaagca gcactgggct actggctcac agaagcacct ttggttctgc    2340
aggtcatgcc cctccctgca gggaagggaa agctggtggt agaggctggg cacagactga    2400
cgtccagaag aagtcccttg gccctgctag ggtggcacca gacttctctg gtcccacagg    2460
acagccagtg gcctcccaac ttggttctgg gccccgcct gcaagcacac atggcaagga    2520
gggctttagc aggctcacat aaccgagtgg caaggcccct gctcccagag ctggatttg    2580
aatgaactcc gggcctgttt ggggaggtga agctgccagg tgtgcacagg ggcctcccag    2640
gctcctggct ccaccagcca aggaggtggg ggcaagggtc agggcaatgg gggacaatgc    2700
cgctcagggt gcagtgagct cccctgggaa aaccgaagcc agcaagacca ggagagggcc    2760
acctcactgg gcctgcctcc cccacctcct gggcctctct gacctcagct cctagaccct    2820
ggacccttgg ctgggactca gcattttcca gtcttttttca ggggtagaca ggggagcctg    2880
ggttaaactt taccactgtg ccctggccca ggcatcacca acacggcctc cctgcagctg    2940
ccctgccacc gacagacccc gattaaaccc acacctggcc ttggcctccc ctgctctata    3000
ccttgcatgt ttttttgcctc acttggaata aaattccaac tcctccctgt ggcgtaggag    3060
gttcttgggg gctgacccat caccccctctg gtggacagag acattgccag cgtggtggtc    3120
gtctgtgctt ggttcagggc aaggctggga ggcagtgggt gctgaggtct tcagtgagca    3180
aggagagagg cagggaggag gaggaggagg aggagagcac agcatgaaag gacgggaccc    3240
taaagggctt tggcccaagg gagggtgggg caagaatgtt ctgagacttc tgtgggcagc    3300
aaagaggact gagcacctgt tctccagccc ccaggactga gagcctgcag agacaagctg    3360
gcacagggcg aggggtggca gggaacttca gggtgggagg tgcatggggc aggcgggagg    3420
aggaagaaca gagaggggac agagagggta tgaatgggag ctcctggggt gcaggcttgc    3480
tttccactat gaatgggtgg aggagggaag agaagaaaat tgcttttgag acccacccag    3540
gctgggtggc ctcagggcct cccttgaatc cctgctccac ctcccacagc cttgtggact    3600
tgggcaagtc actggccacc tgagcctcag tttgcagtga cagtcaagac agctcaggcc    3660
aggcgtagtg gcttatgcct gtaatcccag catgttggga ggccgaggcg ggtggatcac    3720
ttgaggccag gagtttgaga ccagcctggc caacgtggtg aaaccccgtc tctactaaaa    3780
atacaaaaat tagcctggtg tggtggcacg cacctgtagt cccagctact cgagaggcta    3840
aggcaggaga atctcttgaa cctgggagac agaggttgca gtgagccgaa gtggcaccac    3900
tgcacaccag cctgggctac agagcacgct ctgtccaaat aaacaaacaa acaaacacta    3960
ctcagtgtct cagaaaggac agaaggggac tccctggctc aggcagaagc tcagtgggtg    4020
tgcatttcct tcaagactcg tccttcagaa ggaataggct tctgggcag tacagaggag     4080
```

-continued

```
tctaagtgag aggcaggcct ccctgggagc tgggcccagg ctctctgcag ccatgccttt    4140
aaggagtgcc tacggggtag cacgatcaga tggacaggcc agggctgccc agagctgggg    4200
gtgggagcaa ggtaagcaga gaggtgaggg aaggagggtg ctggcttagc aggagctgaa    4260
tgaatgggcc tggaggggaa aagctaaggg ggatgggtg gcttgagtgg agtaggtgag     4320
gcctaggtga aggggagctg tggaccttcc aggacggacg gatgtgagca gtcctgagtg    4380
gggactggag ttagggtggg gaagggaagc cccaggcagc cctgcaggc ccctgcccct    4440 gggccctacc gcagcagggc agccctgtct ctgggtctca gctgatgctt ccctctgccc    4500
actggcccct gacctggtgg gatttcccac catctctccc ggcccagcct gccctgccct    4560
cctaggtctt cccaacctcc cctctgcaga acatctcag ccacgtctgg caccccagg    4620 catccctgcc tgcctctagg aagttgaccc cttcaatggg tttcagcctc caaccccacc    4680
cccgcttgac tcctgctctg tcagcacttg cttgagaaaa tcatcctggg aaaccagctt    4740
ctgggagcag gggccttgcc actcggttct gcgagcctgc tgaagccctc cttgccacgt    4800
gtgcttgcag gcgggggccc agaactaagc taggaggcca ctggctgtcc tgtgggacca    4860
gggaagtctg gtgccaccct agcagagggc ccatggactt cttctggagg tcagtctgtg    4920
cccagcctct accaccagtc cagaacttgc agtgggtgcg gtaaacggtg gcccctcctc    4980
agcaaacatt tccaggggat tctggcagca gagtttccat gggaacatgt gctggttctg    5040
cgctgaaccc ggtgtggctg gggttccctt cacagccaat attgcaggaa ctgagcctgg    5100
tggcctcggc cagggtaggc agtgctcttt ggccacccag tgtcacaaac ctgaactcaa    5160
gttacaggca aaacctgctt ttccttttc tttctctctc tctctctttt ttttttgtt    5220 aaagcacatt ctaatgtaaa gtccatgctc cattctaaag atgcctctgg gatttcaggg    5280
atggattttt atgtagttca atagttttct tggcagacag cttatgcagg agaggtgggc    5340
cgttggctca gtccagccag gctgagtggc gtcactccat tccttgcaat gccaggggat    5400
gtcatttgtc cacctgaggg ggcttcccca gtctcccttc cctgacctgt ggtcagaatg    5460
atggcctcag ccttgactga gcgcgggtca ggccagactc tctgaacttg gtgttggcgt    5520
gtgttttgtg tgtgtctgga ggtgacatat gtgggtgaca gaagcatatg ttacagtgaa    5580
acattaaaac tacagcaaag tgaaaaaaaa aaaaaaaaaa                          5620
```

<210> SEQ ID NO 10
<211> LENGTH: 1732
<212> TYPE: DNA
<213> ORGANISM: Homo sapiens

<400> SEQUENCE: 10

```
gcatttccag agcagagttc agagaaaggc tgggctgctt gttgctggct aaaggacaaa      60
gggtaagttt caggaagcag aagagtgagc agatgaaatt cagcactggg atcaggggag    120
tgtctgattt gcaaaaggaa agtgcaaaga cagctcctcc cttctgagga aacgaaacca    180
acagcagtcc aagctcagtc agcagaagag ataaaagcaa acaggtctgg gaggcagttc    240
tgttgccact ctctctcctg tcaatgatgg atctcagaaa taccccagcc aaatctctgg    300
acaagttcat tgaagactat ctcttgccag acacgtgttt ccgcatgcaa atcaaccatg    360
ccattgacat catctgtggg ttcctgaagg aaaggtgctt ccgaggtagc tcctaccctg    420
tgtgtgtgtc caaggtggta aagggtggct cctcaggcaa gggcaccacc ctcagaggcc    480
gatctgacgc tgacctggtt gtcttcctca gtcctctcac cacttttcag gatcagttaa    540
```

| | |
|---|---|
| atcgccgggg agagttcatc caggaaatta ggagacagct ggaagcctgt caaagagaga | 600 |
| gagcattttc cgtgaagttt gaggtccagg ctccacgctg gggcaacccc cgtgcgctca | 660 |
| gcttcgtact gagttcgctc cagctcgggg aggggtgga gttcgatgtg ctgcctgcct | 720 |
| ttgatgccct gggtcagttg actggcggct ataaacctaa ccccaaatc tatgtcaagc | 780 |
| tcatcgagga gtgcaccgac ctgcagaaag agggcgagtt ctccacctgc ttcacagaac | 840 |
| tacagagaga cttcctgaag cagcgcccca ccaagctcaa gagcctcatc cgcctagtca | 900 |
| agcactggta ccaaaattgt aagaagaagc ttgggaagct gccacctcag tatgccctgg | 960 |
| agctcctgac ggtctatgct tgggagcgag ggagcatgaa acacatttc aacacagccc | 1020 |
| agggatttcg gacggtcttg gaattagtca taaactacca gcaactctgc atctactgga | 1080 |
| caaagtatta tgactttaaa accccatta ttgaaaagta cctgagaagg cagctcacga | 1140 |
| aacccaggcc tgtgatcctg gacccggcgg accctacagg aaacttgggt ggtggagacc | 1200 |
| caaagggttg gaggcagctg gcacaagagg ctgaggcctg gctgaattac ccatgcttta | 1260 |
| agaattggga tgggtcccca gtgagctcct ggattctgct gacccagcac actccaggca | 1320 |
| gcatccaccc cacaggcaga agaggactgg acctgcacca tcctctgaat gccagtgcat | 1380 |
| cttggggaa agggctccag tgttatctgg accagttcct tcatttcag gtgggactct | 1440 |
| tgatccagag aggacaaagc tcctcagtga gctggtgtat aatccaggac agaacccagg | 1500 |
| tctcctgact cctggccttc tatgccctct atcctatcat agataacatt ctccacagcc | 1560 |
| tcacttcatt ccacctattc tctgaaaata ttccctgaga gaacagag agatttagat | 1620 |
| aagagaatga aattccagcc ttgactttct tctgtgcacc tgatgggagg gtaatgtcta | 1680 |
| atgtattatc aataacaata aaaataaagc aaataccatt taaaaaaaaa aa | 1732 |

<210> SEQ ID NO 11
<211> LENGTH: 2115
<212> TYPE: DNA
<213> ORGANISM: Homo sapiens

<400> SEQUENCE: 11

| | |
|---|---|
| agtttccctt ccgctcacct ccgcctgagc agtggagaag gcggcactct ggtggggctg | 60 |
| ctccaggcat gcagatccca caggcgccct ggccagtcgt ctgggcggtg ctacaactgg | 120 |
| gctggcggcc aggatggttc ttagactccc cagacaggcc ctggaacccc ccaccttct | 180 |
| ccccagccct gctcgtggtg accgaagggg acaacgccac cttcacctgc agcttctcca | 240 |
| acacatcgga gagcttcgtg ctaaactggt accgcatgag ccccagcaac cagacggaca | 300 |
| agctggccgc cttccccgag gaccgcagcc agcccggcca ggactgccgc ttccgtgtca | 360 |
| cacaactgcc caacgggcgt gacttccaca tgagcgtggt cagggcccgg cgcaatgaca | 420 |
| gcggcaccta cctctgtggg gccatctccc tggccccaa ggcgcagatc aaagagagcc | 480 |
| tgcgggcaga gctcagggtg acagagagaa gggcagaagt gcccacagcc acccccagcc | 540 |
| cctcacccag gccagccggc cagttccaaa ccctggtggt tggtgtcgtg ggcggcctgc | 600 |
| tgggcagcct ggtgctgcta gtctgggtcc tggccgtcat ctgctcccgg gccgcacgag | 660 |
| ggacaatagg agccaggcgc accggccagc cctgaaggga ggaccctca gccgtgcctg | 720 |
| tgttctctgt ggactatggg gagctggatt tccagtggcg agagaagacc ccggagcccc | 780 |
| ccgtgccctg tgtccctgag cagacggagt atgccaccat tgtctttcct agcggaatgg | 840 |
| gcacctcatc ccccgcccgc aggggctcag ctgacggccc tcggagtgcc cagccactga | 900 |
| ggcctgagga tggacactgc tcttggcccc tctgaccggc ttccttggcc accagtgttc | 960 |

```
tgcagaccct ccaccatgag cccgggtcag cgcatttcct caggagaagc aggcagggtg    1020
caggccattg caggccgtcc aggggctgag ctgcctgggg gcgaccgggg ctccagcctg    1080
cacctgcacc aggcacagcc ccaccacagg actcatgtct caatgcccac agtgagccca    1140
ggcagcaggt gtcaccgtcc cctacaggga gggccagatg cagtcactgc ttcaggtcct    1200
gccagcacag agctgcctgc gtccagctcc ctgaatctct gctgctgctg ctgctgctgc    1260
tgctgctgcc tgcggcccgg ggctgaaggc gccgtggccc tgcctgacgc cccggagcct    1320
cctgcctgaa cttgggggct ggttggagat ggccttggag cagccaaggt gcccctggca    1380
gtggcatccc gaaacgccct ggacgcaggg cccaagactg gcacaggag tgggaggtac     1440 atggggctgg ggactcccca ggagttatct gctccctgca ggcctagaga gtttcaggg    1500 aaggtcagaa gagctcctgg ctgtggtggg cagggcagga aacccctcca cctttacaca   1560
tgcccaggca gcacctcagg ccctttgtgg ggcagggaag ctgaggcagt aagcgggcag   1620
gcagagctgg aggcctttca ggcccagcca gcactctggc ctcctgccgc cgcattccac   1680
cccagcccct cacaccactc gggagaggga catcctacgg tcccaaggtc aggagggcag   1740
ggctggggtt gactcaggcc cctcccagct gtggccacct gggtgttggg agggcagaag   1800
tgcaggcacc tagggccccc catgtgccca ccctgggagc tctccttgga acccattcct   1860
gaaattattt aaaggggttg gccgggctcc caccagggcc tgggtgggaa ggtacaggcg   1920
ttcccccggg gcctagtacc cccgccgtgg cctatccact cctcacatcc acacactgca   1980
cccccactcc tggggcaggg ccaccagcat ccaggcggcc agcaggcacc tgagtggctg   2040
ggacaaggga tcccccttcc ctgtggttct attatattat aattataatt aaatatgaga   2100
gcatgctaag gaaaa                                                   2115

<210> SEQ ID NO 12
<211> LENGTH: 5136
<212> TYPE: DNA
<213> ORGANISM: Homo sapiens

<400> SEQUENCE: 12
tgctgccagc cccgcccaga ctccaggcag gttctcgttg ctatggtgat cgccggtgca      60
agctggatgc ttggacgcgc cgctgccagt ccaacgcaga cccgcccac gacgtcgacg      120 attcgtgtag cccgcaggtc ccgcgtggct ctcgttgcca tggtgatcgc cgccgctggc     180
tcaggcggac caggccgcgc ggagcccag cttcacagc catcgctgga ctgtggaaga      240
atgaggtcct ccctgacacc tttggggccc ctgtgagcc gcgaccgtgt catcgccagc     300
ttccctaagt ggtacacgcc ggaagcctgt ttgcagctca gggagcactt ccacgggcag    360
gtcagcgctg cctgccaacg caggaacacg gggactgtcg ggctcaaact ctccaaggtg    420
gtggtggttg gcgatctcta cgtggggaag accagcctca tccacaggtt ttgcaagaat    480 gttttttgatc gagactacaa ggccaccatt ggggtgact ttgaaattga gcgctttgag    540
attgctggga ttccctatag cctccagatc tgggacacag ctgggcagga agttcaag     600 tgcatcgcat ctgcctacta ccggggtgcc caggtgatca tcacggcctt tgacctcact    660
gacgtgcaga ccctggagca taccaggcag tggttggagg atgctctgag ggagaacgag    720
gcaggctcct gcttcatctt cctcgtggga accaagaagg accttctgtc aggggccgca    780
tgtgagcagg ccgaagcaga cgctgtgcac ctggccaggg agatgcaggc cgagtactgg    840
tcagtgtcgg ccaagactgg cgagaacgtg aaggcattct tcagccgcgt agccgccctg    900
```

-continued

```
gcattcgagc agtcggtgct gcaggacctg gagaggcaga gcagtgcccg gctccaggtc      960
ggcaatggag acctaatcca aatggaaggg agtccgcccg agacccagga gagcaagagg     1020
ccctccagcc tgggctgctg ctaactgggg cctgcgtgga aggcctccgc tccctgcaca     1080
cacacggaca ggaatttccg tgactgtggt gtggagactg gagcccaagc tctgcagcgt     1140
gtcgccctca agctgtaggc ccatgttcca gtccctccac ccacccaccg ggctcagctc     1200
cagggcacag tcacttgtcc gttgcaggtt gggcactaga aaaggcccc actggctgcc      1260
tgggagcccc acaccaccgg gccagtgcag gcactgtggt gatcccataa aaggccagtc     1320
catttgcagg gtcatcagac agtcaccttt ggcctcaaga ggcctcagaa ctgcaaactc     1380
ctgcgtcggt ctatactact cggccatggc ccacatcagc agtcaaccct gcactctttc     1440
ccagcgatct tggatgtgtc cccaggatcc gtcacagtgt tccaggcaac ctggacttgt     1500
caaagtcagc acctgaagga gaggccacct gccattcccc ctgggagttt tctgttgtca     1560
gcaggactta tggttctggg tctcagagct tcaggcctca ctgtccttct gccacggatg     1620
ctcaaggttc ctgggcagac cagcacctct ggaggacaat ggacaaaatg tctcttagac     1680
ctgttctggc tgaagggcta tctctggcac ctctgagatc cctaggtcct gccctcctgg     1740
tccgtgggcc aggatgtgca gaacaaccac tcaggccttt ctggcccacc tggacagtgc     1800
atttacctgt gtgctgcggg aggcagactg cacagctgtc ctagggtaac tcactctgca     1860
gcccttgaac atggcactgc cctcctctgg cactcatgct gggcctgtgc ccactgctgc     1920
ctctccatcc ctctctcatt ggcctataca tctcttagga cctttgtaat ggtgtccatg     1980
cacctttaga ggacttcaga ggccctgcca agtctagcat gttcctgtct ccaacaccgc     2040
ctcctgcaca tgcagagcag acagaaatac cccacacatt ccccagcctc tctgcccagt     2100
atgctcatcc acagggtttt ctcactgcta tgaaccagcc ccacagcccc aggcccctgt     2160
cacctggcta tgcccactca tcccacccgt ctcgtgctgt tgcttcccgt agatggcgag     2220
caccttgcag gcagccttct gatcagtact gctctcctag ggcctggcac actgcagctg     2280
ccctgtaaat gttcagctca gcgattgcca aataccagtt agggaagaac actggcatct     2340
ttttctattc attccccctt caacatattt tttgtagttt tttatataaa tgactttttt     2400
tttttttga gatggagttt caccttgtt gcccaggctg gagtgcaatg gcgtaatctc       2460
ggctcagtgc aacctctgcc tcccaggttg aagcgattct cctgcctcag cctcccaagt     2520
agctgggatt acaggcatgc accaccatgc ctggctaatt ttgtattttt agtagagatg     2580
gggtttctcc atgttggtca ggctgctctc ggactcctga tctcaggtga cctgcccacc     2640
tcggcctccc gaagtgctgg gattacaagg gtgagccacc atgcccggcc ataaatgatt     2700
ttattcattt ttatgttttc ttttgggcgg cgggatggag tctctgtcac ccaggctggc     2760
gtgcaatggc acgatcttgg ctcactgcaa gcttcccctt ccgggttcat gccattctcc     2820
tgcctcagcc tcccgagtag ctgggactac aggcacgtgt gaccatgccg gctaattttt     2880
ttatattttt agtagagaga ggtttcaccg tgttagccag gatggtctcg atgatctgac     2940
ctcgtgatct gcccgcctcg gcctcccaaa gtgctgggat tacaggcctg agccaccgcg     3000
tccggcctcc ataaatgact tttaaagggg ttgtatgttt agtgtgaaca aagacagtac     3060
aaagcatata aaatacaagg tgaaagcccc cccccgccca cattagctgc gcccctgaag     3120
tgtctccagc agaagagatg gatgaatgga aggacacaca gatggacaga gagcaggaaa     3180
gactgttagc tctgctaaca gtcaggacta ttccttctgg actctgtgcc tttgcctgca     3240
cagctagtgt tgatggcttg tttgttgttt tcaccagagt gagctccttc tggacatact     3300
```

```
gcctggcagc ctgccttcct agggagctgg cgccaaggcc tctccctgat ggcacacaag      3360
gagcctcctt cctgtagcag cgcccagttt tcatgtggat ggattgtagt tcatttgacc      3420
ctccccatcc gcgggccatc cggcttgtgt ccagctttta gctcttgcca atggtgctgc      3480
agtggccatt cttgtagtta tagctttgcg tactcaggaa ggcccttctc ccgactgcgg      3540
cccccagcct ggtccactaa atgcagcctg tggtcgggca gacagcattg gggtccatta      3600
ggaagaccag gtttgctggg cataagcttc acaggacggg agaacctgcc catggtggac      3660
tgtcgttctc cacagctccc ttcccttgcc ccttcgggcc tccaggatat gtttgcgggg      3720
gtgggtgtgg tgtccagctg ttaccagctt ctgagctaga gctgtactgc ctcacgtaca      3780
cccccacctc tgtaaatggt ccttgattaa atcgtcctca tattacctcc tgcaatgtgc      3840
cagctgattc ccacacaccc tgactgacat agttgtggcc tctcgaactt tgatatttgg      3900
cctgggagga cagaagagta aggtcgccac ggaaacgcaa ggggctcagt tgtcccccca      3960
ccccaagttg atgcagcatc ttctcggtca gaattgcttc agggtggttt gcgcacccctc     4020 actttgatga tttaatgaag acatttcctt cttttcccagc atcgggcagt aagtttcctg     4080
ggcagaggca ctttctgttg gtctggtctt gtgggcccag gcaagcagcc ccctgcagcc      4140
aaggtgcggc aatgaccaca gtgaccgcgt ccaagtgctg ccgaaacgcc ttttcctct      4200 tccctgtttc cctggaccct ttcctgctct ctgtccatct gtgtgtcctt ccgttcacct      4260
gtctcttctg ctggagacac gtacctgaag caggtcctct cctgtcactt cctggctccc      4320
cagggctagg tcccagggtg ctctcgctct ggctttcgag gctcctcacc acccagccca      4380
ccccaccccc acaggcccct gtgctccagt ttcatccctg gtcacaatgc agtctgcaga      4440
tgccagaccc ctcttctgtg cccaacggct gggacacccc tactcccaga gaggcctctg      4500
tggacacccc cacagctctc gcagcacttg ataccttgag tgtgattggt cacatctggg      4560
ctttctcccc cacccatctg tggaacccca agagccagga cagtgacctc atcacctcta      4620
ctgtctcccc tagcacctct gggaggaagg gcccacagta ggtgctcaat agatgtgtaa      4680
agaaggcagg gaagcaagaa ggttgctcaa acaagaccat gttcccagca gacagattgc      4740
actctgaccc agatgccacc acacgaaact tacacctgcc tggggaacaa tcctgtgctt      4800
ggctctcctt ggtggccagg gacagttgtg cctcatccct cacttgcaaa ccccagtcct      4860
gtctgaccca gagaccctca cagggcatca gccagtgaag gcggtttggg gctgaggat      4920 atgttctgat cttgggaaga gcttggtagg agccagccac agaaagtttc agggcagaac      4980
tgaacaggtc tcgggaagga cacttcatgc cagctagaga ggctctgggc acaggaaaga      5040
attggacttc gggcagaaaa atgtttgtgc tatttagtac tatgtaacaa atcactccaa      5100
aacttcattg cttaaagcaa caaaaaaaaa aaaaaa                                5136
```

<210> SEQ ID NO 13
<211> LENGTH: 906
<212> TYPE: DNA
<213> ORGANISM: Homo sapiens

<400> SEQUENCE: 13

```
gtgcgctgct gcgcaggcgc ggtggtcgga cgacagaccg tgtgtttcca aaatggcggc       60
agcgatggat gtggataccc cgagcggcac caacagcggc gcgggcaaga agcgctttga      120
agtgaaaaag tggaatgcag tagccctctg ggcctgggat attgtggttg ataactgtgc      180
catctgcagg aaccacatta tggatctttg catagaatgt caagctaacc aggcgtccgc      240
```

```
tacttcagaa gagtgtactg tcgcatgggg agtctgtaac catgcttttc acttccactg    300
catctctcgc tggctcaaaa cacgacaggt gtgtccattg gacaacagag agtgggaatt    360
ccaaaagtat gggcactagg aaaagacttc ttccatcaag cttaattgtt ttgttattca    420
tttaatgact ttccctgctg ttacctaatt acaaattgga tggaactgtg tttttttctg    480
ctttgttttt tcagtttgct gtttctgtag ccatattgta ttctgtgtca aataaagtcc    540
agttggattc tggaacggat gctctctctt gtgtatgtga acaaagtgaa cataaatgaa    600
gagtctcccc ttccaaggct gaaaactcag cttttgaaag tgaaatgttt gttcatcggg    660
gccagagcag ggttgtcctc tgagcgcatc acttagtgac gaggaatcca acagctcaag    720
gcagagtgtg gatcaccggc tcccgaaaac agcagtcagc ccttcttttct cctgtgtgac    780 agcagtgggc agctgaaaga gggaagaatg tgggattcag tcatcaaacc cagttctgag    840
tcctggttcc acagcttggg tactgatggc aatcttggcc aagttgtctc tctactctga    900
actttc                                                                906
```

<210> SEQ ID NO 14
<211> LENGTH: 1214
<212> TYPE: DNA
<213> ORGANISM: Homo sapiens

<400> SEQUENCE: 14

```
cggcagcagc gagtggacat ggctgcactc ttccaagaag caagcagctg tcccgtctgc     60
tcagactatc tggaaaaacc aatgtccctg gagtgtggat gcaccgtctg cctcaagtgc    120
atcaattcgc tgcagaagga gccccatggg gaggatctgc tttgctgttg ctgttccatg    180
gtctctcaga ggaacaaaat caggcccaat cggcagctag agaggctggt ttcccacatc    240
aaggaactgg agcccaagct gaagaagatt ctacagatga acccaaggat gcggaagttc    300
caagtggata tgaccttgga tgccgacaca gccaacaact tcctcctcat ttctgacgac    360
ctcaggagcg tccgaagtgg gctcatcaca cagaatcggc aagaccttgc cgagagattt    420
gacgtgtccg tttgcatcct gggctcccct cgctttacct gtggccgcca ctactgggag    480
gtggacgtgg gaacaagcac agaatgggac ctggagtctg cagagaatc tgttcactgc    540 aaagggaaga tccagctgac cacagagctt ggattctgga ctgtgagttt gagggatgga    600
agccgcctct ctgccagcac ggtgccgctg actttcctct tagtagaccg caagttacag    660
cgagtgggga tttttctgga tatgggcatg cagaacgttt ccttttttga tgctgaaagt    720
ggttcccatg tctatacatt caggagcgtc tctgctgagg agccactgcg cccatttttg    780
gctccttcaa ttccacctaa tggtgatcaa ggtgtcttga gcatctgtcc tttgatgaac    840
tcaggcacta ctgatgctcc agtccgtcct ggggaggcca ataagccgc cactgcaaaa    900 aaaaacaggg tcagaaaatt acttgggtgg gtagactag gaattttcta cttggtaaaa    960
gcattataca gtcataggag aaagatatgg gacatttcta taatctatat tctaatttga   1020
ttcgattatt gagtcgtaag tattaattat tgccaccatc caactcattg agtcttatgg   1080
ttcacatctt gtttcctata gaatgttct gtattctcgg atcaatttcc aaatgctta   1140 ctttttcatt tctgtaagtt caaatcaatg tttaaattat agaagttatg aggtaaataa   1200
acatttggat atca                                                    1214
```

<210> SEQ ID NO 15
<211> LENGTH: 1773
<212> TYPE: DNA
<213> ORGANISM: Homo sapiens

<400> SEQUENCE: 15

```
aatgagcgaa ggcatcgcga gccagggggc gcggagaagg cggggaatca tggccgcccc    60
cagtgttccg cgtccggggg tttgtgggag ttgccttgac ctgcagctcc gccaccgcgg   120
acccgccttc tgccctcagc agcagacgct ctgtcccgcc cgggcagctc tgcgaggcag   180
cggctggaga gggaaccatg gggactgtgc acgcccggag tttggagcct cttccatcaa   240
gtggacctga ttttggagga ttaggagaag aagctgaatt tgttgaagtt gagcctgaag   300
ctaaacagga aattcttgaa acaaagatg tggttgttca acatgttcat tttgatggac    360
ttggaaggac taaagatgat atcatcattt gtgaaattgg agatgttttc aaggccaaaa   420
acctaattga ggtaatgcgg aaatctcatg aagcccgtga aaaattgctc cgtcttggaa   480
tttttagaca agtggatgtt ttgattgaca catgtcaagg tgatgacgca cttccaaatg   540
ggttagacgt tacctttgaa gtaactgaat tgaggagatt aacgggcagt tataacacca   600
tggttggaaa caatgaaggc agtatggtac ttggcctcaa gcttcctaat cttcttggtc   660
gtgcagaaaa ggtgaccttt cagttttcct atggaacaaa agaaacttcg tatggcctgt   720
ccttcttcaa accacggccc ggaaacttcg aaagaaattt ctctgtaaac ttatataaag   780
ttactggaca gttcccttgg agctcactgc gggagacgga cagaggaatg tcagctgagt   840
acagttttcc catatggaag accagccaca ctgtcaagtg ggaaggcgta tggcgagaac   900
tgggctgcct ctcaaggacg gcgtcatttg ctgttcgaaa agaaagcgga cattcactga   960
aatcatctct ttcgcacgcc atggtcatcg attctcggaa ttcttccatc ttaccaagga  1020
gaggtgcttt gctgaaagtt aaccaggaac tggcaggcta cactggcggg gatgtgagct  1080
tcatcaaaga agattttgaa cttcagttga caagcaact catatttgat tcagttttt    1140
cagcgtcttt ctggggcgga atgttggtac ccattggtga taagccgtca agcattgctg  1200
ataggtttta ccttggggga cccacaagca tccgcggatt cagcatgcac agcatcgggc  1260
cacagagcga aggagactac ctaggtggag aagcgtactg ggccggcggc ctgcacctct  1320
acacccccatt acctttccgg ccaggccagg gtggcttttgg agaacttttc gaacacact  1380
tctttctcaa cgcaggaaac ctctgcaacc tcaactatgg ggagggcccc aaagctcata  1440
ttcgtaagct ggctgagtgc atccgctggt cgtacggggc cgggattgtc ctcaggcttg  1500
gcaacatcgc tcggttggaa cttaattact gcgtccccat gggagtacag acaggcgaca  1560
ggatatgtga tggcgtccag tttggagctg ggataaggtt cctgtagccg acacccctac  1620
aggagaagct ctgggactgg ggcagcagca aggcgcccat gccacacacc gtctctcgag  1680
gaaacgcggt tcagcgattc tttgactgcg gaccctgtgg gaaacccgcgt caataaatgt  1740
taaagacaca ctccgaaaaa aaaaaaaaaa aaa                                1773
```

<210> SEQ ID NO 16
<211> LENGTH: 1749
<212> TYPE: DNA
<213> ORGANISM: Homo sapiens

<400> SEQUENCE: 16

```
tttgtttgag cggcggcgcg cgcgtcagcg tcaacgccag cgcctgcgca ctgagggcgg    60
cctggtcgtc gtctgcggcg gcggcggcgg ctgaggagcc cggctgaggc gccagtaccc   120
ggcccggtcc gcattcgcc ttccggcttc ggtttccctc ggcccagcac gccccggccc    180
cgccccagcc ctcctgatcc ctcgcagccc ggctccggcc gccgcctct gccgccgcaa    240
```

| | |
|---|---|
| tgatgatgat ggcgctgagc aagaccttcg ggcagaagcc cgtgaagttc cagctggagg | 300 |
| acgacggcga gttctacatg atcggctccg aggtgggaaa ctacctccgt atgttccgag | 360 |
| gttctctgta caagagatac ccctcactct ggaggcgact agccactgtg aagagagga | 420 |
| agaaaatagt tgcatcgtca catggtaaaa aaacaaaacc taacactaag gatcacggat | 480 |
| acacgactct agccaccagt gtgaccctgt aaaagcctc ggaagtggaa gagattctgg | 540 |
| atggcaacga tgagaagtac aaggctgtgt ccatcagcac agagcccccc acctacctca | 600 |
| gggaacagaa ggccaagagg aacagccagt gggtacccac cctgcccaac agctcccacc | 660 |
| acttagatgc cgtgccatgc tccacaacca tcaacaggaa ccgcatgggc cgagacaaga | 720 |
| agagaacctt ccccctttgc tttgatgacc atgacccagc tgtgatccat gagaacgcat | 780 |
| ctcagcccga ggtgctggtc ccatccggc tggacatgga gatcgatggg cagaagctgc | 840 |
| gagacgcctt cacctggaac atgaatgaga agttgatgac gcctgagatg ttttcagaaa | 900 |
| tcctctgtga cgatctggat ttgaacccgc tgacgtttgt gccagccatc gcctctgcca | 960 |
| tcagacagca gatcgagtcc taccccacgg acagcatcct ggaggaccag tcagaccagc | 1020 |
| gcgtcatcat caagctgaac atccatgtgg gaaacatttc cctggtggac cagtttgagt | 1080 |
| gggacatgtc agagaaggag aactcaccag agaagtttgc cctgaagctg tgctcggagc | 1140 |
| tgggggttggg cggggagttt gtcaccacca tcgcatacag catccgggga cagctgagct | 1200 |
| ggcatcagaa gacctacgcc ttcagcgaga accctctgcc cacagtggag attgccatcc | 1260 |
| ggaacacggg cgatgcggac cagtggtgcc cactgctgga gactctgaca gacgctgaga | 1320 |
| tggagaagaa gatccgcgac caggacagga acacgaggcg gatgaggcgt cttgccaaca | 1380 |
| cggccccggc ctggtaacca gcccatcagc acacggctcc cacggagcat ctcagaagat | 1440 |
| tgggccgcct ctcctccatc ttctggcaag gacagaggcg aggggacagc ccagcgccat | 1500 |
| cctgaggatc gggtgggggt ggagtggggg cttccaggtg gcccttcccg gcacacattc | 1560 |
| catttgttga gccccagtcc tgcccccac cccacccctcc ctaccctcc ccagtctctg | 1620 |
| gggtcaggaa gaaaccttat tttaggttgt gttttgtttt tgtataggag ccccaggcag | 1680 |
| ggctagtaac agttttttaaa taaaaggcaa caggtcatgt tcaatttctt caacaaaaaa | 1740 |
| aaaaaaaaa | 1749 |

```
<210> SEQ ID NO 17
<211> LENGTH: 4171
<212> TYPE: DNA
<213> ORGANISM: Homo sapiens

<400> SEQUENCE: 17
```

| | |
|---|---|
| ctgcatctct ccctctcacc cgtgtctcct ctcctctctt tccttctcgt cttctccctg | 60 |
| tcacgcatct ctcatcactc cccctcattc tgcctttcct cctactcacg gtctcctctc | 120 |
| cctctccctc tctctctctc cccctccctc tttctctctc tctctctttc tccacctcct | 180 |
| cccgaccccc tttcccctct atttctattg gcttctgtgt cccttgctcc cctcttctct | 240 |
| tcctcaccct gggaagcttc tcccccctat ccttgcccct gcccccccag gatgtgtcct | 300 |
| ggagatgggg ggtgacgtac caggctctgg ttgggaagtc agggccggag accagatggg | 360 |
| agaggctctg tggacagccg tggccgaggg cctggagggg aacctgagcc cgcaagcggt | 420 |
| ctagaagtgg gtgccttgtg gggacccag ttaggagtgc ctgggggca cctggggact | 480 |
| gggcagggag aggggacagc agaatgataa ccagcctggc ggcaaggagg gaagccctca | 540 |
| ccccatgggc aggcaaatag ctgactgctg accaccctcc cctcagccat ggacatgctt | 600 |

```
catccatcat cggtgtccac gacctcagaa cctgagaatg cctcctcggc ctggccccca    660
gatgccaccc tgggcaacgt gtcggcgggc ccaagcccgg cagggctggc cgtcagtggc    720
gttctgatcc ccctggtcta cctggtggtg tgcgtggtgg gcctgctggg taactcgctg    780
gtcatctatg tggtcctgcg gcacacggcc agcccttcag tcaccaacgt ctacatcctc    840
aacctggcgc tggccgacga gctcttcatg ctggggctgc ccttcctggc cgcccagaac    900
gccctgtcct actggcccctt cggctccctc atgtgccgcc tggtcatggc ggtggatggc    960
atcaaccagt tcaccagcat attctgcctg actgtcatga gcgtggaccg ctacctggcc   1020
gtggtacatc ccacccgctc ggcccgctgg cgcacagctc cggtgcccg cacggtcagc    1080 gcggctgtgt gggtggcctc agccgtggtg gtgctgcccg tggtggtctt ctcgggagtg   1140
ccccgcggca tgagcacctg ccacatgcag tggcccgagc cggcggcggc ctggcgagcc   1200
ggcttcatca tctacacggc cgcactgggc ttcttcgggc cgctgctggt catctgcctc   1260
tgctacctgc tcatcgtggt gaaggtgcgc tcagctgggc gccgggtgtg ggcaccctcg   1320
tgccagcggc ggcggcgctc cgaacgcagg gtcacgcgca tggtggtggc cgtggtggcg   1380
ctcttcgtgc tctgctggat gcccttctac gtgctcaaca tcgtcaacgt ggtgtgccca   1440
ctgcccgagg agcctgcctt ctttgggctc tacttcctgg tggtggcgct gcctatgcc    1500 aacagctgtg ccaaccccat cctttatggc ttcctctcct accgcttcaa gcagggcttc   1560
cgcagggtcc tgctgcggcc ctcccgccgt gtgcgcagcc aggagcccac tgtggggccc   1620
ccggagaaga ctgaggagga ggatgaggag gaggaggatg gggaggagag cagggagggg   1680
ggcaagggga aggagatgaa cggccgggtc agccagatca cgcagcctgg caccagcggg   1740
caggagcggc cgcccagcag agtggccagc aaggagcagc agctcctacc ccaagaggct   1800
tccactgggg agaagtccag cacgatgcgc atcagctacc tgtaggggcc tggggaaagc   1860
caggatggcc cgaggaagag gcagaagccg tgggtgtgcc tagggcctac ttcccaaggt   1920
gccacaggcc catgatggga tgttgagggg cctggacttt gatgctattg ctgccaggtc   1980
ttgctgtgtg accttgggta ggttgcttct actctctggg ccttgttttc tcctctgtga   2040
ctcagggata ggagtcatca gcctggatga gctatgtcag atgagaggtt tggagggcac   2100
tgttgctggg ctgacctggc tgagcaggca aaggtgggt gcagactggc ctcccccag    2160 ggatggagtg tcttggggca tcaactagaa tcttggccct cagagggata aaccaaggcc   2220
aggatttctt gggctcagag tcaggaacac aggagctgct gggggctggg ctggaaacct   2280
aaacagaaga aagcctaacc cggtgggagg agtggggcag aaatggtcag gccccagatc   2340
agctccctcc cctcgactgt gaggccttgg accagctctg ctcctctcta ggcctcaggc   2400
ttcacctggg taaaacccaa caacctctac acccttttgg cccaggcagt caatgctgga   2460
ggtcctgtgc cctggacgg gaagagcagg tgaatttcct gctcatggaa gcgaatgaag    2520
tccagcttca gggtctctca ctgcctgggc ttttgcaagg ccctgcatct acttttgtac   2580
ttgtcatttt gtattcgttt tcttaaagag ggacctcgaa ctgcataagc ttaggccacc   2640
caaagcctgg ctctgcccct gctgaggtca gccacccaat ccccaaggaa gctcatgttg   2700
ggtcttatgc ctggagtagg ggcccccggg ggttcccagg tcttttgagg gcttccaggc   2760
acctccttgt aggaagggcc atccctgttc ctctccttgt gacccatatt ctcccttcct   2820
ggagaccgag acagggaccc agcccatgag gactggcatg gaaaggcaga gtgtctgaag   2880
agcgctgtga ggagaaggaa gaggaaggga gaagaggaag aggaaggaga aggaagagga   2940
```

-continued

```
agacaagggg gaaaggggag gatgaggagg gggaaggaga agtacagatc tgtttcctgg    3000
agccgtcttt ggcccccctg ggctgagctc agtggtagca tctgtgaacc tgagttgccg    3060
acaacagccc cacccaacca gtactgaggg aaggacacga tcagggtgga acagccaggg    3120
tgcaatggca aatgcacaga gtacagacag gcacagggcc tgcgtccctg aggggcctca    3180
gagtgctgcc aagagggctc aggccttaat aaagccctag ggtggagctg ctaccaggg    3240
acattgggag gactgggag ctccctcccc atgctctatc atcctggaga ctacaggtcg     3300
ggaggcccag ggaagacaag aagaggctga agtgggactg tggaggggga ccatggggag    3360
cagccaccat ccaaggctgg gcctagactc cctcccagag atggtccctc agagctgtgg    3420
tgaggctggc cctgggaggg tgagaccccc ggtgaaatcc ttccgcttcc ccaccccttg    3480
cagagggcag gggtcctcag ggaaagcaca ggaaccagac ttttggagac ttggatcttc    3540
agcacacctc agggtcctgg gctggcattg gccttccggg cctcaatttc cccatcaaca    3600
aatggagatg aatcccagct tggctgcctc ctgggatcta acgagaaaat gagtcatgtg    3660
aggtaacttc caggctcact gcaatgggta cggtggggtg tatcagatta taaagtgggg    3720
gtgccctcct cacccccagg cttggcctat accccctct ccatcaagtg gcctctctgt     3780
gtctgtcctt tggggtgagg acactgtagg ccatgagaaa tggcagttg ggggtcaga      3840
ggccaagggt tagggaggca gggcttgggg agagtgtggg accatcagaa gagaaggaag    3900
tttacaaaac cacattttgt gtggagatgg aggctggagg cccggccctg ggacttggtc    3960
tggggtttct tgaggaagat ctgagggtcc aagggaggaa ggatgccctg gccttctggc    4020
cttctctggc tgatcctgcc ttcttgctgc ctaggacagg agagtaatgt cctagaatgg    4080
tccctgggag gccagttagg aaacccttg ctgcttctgt ctctagctct tgtcaataaa     4140
gacggtgaca cctgaaaaaa aaaaaaaaa a                                    4171
```

<210> SEQ ID NO 18
<211> LENGTH: 3597
<212> TYPE: DNA
<213> ORGANISM: Homo sapiens

<400> SEQUENCE: 18

```
gaccgaccct ccggctccac gcccttttt tttttttttt ttaggtcccg ggcgttgagc     60
tctactcagt gcacgcagcc acacaatatg ctcttggacg tcgcccctg gagggggatgt    120
tatctcccgc ctccttgaag tcgcccattt ctggggttgc cccatccagg gagctggttc    180
ctagttaaga atatgagaat gtatgcgcag ggaggcaggc aacagcacga acagccacgc    240
ttctagaaga ttctagggag cgcgcaggag cagcgcagag ggagtaggaa tgagcaggcg    300
gaggacccga ggtcacgaga ccgttgggtg ggaggagcca gcggccgggg aggttctagt    360
ctgttctgtc ttgcggcagc cgcccccttc tgcgcggtca cgccgagcca gcgcctgggc    420
ctggaaccgg gccgtagccc ccccagtttc gcccaccacc tccctaccat ggaccccgc     480
aaagtgaacg agcttcgggc cttttgtgaaa atgtgtaagc aggatccgag cgttctgcac    540
accgaggaaa tgcgcttcct gagggagtgg gtggagagca tgggtggtaa agtaccacct    600
gctactcaga aagctaaatc agaagaaaat accaaggaag aaaaacctga tagtaagaag    660
gtggaggaag acttaaaggc agacgaacca tcaagtgagg aaagtgatct agaaattgat    720
aaagaaggtg tgattgaacc agacactgat gctcctcaag aaatgggaga tgaaaatgcg    780
gagataacgg aggagatgat ggatcaggca aatgataaaa aagtggctgc tattgaagcc    840
ctaaatgatg gtgaactcca gaaagccatt gacttattca cagatgccat caagctgaat    900
```

```
cctcgcttgg ccatttttgta tgccaagagg gccagtgtct tcgtcaaatt acagaagcca    960
aatgctgcca tccgagactg tgacagagcc attgaaataa atcctgattc agctcagcct   1020
tacaagtggc gggggaaagc acacagactt ctaggccact gggaagaagc agcccatgat   1080
cttgcccttg cctgtaaatt ggattatgat gaagatgcta gtgcaatgct gaaagaagtt   1140
caacctaggg cacagaaaat tgcagaacat cggagaaagt atgagcgaaa acgtgaagag   1200
cgagagatca agaaagaat agaacgagtt aagaaggctc gagaagagca tgagagagcc   1260
cagagggagg aagaagccag acgacagtca ggagctcagt atggctcttt tccaggtggc   1320
tttcctgggg gaatgcctgg taattttccc ggaggaatgc ctggaatggg aggggcatg   1380
cctggaatgg ctggaatgcc tggactcaat gaaattctta gtgatccaga ggttcttgca   1440
gccatgcagg atccagaagt tatggtggct ttccaggatg tggctcagaa cccagcaaat   1500
atgtcaaaat accagagcaa cccaaaggtt atgaatctca tcagtaaatt gtcagccaaa   1560
tttggaggtc aagcgtaatg tccttctgat aaataaagcc cttgctgaag gaaaagcaac   1620
ctagatcacc ttatggatgt cgcaataata caaaccagtg tacctctgac cttctcatca   1680
agagagctgg ggtgctttga agataatccc taccccctctc ccccaaatgc agctgaagca   1740
ttttacagtg gtttgccatt agggtattca ttcagataat gttttcctac taggaattac   1800
aaactttaaa cacttttttaa atcttcaaaa tatttaaaac aaatttaaag ggcctgttaa   1860
ttcttatatt tttctttact aatcattttg gatttttttc tttgaattat tggcagggaa   1920
tatacttatg tatggaagat tactgctctg agtgaaataa aagttattag tgcgaggcaa   1980
acataactca tttgaggata aagtttgtgt tggatatgtg gttcctgatg cattttgact   2040
tgtcttttta aatgctttat ctttttcttt aaagatttat ttcaataaaa ctaattggga   2100
ccacccgtat ttcagtagga cctgggtagg gattggaagt acttggcagg gcagcagcaa   2160
tcttgctgtg tttgatataa catgcatcct tgggcaggtt gccctttaaat cttacactgt   2220
ggtgaaggga tgttttttttt gtaatgctgc agtagagttg gagtacttag ttctcttgtt   2280
gtccagtata tctaataagt gtttttcata ttatttccac gtaagggaaa taaggtagta   2340
cttttctttt tatatttcta tgcttaaaat tctctttcct agtcaaaaat tgcccaaatc   2400
tgtgtttgct ttctgcttgc tacatttgtc tcccttactt ttcttgagct aaagacaggc   2460
ttttttccacc ggcatcatca ctgctatcat cattaacagc gtaattatac aagcatattt   2520
aatgctgagt ttaatttaat atgtaataca tatggtaatt gtagggtaat acccacaaca   2580
actgtagttt cttacttggc caagagaatg cttatttaag tgttagactt ccattctggc   2640
aaaatcttgc cttatcagaa gacattggaa agagggattc cctttggtgt ttggtcttct   2700
acttagaaaa acctattgca gttagtttat cttgtagtat tcatctttgt attctgaaga   2760
taaggtttga attaaattga tacacacaga ggggaaccga ttttttttat ccaatgtgaa   2820
ttataaatga gataatccac agttattcat tgtgagttg ttgagactat gaagactca    2880
ttgtctttgt attcagctct taaatagtgt aactatatcc ccacctctgc ttgctttctt   2940
tccctcccct ccaatgataa agaaaatgat aaatttctg ttgtgcattc aattcttatt    3000
ttaaataaga ctaagtatag gcattgtacc tgacattgct acgttctac cagtgtttca    3060
atttaaagtg ctagtgttta aaacatttt caagggataa ggccttctgt actttgctta    3120
tttgaagaat cagtggtagg agcagtgaag taaattctat ggagtacatt tctaaaatac   3180
cacatttctg aaatcataaa taagtttatt caggttctaa cccttgctg tacacaagca    3240
```

| | |
|---|---|
| gacagaaatg catctgttac ataaatgaga aaaagctatt atgctgatgg agcatgcttt | 3300 |
| ttaaatcctt taaaaacact caccatataa acttgcattt gagcttgtgt gttcttttgt | 3360 |
| taatgtgtag agttctcctt tctcgaaatt gccagtgtgt acttggctta actcaagaac | 3420 |
| agtttcttct ggattcctta tttgatttat ttaacctaat tatattctaa tattgcaaat | 3480 |
| attaccataa gtgggtaaaa gtaaaattcc tcttctgaaa atgtgtcctg tgcttttaga | 3540 |
| tttttaaatt ccataatata cattcttaat tttcaactca aaaaaaaaaa aaaaaa | 3597 |

<210> SEQ ID NO 19
<211> LENGTH: 4326
<212> TYPE: DNA
<213> ORGANISM: Homo sapiens

<400> SEQUENCE: 19

| | |
|---|---|
| gctgagcgcg gagccgcccg gtgattggtg ggggcggaag ggggccgggc gccagcgctg | 60 |
| ccttttctcc tgccgggtag tttcgctttc ctgcgcagag tctgcggagg ggctcggctg | 120 |
| caccgggggg atcgcgcctg gcagacccca gaccgagcag aggcgaccca gcgcgctcgg | 180 |
| gagaggctgc accgccgcgc ccccgcctag cccttccgga tcctgcgcgc agaaaagttt | 240 |
| catttgctgt atgccatcct cgagagctgt ctaggttaac gttcgcactc tgtgtatata | 300 |
| acctcgacag tcttggcacc taacgtgctg tgcgtagctg ctcctttggt tgaatcccca | 360 |
| ggcccttgtt ggggcacaag gtggcaggat gtctcagtgg tacgaacttc agcagcttga | 420 |
| ctcaaaattc ctggagcagg ttcaccagct ttatgatgac agttttccca tggaaatcag | 480 |
| acagtacctg gcacagtggt tagaaaagca agactgggag cacgctgcca atgatgtttc | 540 |
| atttgccacc atccgttttc atgacctcct gtcacagctg gatgatcaat atagtcgctt | 600 |
| ttctttggag aataacttct tgctacagca taacataagg aaaagcaagc gtaatcttca | 660 |
| ggataatttt caggaagacc caatccagat gtctatgatc atttacagct gtctgaagga | 720 |
| agaaaggaaa attctggaaa acgcccagag atttaatcag gctcagtcgg ggaatattca | 780 |
| gagcacagtg atgttagaca aacagaaaga gcttgacagt aaagtcagaa atgtgaagga | 840 |
| caaggttatg tgtatagagc atgaaatcaa gagcctggaa gatttacaag atgaatatga | 900 |
| cttcaaatgc aaaaccttgc agaacagaga acacgagacc aatggtgtgg caaagagtga | 960 |
| tcagaaacaa gaacagctgt tactcaagaa gatgtatttta atgcttgaca ataagagaaa | 1020 |
| ggaagtagtt cacaaaataa tagagttgct gaatgtcact gaacttaccc agaatgccct | 1080 |
| gattaatgat gaactagtgg agtggaagcg gagacagcag agcgcctgta ttgggggggcc | 1140 |
| gcccaatgct tgcttggatc agctgcagaa ctggttcact atagttgcgg agagtctgca | 1200 |
| gcaagttcgg cagcagctta aaagttgga ggaattggaa cagaaataca cctacgaaca | 1260 |
| tgaccctatc acaaaaaaca aacaagtgtt atgggaccgc accttcagtc ttttccagca | 1320 |
| gctcattcag agctcgtttg tggtggaaag acagccctgc atgccaacgc accctcagag | 1380 |
| gccgctggtc ttgaagacag gggtccagtt cactgtgaag ttgagactgt tggtgaaatt | 1440 |
| gcaagagctg aattataatt tgaaagtcaa agtcttattt gataaagatg tgaatgagag | 1500 |
| aaatacagta aaaggattta ggaagttcaa cattttgggc acgcacacaa agtgatgaa | 1560 |
| catggaggag tccaccaatg gcagtctggc ggctgaattt cggcacctgc aattgaaaga | 1620 |
| acagaaaaat gctggcacca gaacgaatga gggtcctctc atcgttactg aagagcttca | 1680 |
| ctcccttagt tttgaaaccc aattgtgcca gcctggtttg gtaattgacc tcgagacgac | 1740 |
| ctctctgccc gttgtggtga tctccaacgt cagccagctc ccgagcggtt gggcctccat | 1800 |

```
cctttggtac aacatgctgg tggcggaacc caggaatctg tccttcttcc tgactccacc   1860
atgtgcacga tgggctcagc tttcagaagt gctgagttgg cagttttctt ctgtcaccaa   1920
aagaggtctc aatgtggacc agctgaacat gttgggagag aagcttcttg gtcctaacgc   1980
cagccccgat ggtctcattc cgtggacgag gttttgtaag gaaatatataa atgataaaaa   2040 ttttcccttc tggctttgga ttgaaagcat cctagaactc attaaaaaac acctgctccc   2100
tctctggaat gatgggtgca tcatgggctt catcagcaag gagcgagagc gtgccctgtt   2160
gaaggaccag cagccgggga ccttcctgct gcggttcagt gagagctccc gggaaggggc   2220
catcacattc acatgggtgg agcggtccca aacggaggc gaacctgact tccatgcggt   2280
tgaaccctac acgaagaaag aactttctgc tgttactttc cctgacatca ttcgcaatta   2340
caaagtcatg gctgctgaga atattcctga gaatcccctg aagtatctgt atccaaatat   2400
tgacaaagac catgcctttg aaagtattta ctccaggcca aaggaagcac cagagccaat   2460
ggaacttgat ggccctaaag gaactggata tatcaagact gagttgattt ctgtgtctga   2520 agttcacccct tctagacttc agaccacaga caacctgctc cccatgtctc ctgaggagtt   2580
tgacgaggtg tctcggatag tgggctctgt agaattcgac agtatgatga acacagtata   2640
gagcatgaat tttttcatc ttctctggcg acagttttcc ttctcatctg tgattccctc   2700
ctgctactct gttccttcac atcctgtgtt tctagggaaa tgaaagaaag gccagcaaat   2760
tcgctgcaac ctgttgatag caagtgaatt tttctctaac tcagaaacat cagttactct   2820
gaagggcatc atgcatctta ctgaaggtaa aattgaaagg cattctctga agagtgggtt   2880
tcacaagtga aaaacatcca gatacaccca agtatcagg acgagaatga gggtcctttg   2940
ggaaaggaga agttaagcaa catctagcaa atgttatgca taaagtcagt gcccaactgt   3000
tataggttgt tggataaatc agtggttatt tagggaactg cttgacgtag gaacggtaaa   3060
tttctgtggg agaattctta catgtttcct ttgctttaag tgtaactggc agttttccat   3120
tggtttacct gtgaaatagt tcaaagccaa gtttatatac aattatatca gtcctctttc   3180
aaaggtagcc atcatggatc tggtaggggg aaaatgtgta ttttattaca tctttcacat   3240 tggctatta aagacaaaga caaattctgt ttccttgagaa gagaatatta gctttactgt   3300
ttgttatggc ttaatgacac tagctaatat caatagaagg atgtacattt ccaaattcac   3360
aagttgtgtt tgatatccaa agctgaatac attctgcttt catcttggtc acatacaatt   3420
atttttacag ttctcccaag ggagttaggc tattcacaac cactcattca aaagttgaaa   3480
ttaaccatag atgtagataa actcagaaat ttaattcatg tttcttaaat gggctacttt   3540 gtccttttg ttattagggt ggtatttagt ctattagcca caaaattggg aaaggagtag   3600
aaaaagcagt aactgacaac ttgaataata caccagagat aatatgagaa tcagatcatt   3660
tcaaaactca tttcctatgt aactgcattg agaactgcat atgtttcgct gatatatgtg   3720
tttttcacat ttgcgaatgg ttccattctc tctcctgtac ttttccaga cacttttttg   3780 agtggatgat gtttcgtgaa gtatactgta ttttaccctt tttccttcct tatcactgac   3840
acaaaaagta gattaagaga tgggtttgac aaggttcttc cctttacat actgctgtct   3900 atgtggctgt atcttgtttt tccactactg ctaccacaac tatattatca tgcaaatgct   3960
gtattcttct tggtggaga taaagatttc ttgagttttg ttttaaaatt aaagctaaag   4020
tatctgtatt gcattaaata taatatgcac acagtgcttt ccgtggcact gcatacaatc   4080
tgaggcctcc tctctcagtt tttatataga tggcgagaac ctaagtttca gttgattta   4140
```

| | |
|---|---|
| caattgaaat gactaaaaaa caaagaagac aacattaaaa caatattgtt tctaattgct | 4200 |
| gaggtttagc tgtcagttct ttttgcccct tgggaattcg gcatggtttc attttactgc | 4260 |
| actagccaag agacttttact tttaagaagt attaaaattc taaaattcaa aaaaaaaaaa | 4320 |
| aaaaaa | 4326 |

<210> SEQ ID NO 20
<211> LENGTH: 2290
<212> TYPE: DNA
<213> ORGANISM: Homo sapiens

<400> SEQUENCE: 20

| | |
|---|---|
| agcaggtgag gacgggctag gcagcgcggg gagggattcg gactcggggc gggcctgcac | 60 |
| gagggcatcg gctccacagg gaccagtcat ccccaaaacg agggggatatc agcttaccga | 120 |
| ggccgcaggt tttcctagtc cctacctcat agatatgtag gacatccccg ggcccggaat | 180 |
| gcggctctct gaccctctct gtgccctccc ccgcccccccg aaccaggctt ggcgggcgga | 240 |
| ggcgccagcg gatgtctcat gcaaggatcg tctctgtggc taagcctcac tttccgctcc | 300 |
| gcccgggtgc tctctagagc ccggttttttc gagtggcagt ctccagggct gccgaataca | 360 |
| gcagcgatgg agaacggcac cgggccctac ggagaagaac gtccacgtga agtccaggag | 420 |
| acgacagtca ccgagggggc tgccaaaatc gcctttccca gtgccaacga ggtcttttat | 480 |
| aacccggtgc aggaattcaa tcgggacctg acatgtgctg tgatcaccga gtttgctcgc | 540 |
| attcagcttg ggccaaagg aatccagatc aaggttccag gagagaagga cacgcaaaaa | 600 |
| gtggtcgtgg acttgtcaga gcaagaggag gaaaaggttg aactgaaaga gagtgaaaac | 660 |
| ctggcctcag gagaccaacc tcgcacagcg gccgtggggg agatctgtga ggaaggcctg | 720 |
| catgtgctga aaggcctggc agcttcaggc ctacgttcca ttcgatttgc cctagaggtg | 780 |
| cctgggctca gatctgtggt tgcaaacgat gcctccaccc gggctgtgga tctcatacgc | 840 |
| cggaatgtcc agctcaatga cgtggcccac ctggtacagc cgagccaagc agatgcccgg | 900 |
| atgctgatgt accagcacca gagggtgtcg gagaggtttg acgtcatcga tctggacccc | 960 |
| tatggcagcc cagccacctt cctggatgca gctgtgcagg ctgtgagtga aggagggttg | 1020 |
| ctgtgtgtga cctgcacaga catggcggtg ttggcgggga acagcgggga gacgtgctac | 1080 |
| agcaagtacg gggccatggc cctcaagagc cgggcctgcc acgagatggc cctgagaatc | 1140 |
| gtcctgcaca gcctggacct ccgcgccaac tgctaccagc gcttcgtggt gccgctgctc | 1200 |
| agcatcagcg ctgacttcta cgtgcgtgtt tttgtccgtg tcttcaccgg ccaggccaag | 1260 |
| gtcaaggcct cagccagcaa gcaggcgctg tgttccagt gtgtgggctg cggggccttc | 1320 |
| caccttcagc gtctcggcaa agcgtcagga gtccccagcg gccgggccaa gttctctgca | 1380 |
| gcctgtggtc cccctgtgac ccccgagtgt gaacactgtg gcaacgaca ccagcttggt | 1440 |
| ggccccatgt gggcagagcc catccatgac ctggattttg tgggccgtgt cctggaggct | 1500 |
| gtgagcgcta accccggccg cttccacacc tcggagcgga tccgaggggt cctgagcgtc | 1560 |
| atcactgagg agctcccgga cgtgcctctg tactacaccc tggaccagct gagcagcacc | 1620 |
| atccactgca acacaccaag cctcctgcag ttgcggtcgg ccctcctcca cgctgacttc | 1680 |
| cgggtctcac tctcccacgc ctgtaagaac gctgtgaaga cggatgcccc tgcctctgcc | 1740 |
| ctctggggaca tcatgcgttg ctgggagaag gaatgtccgg tgaaacggga gcgactatca | 1800 |
| gagactagcc cagcgttccg cattctcagt gtggagccca ggctgcaggc caacttcacc | 1860 |
| atccgggaag atgccaaccc cagctcccga cagcgaggac tcaagcgctt ccaggctaac | 1920 |

```
ccggaggcca actggggtcc ccggcctcgt gcccggccag ggggcaaggc ggccgacgaa   1980
gctatggagg agagacgcag gctgcttcag aacaagcgga aggagccgcc ggaagatgtg   2040
gcccagcggg ctgcccggct caagacattt ccttgcaaga ggtttaagga gggcacctgt   2100
caacgcgggg accagtgctg ctactcccac agccccccga cacccagggt ttctgctgat   2160
gctgcccctg actgtccaga gacctccaac cagaccccccc ctggacctgg ggctgccgct   2220
gggccaggca tagactgaac caataaagag atgtcacgtc accttctccc gataaaaaaa   2280
aaaaaaaaaa                                                          2290

<210> SEQ ID NO 21
<211> LENGTH: 1783
<212> TYPE: DNA
<213> ORGANISM: Homo sapiens

<400> SEQUENCE: 21
acttccggtg agcctctggg gcgtaccggc ttggcgcggc ggcagcggca gcggcggctg     60
ggagagcggt cggcggggtt tcttcgttgc attgcctgag aggagcggag tctgccaggt    120
ggtgtccatc atgttctctt tcaacatgtt cgaccaccct attcccaggg tcttccaaaa    180
ccgcttctcc acacagtacc gctgcttctc tgtgtccatg ctagcagggc ctaatgacag    240
gtcagatgtg gagaaaggag ggaagataat tatgccaccc tcggccctgg accaactcag    300
ccgacttaac attacctatc ccatgctgtt caaactgacc aataagaatt cggaccgcat    360
gacgcattgt ggcgtgctgg agtttgtggc tgatgagggc atctgctacc tcccacactg    420
gatgatgcag aacttactct tggaagaagg cggcctggtc caggtggaga gcgtcaacct    480
tcaagtggcc acctactcca aattccaacc tcagagccct gacttcctgg acatcaccaa    540
ccccaaagcc gtattagaaa acgcacttag gaactttgcc tgtctgacca ccggggatgt    600
gattgccatc aactataatg aaaagatcta cgaactgcgt gtgatggaga ccaaccccga    660
caaggcagtg tccatcattg agtgtgacat gaacgtggac tttgatgctc ccctgggcta    720
caaagaaccc gaaagacaag tccagcatga ggagtcgaca gaaggtgaag ccgaccacag    780
tggctatgct ggagagctgg gcttccgcgc tttctctgga tctggcaata gactggatgg    840
aaagaagaaa ggggtagagc ccagcccctc cccaatcaag cctggagata ttaaaagagg    900
aattcccaat tatgaatttta aacttggtaa gataactttc atcagaaatt cacgtccccct    960
tgtcaaaaag gttgaagagg atgaagctgg aggcagattc gtcgctttct ctggagaagg   1020
acagtcattg cgtaaaaagg gaagaaagcc ctaagtgagg actgttggct gattggaaaa   1080
taataaaaga atcatttgca acatcttggc ttttagttac tggcactgac agggacgagc   1140
ctcatcagag aatactctgt tacttaagat ttatttagag ttacctaaga attattaagt   1200
ttgacttgga agtggagcag caggactttg tagttgtatg cttgatttgg ggaaagacaa   1260
agagctgtcc ctgagggcct gtagatagct gcctcctcac ctcttcacgc tttcagcttg   1320
aggggagctc ccactgcctc agcaggagca attctgcatc cctaattctg tcaaaaccta   1380
tgaaggtgac taaattgtct aacatgaagt gttctttctt tttcttcatt tatcctttct   1440
tttcctacat caattgcata ggtgtcagtc tttggcctaa aaaaaggctt taaatagaca   1500
tgtgttctat aagtagtggc tgtcccacta ctgtggctgc aatttaagta tttgacaaag   1560
aatgttctta ttttatttt acatattttt ttcaaaaaca ccactcagaa gaacctgatc   1620
tgaatgagtt tgcacttta ttctcatttc atatggacat aactggctcc ttagtgaacc   1680
```

```
tgttcatagt gaaacaactc catggagaag caaacatgtg aatgttagaa tgaacaaatg      1740
ctaaagagat gttcctctcc ttcttcccta ctccccaact ccc                       1783

<210> SEQ ID NO 22
<211> LENGTH: 2037
<212> TYPE: DNA
<213> ORGANISM: Homo sapiens

<400> SEQUENCE: 22
gggaagctcg ggccggcagg gtttcccgc acgctggcgc ccagctcccg gcgcggaggc        60
cgctgtaagt ttcgctttcc attcagtgga aaacgaaagc tgggcggggt gccacgagcg      120
cggggccaga ccaaggcggg cccggagcgg aacttcggtc ccagctcggt ccccggctca      180
gtcccgacgt ggaactcagc agcggaggct ggacgcttgc atggcgcttg agagattcca      240
tcgtgcctgg ctcacataag cgcttcctgg aagtgaagtc gtgctgtcct gaacgcgggc      300
caggcagctg cggcctgggg gttttggagt gatcacgaat gagcaaggcg tttgggctcc      360
tgaggcaaat ctgtcagtcc atcctggctg agtcctcgca gtccccggca gatcttgaag      420
aaaagaagga agaagacagc aacatgaaga gagagcagcc cagagagcgt cccagggcct      480
gggactaccc tcatggcctg gttggtttac acaacattgg acagacctgc tgccttaact      540
ccttgattca ggtgttcgta atgaatgtgg acttcaccag gatattgaag aggatcacgg      600
tgcccagggg agctgacgag cagaggagaa gcgtcccttt ccagatgctt ctgctgctgg      660
agaagatgca ggacagccgg cagaaagcag tgcggcccct ggagctggcc tactgcctgc      720
agaagtgcaa cgtgcccttg tttgtccaac atgatgctgc ccaactgtac ctcaaactct      780
ggaacctgat taaggaccag atcactgatg tgcacttggt ggagagactg caggccctgt      840
atacgatccg ggtgaaggac tccttgattt gcgttgactg tgccatggag agtagcagaa      900
acagcagcat gctcacccct ccactttctc tttttgatgt ggactcaaag cccctgaaga      960
cactggagga cgccctgcac tgcttcttcc agcccaggga gttatcaagc aaaagcaagt     1020
gcttctgtga gaactgtggg aagaagaccc gtgggaaaca ggtcttgaag ctgacccatt     1080
tgccccagac cctgacaatc cacctcatgc gattctccat caggaattca cagacgagaa     1140
agatctgcca ctccctgtac ttcccccaga gcttggattt cagccagatc cttccaatga     1200
agcgagagtc ttgtgatgct gaggagcagt ctggagggca gtatgagctt tttgctgtga     1260
ttgcgcacgt gggaatggca gactccggtc attactgtgt ctacatccgg aatgctgtgg     1320
atggaaaatg gttctgcttc aatgactcca atatttgctt ggtgtcctgg aagacatcc      1380 agtgtaccta cggaaatcct aactaccact ggcaggaaac tgcatatctt ctggtttaca     1440
tgaagatgga gtgctaatgg aaatgcccaa accttcaga gattgacacg ctgtcatttt      1500
ccatttccgt tcctggatct acggagtctt ctaagagatt ttgcaatgag gagaagcatt     1560
gttttcaaac tatataactg agccttattt ataattaggg atattatcaa aatatgtaac     1620
catgaggccc ctcaggtcct gatcagtcag aatggatgct ttcaccagca gacccggcca     1680
tgtggctgct cggtcctggg tgctcgctgc tgtgcaagac attagcccctt tagttatgag     1740 cctgtgggaa cttcaggggt tcccagtggg gagagcagtg gcagtgggag catctgggg      1800 gccaaaggtc agtggcaggg ggtatttcag tattatacaa ctgctgtgac cagacttgta     1860
tactggctga atatcagtgc tgtttgtaat tttcacttt gagaaccaac attaattcca      1920
tatgaatcaa gtgttttgta actgctattc atttattcag caaatattta ttgatcatct     1980
cttctccata agatagtgtg ataaacacag tcatgaataa agttatttc cacaaaa        2037
```

<210> SEQ ID NO 23
<211> LENGTH: 6696
<212> TYPE: DNA
<213> ORGANISM: Homo sapiens

<400> SEQUENCE: 23

| | | | | | | |
|---|---|---|---|---|---|---|
| atgaggccgc | gctcgggcgg | gcgcccaggg | gccacgggcc | gccgccgccg | ccgcctgcgc | 60 |
| cgccgccccc | gcggcctccg | gtgcagccgc | ctgccgccgc | cgccgccgct | gccgctgctg | 120 |
| ctcgggctgc | tgctggcggc | cgcggggccc | ggcgcggcgc | gggccaagga | gacggcgttc | 180 |
| gtggaggtgg | tgctgttcga | gtcgagccca | agcggcgatt | acaccaccta | caccaccggc | 240 |
| ctcacgggcc | gcttctcgcg | ggccggggcc | acgctcagcg | ccgagggcga | gatcgtgcag | 300 |
| atgcacccac | tgggcctatg | taataacaat | gacgaagagg | acttgtatga | atatggctgg | 360 |
| gtaggagtgg | tgaagctgga | acagccagaa | ttggacccga | accatgcct | cactgtccta | 420 |
| ggcaaggcca | gcgagcagt | acagcgggga | gctactgcag | tcatctttga | tgtgtctgaa | 480 |
| aacccagaag | ctattgatca | gctgaaccag | ggctctgaag | acccgctcaa | gaggccggtg | 540 |
| gtgtatgtga | agggtgcaga | tgccattaag | ctgatgaaca | tcgtcaacaa | gcagaaagtg | 600 |
| gctcgagcaa | ggatccagca | ccgccctcct | cgacaaccca | ctgaatactt | tgacatgggg | 660 |
| attttcctgg | ctttcttcgt | cgtggtctcc | ttggtctgcc | tcatcctcct | tgtcaaaatc | 720 |
| aagctgaagc | agcgacgcag | tcagaattcc | atgaacaggc | tggctgtgca | ggctctagag | 780 |
| aagatggaaa | ccagaaagtt | caactccaag | agcaaggggc | gccgggaggg | gagctgtggg | 840 |
| gccctggaca | cactcagcag | cagctccacg | tccgactgtg | ccatctgtct | ggagaagtac | 900 |
| attgatggag | aggagctgcg | ggtcatcccc | tgtactcacc | ggtttcacag | gaagtgcgtg | 960 |
| gaccctggc | tgctgcagca | ccacacctgc | ccccactgtc | ggcacaacat | catagaacaa | 1020 |
| aagggaaacc | caagcgcggt | gtgtgtggag | accagcaacc | tctcacgtgg | tcggcagcag | 1080 |
| agggtgaccc | tgccggtgca | ttaccccggc | cgcgtgcaca | ggaccaacgc | catcccagcc | 1140 |
| taccctacga | ggacaagcat | ggactccac | ggcaaccccg | tcaccttgct | gaccatggac | 1200 |
| cggcacgggg | agcagagcct | ctattccccg | cagaccccg | cctacatccg | cagctaccca | 1260 |
| cccctccacc | tggaccacag | cctggccgct | caccgctgcg | gcctggagca | ccgggcctac | 1320 |
| tccccagccc | accccttccg | caggcccaag | ttgagtggcc | gcagcttctc | caaggcagct | 1380 |
| tgcttctccc | agtatgagac | catgtaccag | cactactact | ccagggcct | cagctacccg | 1440 |
| gagcaggagg | ggcagtcccc | acctagcctc | gcaccccggg | gccggccg | tgccttcct | 1500 |
| ccgagcggca | gtggcagcct | gctcttcccc | accgtggtgc | acgtggcccc | gccctcccac | 1560 |
| ctggagagcg | gcagcacgtc | cagcttcagc | tgctatcacg | gccaccgctc | ggtgtgcagt | 1620 |
| ggctacctgg | ccgactgccc | aggcagcgac | agcagcagca | gcagcagctc | cggccagtgc | 1680 |
| cactgttcct | ccagtgactc | tgtggtagac | tgcactgagg | tcagcaacca | gggcgtgtac | 1740 |
| gggagctgct | ccaccttccg | cagctccctc | agcagcgact | atgacccctt | catctaccgc | 1800 |
| agccggagcc | cctgtcgtgc | cagtgaggcg | ggggctcgg | gcagctcggg | ccggggacct | 1860 |
| gccctgtgct | tcgagggctc | cccgcctccc | gaggagctcc | cggcggtgca | cagtcatggt | 1920 |
| gctgggcggg | gcgagccttg | gccgggccct | gcctctccct | cggggatca | ggtgtccacc | 1980 |
| tgcagcctgg | agatgaacta | cagcagcaac | tcctccctgg | agcacagggg | gcccaatagc | 2040 |
| tctacctcag | aagtggggct | cgaggcttct | cctgggccg | ccctgacct | caggaggacc | 2100 |

```
tggaagggggg gccacgagtt gccgtcgtgt gcctgctgct gcgagcccca gccctcccca    2160
gccgggccta cgccggagc agctggcagc agcaccttgt tcctggggcc ccacctctac     2220
gagggctctg gcccggcggg tggggagccc cagtcaggaa gctcccaggg cttgtacggc    2280
cttcaccccg accatttgcc caggacagat ggggtgaaat acgagggtct gccctgctgc    2340
ttctatgaag agaagcaggt ggcccgcggg ggcggagggg gcagcggctg ctacactgag    2400
gactactcgg tgagtgtgca gtacacgctc accgaggaac caccgccggg ctgctacccc    2460
ggggcccggg acctgagcca gcgcatcccc atcattccag aggatgtgga ctgtgatctg    2520
ggcctgccct cggactgcca agggacccac agcctcggct cctggggtgg gacgcgaggc    2580
ccggataccc cacggcccca caggggcctg ggagcaaccc gggaagagga gcgggctctg    2640
tgctgccagg ctagggccct actgcggcct ggctgccctc cggaggaggc gggtgctgtc    2700
agggccaact tccctagtgc cctccaggac actcaggagt ccagcaccac tgccactgag    2760
gctgcaggac cgagatctca ctcagcagac agcagcagcc cgggagcctg agctcaggag    2820
gaactcttac ctggaaattg ggaactgtat ggagactcca aactgacttc tttcaaaaaa    2880
caaaaacaaa aaatttttttt agctttgaca acacacaaa agtggtaata aagagagccc    2940
tccttgtcaa cccaaaatgt gagcccctg tggcaaaacc acccctacc ccattaacaa     3000 atcaacagac aaaattctcc gagtcctttg cctcttttga taacatgttg ttctgttttg    3060
taaagtgtgt gtgcttgggg ttccgaggtg tgggattgag ttctctgctt tgttttttt    3120 taagatattg tatgtaaatg taaaaagtta tttaaatata tattttaaag aaccctaact    3180
gccaactttt gctgaaaaag aaaaaaaaat cactgctgca ttaaatgaac cacatcatgt    3240
gtagatactg ttgtctccct gaagggagct caggcctttg aaaagctcag ggcttcacct    3300
gccttagaaa atgaaccaga aacttgaagt aaagctagtt gatagggta caggctctga    3360 ggagcagtgc aaaactgcct cttttctttct cgtggcaaat cccaatgtac acgatttcag   3420
gtctcagacg ccatgcctct ccagcccacg ccttttaggca ggtgatggca gcagctagga   3480
atagggtgta catgatccac agccctgcgg agccaggtca agccgctgct atgaaagctc    3540
cagggtgatg gggacgattc tgcccagtgt cctcagtctg tcccctcagg tcatggtccc    3600
aagtgaaatg acagagttca cagccctggt cttggctgag gtccaggtca tagtaagggc    3660
atgttcttgg ggccctcgac ctgaactctg accctccggg cagggaagag gaggttgtcc    3720
cctttggttg tcctggcttt ggagtccttt gcaaaaatat tttgggcccc ctgccactgg    3780
ctgcagaaat ggctcgacgg ggtgtgtggg gacagacacc cagaaggaat gtacttttgt    3840
ggccttggtg tccgatgggg ctgggggaga gtgctctcca ctgacccagc agcacaccca    3900
tgtgcagtgc gcctgcatct gtgtgggggc agccacaccc cttggctgct gcttccttgg    3960
gctgcctttc tgggggcatg tgactggacc tacgaggtct gcactgagct ccatttgaat    4020 gataccttc ctatcccatt tcccccacgg aagcaccgct tcagggttat tcagtcctct    4080
gcctcatggc tgaaattgct catctcgtct gcagatgtct actatcctgt ctacctaatg    4140
cactattatg tattgattct ccatgagaca gagagagaga gagactatca gatagtttac    4200
acccaaaggg taggttttg tatatttttc cagccttttt tattaagggg aaggggagag    4260
tttaaaaacc caaaccgttg tggttttaag gtgtttcatt tttaaaggg agagagaatc    4320 tatttaaagc tatttcagat cagggattgt catccttttt tgtccaatgt attccttgtt    4380 cttttaaaaaa atttttttta gaggaaacta atattagtct ttgtgttcac taactcttct    4440
ggtcacttgt atttatttat tcattcattc atcagatatt tgttgccatc tgaaagaact    4500
```

-continued

```
ggcccagtgg gtctgaaagc tcgcttgaga ataggaaact tgagacctgg ccccctgtgg    4560
gtaggagaac aaggaccacc tgggttctcc agtcttgaac gagaatctca ctcttatcag    4620 aatgttttc  ttaacctcag cgtatgatga ggaaatttac ttatctctag ctaggatttg    4680
acaaattcca acatcaaatg atcaaaacat ttgccactga ggcttcactg gtgagatccg    4740
ttctccgtcc tcgggtgcag tcccttgggg gctgctcctc ggactgcgcc ccgcacacct    4800
gttatcgagg gtgtgagaag cgcctaagct ggtgacatgt gatctgggac gccttcattt    4860
ctcgggccag gagtagcagc tgctaaggac agcagcttgc attgcgtggt tttagggaag    4920
cagggtctgg cttttaatat gaactgcaaa aagcagcttc tcactgatat ttttttgttg    4980
ttgtttctgg ggggttttttt tgttttgttt ttaatgcctt tgagtgcata ttttcttcct    5040
cgtctgaaac cgaactccca aagtggcttt ctttagccct ggctggaaaa ccacctctca    5100
atagccttaa gcaataaata gatgagtaga gaatgtggct tcaactgggc ttattaaagt    5160
aagtgtgtct agttttcact tgaacaagtg atagctgcag atggcgaaag aaacccattt    5220
aatttttgta gcttacaggt ggtagaaaca aaaatgcaat tttaaaacct taaataccaa    5280
ataccaacca ttgcctttt  ttttttttgag atggaatttt gctcttgtca cccaggctgg    5340
agtgcaatgg cgcgatctca cctcactgca acctctgcct cccgggtcca agtgattctc    5400
ctgcctcagc ctcccaagta gctgggatta caggcatgcg ccaccacacc cagctaattt    5460
tgtatttttg gtagagacag ggtatctcca tgttggtcag gctggtcttg gattcccgac    5520
ctcaggtgat ccgcccacct cggcctccca aagtgctggg attacaggcg tgagccacca    5580
tgcctgccca gcaataccaa ccattgtctt taaattcgt  gttggcttct cagacaggga    5640
gatcactgga ataaaataac cgatggtctt attttgtcac acgtaaatca aagaaatgt    5700 cctctttgaa gttgtaagac tccaccaatg acagacaccc ttttcggtgg actctgagtg    5760
gtgtgtagtg gttttatagc catggaaact aggagtatct cactttccac tgagaacccc    5820
tgcccccaat ccctctaagt tggggtgtgg cagttgggca gggtcaagtg acccagccct    5880
ggctgtagga cagccatata cagtgaagag ttctagaacc agctaaaaat ggaagtttgg    5940
gtgtttacca acaaggtacc tctttatgga tgcagcccca gtaagctggc tttaactctc    6000
agctccttcc ctgtctcctc ctaatccaag ccctttata  aaataaagcc ccttctgtcc    6060
cactgctcac atacttatgt gctgctagtc tctactcgaa gttcgtgcag gactaatgct    6120
tttaaaatga ggtctaaaaa ataattacta gtcgagacta ttattcttta aacagaactg    6180 ccttttcta  ctctttatgt aaactctttc tattgtgttg gtctaacaag gcactatttt    6240 aaaattttt  aattttcccc atagcactta aagagagatt  tgtaaagacc ttgctgtaaa    6300
gattttgtaa taaatggtc  taagggctct ttttccaaca ttaccattt  taaaaaatgt    6360 tttaaaagct agaagacaac ttatgtatat tctgtatatg tatagcagca catttcattt    6420
atggaaatat gttctcagaa tatttattta ctaatatatt tatcttaagc catgtcttat    6480
gttgagagtg tgacattgtt ggaataatca ttgaaaatga ctaacacaag accctgtaaa    6540
tacatgataa ttgcacacag attttacata tttgcagacc aaaatgatt  taaaacaagt    6600 tgtagtcttc tatggttttg taacaaattg tacacatgac tgtaaaaaaa aatacaatt    6660 ttatcaagta tgtgttaaaa aaaaaaaaaa aaaaaa                              6696
```

DETERMINATION OF JAK-STAT1/2 PATHWAY ACTIVITY USING UNIQUE COMBINATION OF TARGET GENES

RELATED APPLICATIONS

This application claims the benefit of European Patent Application No. EP17194291.5, filed Oct. 2, 2017, the entirety of the specification and claims thereof is hereby incorporated by reference for all purposes.

INCORPORATION-BY-REFERENCE OF MATERIAL SUBMITTED ON AS A TEXT FILE VIA THE OFFICE ELECTRONIC FILING SYSTEM (EFS-WEB)

A Sequence Listing associated with this application is provided in text format in lieu of a paper copy, and is hereby incorporated by reference into the specification. The name of the text file containing the Sequence Listing is 2017PF02040_2018-09-25_sequencelisting_ST25.txt. The text file is 83 KB, was created on Sep. 25, 2018, and is being submitted electronically via EFS-Web.

FIELD OF THE INVENTION

The present invention is in the field of systems biology, bioinformatics, genomic mathematical processing and proteomic mathematical processing. In particular, the invention includes a systems-based mathematical process for determining the activity level of a JAK-STAT1/2 cellular signaling pathway in a subject based on expression levels of a unique set of selected target genes in a subject. The invention further provides an apparatus that includes a digital processor configured to perform such a method, a non-transitory storage medium storing instructions that are executable by a digital processing device to perform such a method, and a computer program comprising a program code means for causing a digital processing device to perform such a method. The present invention also includes kits for the determination of expression levels of the unique combinations of target genes.

BACKGROUND OF THE INVENTION

As knowledge of tumors including cancers evolve, it becomes more clear that they are extraordinarily heterogeneous and multifactorial. Tumors and cancers have a wide range of genotypes and phenotypes, they are influenced by their individualized cell receptors (or lack thereof), microenvironment, extracellular matrix, tumor vascularization, neighboring immune cells, and accumulations of mutations, with differing capacities for proliferation, migration, stem cell properties and invasion. This scope of heterogeneity exists even among same classes of tumors. See generally: *Nature* Insight: Tumor Heterogeneity (entire issue of articles), 19 Sep. 2013 (Vol. 501, Issue 7467); Zellmer and Zhang, "Evolving concepts of tumor heterogeneity", *Cell and Bioscience* 2014, 4:69.

Traditionally, physicians have treated tumors, including cancers, as the same within class type (including within receptor type) without taking into account the enormous fundamental individualized nature of the diseased tissue. Patients have been treated with available chemotherapeutic agents based on class and receptor type, and if they do not respond, they are treated with an alternative therapeutic, if it exists. This is an empirical approach to medicine.

There has been a growing trend toward taking into account the heterogeneity of tumors at a more fundamental level as a means to create individualized therapies, however, this trend is still in its formative stages. What is desperately needed are approaches to obtain more metadata about the tumor to inform therapeutic treatment in a manner that allows the prescription of approaches more closely tailored to the individual tumor, and perhaps more importantly, avoiding therapies destined to fail and waste valuable time, which can be life-determinative.

A number of companies and institutions are active in the area of classical, and some more advanced, genetic testing, diagnostics, and predictions for the development of human diseases, including, for example: Affymetrix, Inc.; Bio-Rad, Inc; Roche Diagnostics; Genomic Health, Inc.; Regents of the University of California; Illumina; Fluidigm Corporation; Sequenom, Inc.; High Throughput Genomics; NanoString Technologies; Thermo Fisher; Danaher; Becton, Dickinson and Company; bioMerieux; Johnson & Johnson; Myriad Genetics, and Hologic.

Several companies have developed technology or products directed to gene expression profiling and disease classification. For example, Genomic Health, Inc. is the assignee of numerous patents pertaining to gene expression profiling, for example: U.S. Pat. Nos. 7,081,340; 8,808,994; 8,034,565; 8,206,919; 7,858,304; 8,741,605; 8,765,383; 7,838,224; 8,071,286; 8,148,076; 8,008,003; 8,725,426; 7,888,019; 8,906,625; 8,703,736; 7,695,913; 7,569,345; 8,067,178; 7,056,674; 8,153,379; 8,153,380; 8,153,378; 8,026,060; 8,029,995; 8,198,024; 8,273,537; 8,632,980; 7,723,033; 8,367,345; 8,911,940; 7,939,261; 7,526,637; 8,868,352; 7,930,104; 7,816,084; 7,754,431 and 7,208,470, and their foreign counterparts.

U.S. Pat. No. 9,076,104 to the Regents of the University of California titled "Systems and Methods for Identifying Drug Targets using Biological Networks" claims a method with computer executable instructions by a processor for predicting gene expression profile changes on inhibition of proteins or genes of drug targets on treating a disease, that includes constructing a genetic network using a dynamic Bayesian network based at least in part on knowledge of drug inhibiting effects on a disease, associating a set of parameters with the constructed dynamic Bayesian network, determining the values of a joint probability distribution via an automatic procedure, deriving a mean dynamic Bayesian network with averaged parameters and calculating a quantitative prediction based at least in part on the mean dynamic Bayesian network, wherein the method searches for an optimal combination of drug targets whose perturbed gene expression profiles are most similar to healthy cells.

Affymetrix has developed a number of products related to gene expression profiling. Non-limiting examples of U.S. patents to Affymetrix include: U.S. Pat. Nos. 6,884,578; 8,029,997; 6,308,170; 6,720,149; 5,874,219; 6,171,798; and 6,391,550.

Likewise, Bio-Rad has a number of products directed to gene expression profiling. Illustrative examples of U.S. patents to Bio-Rad include: U.S. Pat. Nos. 8,021,894; 8,451,450; 8,518,639; 6,004,761; 6,146,897; 7,299,134; 7,160,734; 6,675,104; 6,844,165; 6,225,047; 7,754,861 and 6,004,761.

Koninklijke Philips N.V. (NL) has filed a number of patent applications in the general area of assessment of cellular signaling pathway activity using various mathematical models, including U.S. Ser. No. 14/233,546 (WO 2013/011479), titled "Assessment of Cellular Signaling Pathway Using Probabilistic Modeling of Target Gene Expression";

U.S. Ser. No. 14/652,805 (WO 2014/102668) titled "Assessment of Cellular Signaling Pathway Activity Using Linear Combinations of Target Gene Expressions"; WO 2014/174003 titled "Medical Prognosis and Prediction of Treatment Response Using Multiple Cellular Signaling Pathway Activities"; and WO 2015/101635 titled "Assessment of the PI3K Cellular Signaling Pathway Activity Using Mathematical Modeling of Target Gene Expression".

Despite this progress, more work is needed to definitively characterize tumor cellular behavior. In particular, there is a critical need to determine which pathways have become pathogenic to the cell. However, it is difficult to identify and separate abnormal cellular signaling from normal cellular pathway activity.

STAT1 and STAT2 are inducible transcription factors that regulate the expression of many genes involved in the immune response and in cancer. The JAK-STAT1/2 cellular signaling pathway is a key signaling pathway involved in diverse challenges faced by the immune system, from resisting infection to maintaining immune tolerance, enforcing barrier functions and guarding against cancer. Different stimuli, such as IFNs, trigger the JAK-STAT1/2 cellular signaling pathway to phosphorylate latent, cytosolic STAT monomers, allowing them to form STAT1 homo and STAT1/2 heterodimers, which in turn bind to specific DNA target sites and regulate the transcription of genes. The type I interferons typically activate a STAT1/2 heterodimer as transcription factor, while type II interferons activate predominantly STAT1/1 homodimers. Both transcription factor complexes activate target gene transcription through a separately defined response element, named ISRE and GAS, respectively (see also FIG. 1, which is based on Platanias L. C., "Mechanisms of type-I- and type-II-interferon-mediated signaling", Nature Reviews Immunology, Vol. 5, May 2015, pages 375 to 386). For this reason, it is preferred to have models which can distinguish between STAT1/2 and STAT1/1 transcription, although their target genes in general are likely to be overlapping and it is not completely clear which target genes are specific for the one or the other of the transcription complexes.

With respect to the JAK-STAT1/2 signaling in e.g. cancer, it is important to be able to detect abnormal JAK-STAT1/2 signaling activity in order to enable the right choice of targeted drug treatment. Currently anti-JAK-STAT1/2 therapies are being developed (see Liu B. et al., "Inhibition of Stat1-mediated gene activation by PIAS1", Cell Biology, Vol. 95, September 1998, pages 10626 to 10631). However, today there is no clinical assay available to assess the functional state resp. activity of the JAK-STAT1/2 cellular signaling pathway, which in its active state indicates that it is, for instance, more likely to be tumor-promoting compared to its passive state. It is therefore desirable to be able to improve the possibilities of characterizing patients that have a disease, such as a cancer, e.g., a breast, cervical, endometrial, ovarian, pancreatic or prostate cancer, or an immune disorder, which is at least partially driven by an abnormal activity of the JAK-STAT1/2 cellular signaling pathway, and that are therefore likely to respond to inhibitors of the JAK-STAT1/2 cellular signaling pathway.

It is therefore an object of the invention to provide a more accurate process to determine the tumorigenic propensity of the JAK-STAT1/2 cellular signaling pathway in a cell, as well as associated methods of therapeutic treatment, kits, systems, etc.

SUMMARY OF THE INVENTION

The present invention includes methods and apparatuses for determining the activity level of a JAK-STAT1/2 cellular signaling pathway in a subject, typically a human with diseased tissue such as a tumor or cancer, wherein the activity level of the JAK-STAT1/2 cellular signaling pathway is determined by calculating an activity level of a JAK-STAT1/2 transcription factor element in a sample of the involved tissue isolated from the subject, wherein the activity level of the JAK-STAT1/2 transcription factor element in the sample is associated with JAK-STAT1/2 cellular signaling, wherein the activity level of the JAK-STAT1/2 transcription factor element in the sample is determined by measuring the expression levels of a unique set of target genes controlled by the JAK-STAT1/2 transcription factor element using a calibrated pathway model that compares the expression levels of the target genes in the sample with expression levels of the target genes in the calibrated pathway model.

In particular, the unique set of target genes whose expression level is analyzed in the calibrated pathway model includes at least three target genes, at least four target genes, at least five target genes, at least six target genes, at least seven target genes, at least eight target genes, at least nine target genes, at least ten target genes or more selected from BID, GNAZ, IRF1, IRF7, IRF8, IRF9, LGALS1, NCF4, NFAM1, OAS1, PDCD1, RAB36, RBX1, RFPL3, SAMM50, SMARCB1, SSTR3, ST13, STAT1, TRMT1, UFD1L, USP18, and ZNRF3. In one embodiment, the unique set of target genes whose expression level is analyzed in the calibrated pathway model comprises at least three target genes, at least four target genes, at least five target genes, at least six target genes, at least seven target genes, at least eight target genes or more selected from IRF1, IRF7, IRF8, IRF9, OAS1, PDCD1, ST13, STAT1, and USP18. In one embodiment, the activity level of the JAK-STAT1/2 cellular signaling pathway is determined to be either IFN type I activity or IFN type II activity by using two calibrated pathway models of which one is calibrated on IFN type I activity and the other is calibrated on IFN type II activity. The determining preferably comprises a comparison of the determined activity levels. For instance, if the JAK-STAT1/2 IFN type I model reports an active pathway, and the JAK-STAT1/2 IFN type II model does not or reports a lower activity level than the JAK-STAT1/2 IFN type I model, the sample may be concluded to be IFN type I activated JAK-STAT1/2. On the other hand, if the JAK-STAT1/2 IFN type II model reports an active pathway, and the JAK-STAT1/2 IFN type I model does not or reports a lower activity level, IFN type II activated JAK-STAT1/2 may be concluded. Alternatively, a difference in activity level between both models may be calculated, and instead of determining whether the difference is positive or negative, one may compare it to a threshold other than zero.

Using this invention, health care providers will be able to more accurately assess the functional state of the JAK-STAT1/2 cellular signaling pathway at specific points in disease progression. Without being bound by any particular theory, it is believed that the identified target genes of the present invention in combination with the analytical methods described herein reduces the noise associated with the use of large subsets of target genes as previously described in the literature. Furthermore, as described and exemplified below, the use of specific combinations of select target genes allows for the precise determination of cellular signaling activity, and allows for an increased accuracy in the determination of disease state and prognosis. Accordingly, such cellular signaling pathway status can be used to, for example but not limited to, identify the presence or absence of disease and/or particular disease state or advancement, identify the presence or absence of a disorder or disease state, identify a particular subtype within a disease or disorder based one the activity level of the JAK-STAT1/2 cellular signaling pathway, derive a course of treatment based on the presence or absence of JAK-STAT1/2 signaling activity for example by administering a JAK-STAT1/2 inhibitor, and/or monitor disease progression in order to, for example, adjust therapeutic protocols based on a predicted drug efficacy in light of the determined activity level of the JAK-STAT1/2 cellular signaling pathway in the sample.

The term "JAK-STAT1/2 transcriptional factor element" or "JAK-STAT1/2 TF element" or "TF element" refers to a protein complex containing at least a STAT1-STAT2 heterodimer or a STAT1 homodimer, which is capable of binding to specific DNA sequences, preferably the ISRE (binding motif AGTTTCNNTTCNC/T) or GAS (binding motif TTC/ANNNG/TAA) response elements, respectively, thereby controlling transcription of target genes. Preferably, the term refers to either a protein or protein complex transcriptional factor that is formed by different stimuli such as IFNs triggered by the binding of the stimulating ligand to its receptor resulting in downstream signaling.

The present invention is based on the realization of the inventors that a suitable way of identifying effects occurring in the JAK-STAT1/2 cellular signaling pathway can be based on a measurement of the signaling output of the JAK-STAT1/2 cellular signaling pathway, which is—amongst others—the transcription of the unique target genes described herein by a JAK-STAT1/2 transcription factor (TF) element controlled by the JAK-STAT1/2 cellular signaling pathway. This realization by the inventors assumes that the TF level is at a quasi-steady state in the sample which can be detected by means of—amongst others—the expression values of the target genes. The JAK-STAT1/2 cellular signaling pathway targeted herein is known to control many functions in many cell types in humans, such as proliferation, differentiation and wound healing. Regarding pathological disorders, such as cancer (e.g., breast, cervical, endometrial, ovarian, pancreatic or prostate cancer), the abnormal JAK-STAT1/2 cellular signaling activity plays an important role, which is detectable in the expression profiles of the target genes and thus exploited by means of a calibrated mathematical pathway model.

The present invention makes it possible to determine the activity level of the JAK-STAT1/2 cellular signaling pathway in a subject by (i) determining an activity level of a JAK-STAT1/2 TF element in a sample isolated from the subject, wherein the determining is based at least in part on evaluating a calibrated pathway model relating expression levels of at least three target genes of the JAK-STAT1/2 cellular signaling pathway, the transcription of which is controlled by the JAK-STAT1/2 TF element, to the activity level of the JAK-STAT1/2 TF element, and by (ii) calculating the activity level of the JAK-STAT1/2 cellular signaling pathway in the sample based on the calculated activity level of the JAK-STAT1/2 TF element in the sample. This preferably allows improving the possibilities of characterizing patients that have a disease, such as cancer, e.g., a breast, cervical, endometrial, ovarian, pancreatic or prostate cancer, which is at least partially driven by an abnormal activity of the JAK-STAT1/2 cellular signaling pathway, and that are therefore likely to respond to inhibitors of the JAK-STAT1/2 cellular signaling pathway. In particular embodiments, treatment determination can be based on specific JAK-STAT1/2 activity. In a particular embodiment the JAK-STAT1/2 cellular signaling status can be set at a cutoff value of odds of the JAK-STAT1/2 cellular signaling pathway being activate of, for example, 10:1, 5:1, 4:1, 2:1, 1:1, 1:2, 1:4, 1:5, or 1:10.

In one aspect of the invention, provided herein is a computer implemented method for determining the activity level of a JAK-STAT1/2 cellular signaling pathway in a subject performed by computerized device having a processor comprising:

a. calculating an activity level of a JAK-STAT1/2 transcription factor element in a sample isolated from the subject, wherein the activity level of the JAK-STAT1/2 transcription factor element in the sample is associated with JAK-STAT1/2 cellular signaling, and wherein the activity level of the JAK-STAT1/2 transcription factor element in the sample is calculated by:

i. receiving data on the expression levels of at least, for example, at least four, at least five, at least six, at least seven, at least eight, at least nine, at least ten or more target genes derived from the sample, wherein the JAK-STAT1/2 transcription factor element controls transcription of the at least three target genes, and wherein the at least three target genes are selected from BID, GNAZ, IRF1, IRF7, IRF8, IRF9, LGALS1, NCF4, NFAM1, OAS1, PDCD1, RAB36, RBX1, RFPL3, SAMM50, SMARCB1, SSTR3, ST13, STAT1, TRMT1, UFD1L, USP18, and ZNRF3;

ii. calculating the activity level of the JAK-STAT1/2 transcription factor element in the sample using a calibrated pathway model, wherein the calibrated pathway model compares the expression levels of the at least three target genes in the sample with expression levels of the at least three target genes in the calibrated pathway model which define an activity level of the JAK-STAT1/2 transcription factor element; and, b. calculating the activity level of the JAK-STAT1/2 cellular signaling pathway in the sample based on the calculated activity level of the JAK-STAT1/2 transcription factor element in the sample.

In one embodiment, the at least three, for example, at least four, at least five, at least six, at least seven, at least eight or more target genes are selected from IRF1, IRF7, IRF8, IRF9, OAS1, PDCD1, ST13, STAT1, and USP18. In one embodiment, the activity level of the JAK-STAT1/2 cellular signaling pathway is determined to be either IFN type I activity or IFN type II activity by using two calibrated pathway models of which one is calibrated on IFN type I activity and the other is calibrated on IFN type II activity. In one embodiment, the method further comprises assigning a JAK-STAT1/2 cellular signaling pathway activity status to the calculated activity level of the JAK-STAT1/2 cellular signaling pathway in the sample wherein the activity status is indicative of either an active JAK-STAT1/2 cellular signaling pathway or a passive JAK-STAT1/2 cellular signaling pathway. In one embodiment, the activity status of the JAK-STAT1/2 cellular signaling pathway is established by establishing a specific threshold for activity as described further below. In one embodiment, the threshold is set as a probability that the cellular signaling pathway is active, for example, a 10:1, 5:1, 4:1, 3:1, 2:1, 1:1, 1:2, 1:4, 1:5, or 1:10. In one embodiment, the activity status is based, for example, on a minimum calculated activity. In one embodiment, the method further comprises assigning to the calculated JAK-STAT1/2 cellular signaling in the sample a probability that the JAK-STAT1/2 cellular signaling pathway is active.

As contemplated herein, the activity level of the JAK-STAT1/2 transcription factor element is determined using a calibrated pathway model executed by one or more computer processors, as further described below. The calibrated pathway model compares the expression levels of the at least three target genes in the sample with expression levels of the at least three target genes in the calibrated pathway model which define an activity level of the JAK-STAT1/2 transcription factor element. In one embodiment, the calibrated pathway model is a probabilistic model incorporating conditional probabilistic relationships that compare the expression levels of the at least three target genes in the sample with expression levels of the at least three target genes in the calibrated pathway model which define a level of a JAK-STAT1/2 transcription factor element to determine the activity level of the JAK-STAT1/2 transcription factor element in the sample. In one embodiment, the probabilistic model is a Bayesian network model. In an alternative embodiment, the calibrated pathway model can be a linear or pseudo-linear model. In an embodiment, the linear or pseudo-linear model is a linear or pseudo-linear combination model.

As contemplated herein, the expression levels of the unique set of target genes can be determined using standard methods known in the art. For example, the expression levels of the target genes can be determined by measuring the level of mRNA of the target genes, through quantitative reverse transcriptase-polymerase chain reaction techniques, using probes associated with a mRNA sequence of the target genes, using a DNA or RNA microarray, and/or by measuring the protein level of the protein encoded by the target genes. Once the expression level of the target genes is determined, the expression levels of the target genes within the sample can be utilized in the calibrated pathway model in a raw state or, alternatively, following normalization of the expression level data. For example, expression level data can be normalized by transforming it into continuous data, z-score data, discrete data, or fuzzy data.

As contemplated herein, the calculation of JAK-STAT1/2 signaling in the sample is performed on a computerized device having a processor capable of executing a readable program code for calculating the JAK-STAT1/2 signaling in the sample according to the methods described above. Accordingly, the computerized device can include means for receiving expression level data, wherein the data is expression levels of at least three target genes derived from the sample, a means for calculating the activity level of a JAK-STAT1/2 transcription factor element in the sample using a calibrated pathway model, wherein the calibrated pathway model compares the expression levels of the at least three target genes in the sample with expression levels of the at least three target genes in the calibrated pathway model which define an activity level of the JAK-STAT1/2 transcription factor element; a means for calculating the JAK-STAT1/2 cellular signaling in the sample based on the calculated activity level of a JAK-STAT1/2 transcription factor element in the sample; and a means for assigning a JAK-STAT1/2 cellular signaling pathway activity probability or status to the calculated JAK-STAT1/2 cellular signaling in the sample, and, optionally, a means for displaying the JAK-STAT1/2 signaling pathway activity probability or status.

In accordance with another disclosed aspect, further provided herein is a non-transitory storage medium capable of storing instructions that are executable by a digital processing device to perform the method according to the present invention as described herein. The non-transitory storage medium may be a computer-readable storage medium, such as a hard drive or other magnetic storage medium, an optical disk or other optical storage medium, a random access memory (RAM), read only memory (ROM), flash memory, or other electronic storage medium, a network server, or so forth. The digital processing device may be a handheld device (e.g., a personal data assistant or smartphone), a notebook computer, a desktop computer, a tablet computer or device, a remote network server, or so forth.

Further contemplated herein are methods of treating a subject having a disease or disorder associated with an activated JAK-STAT1/2 cellular signaling pathway, or a disorder whose advancement or progression is exacerbated or caused by, whether partially or wholly, an activated JAK-STAT1/2 cellular signaling pathway, wherein the determination of the JAK-STAT1/2 cellular signaling pathway activity is based on the methods described above, and administering to the subject a JAK-STAT1/2 inhibitor if the information regarding the activity level of JAK-STAT1/2 cellular signaling pathway is indicative of an active JAK-STAT1/2 cellular signaling pathway. In one embodiment, the subject is suffering from a cancer, for example, a breast cancer, a cervical cancer, an endometrial cancer, an ovarian cancer, a pancreatic cancer, or a prostate cancer, or an immune disorder. In a more particular embodiment, the cancer is a breast cancer.

Also contemplated herein is a kit for measuring the expression levels of at least six, for example, at least seven, at least eight, at least nine, at least ten or more JAK-STAT1/2 cellular signaling pathway target genes, as described herein. In one embodiment, the kit includes one or more components, for example probes, for example labeled probes, and/or PCR primers, for measuring the expression levels of at least six, for example, at least seven, at least eight, at least nine, at least ten or more target genes selected from BID, GNAZ, IRF1, IRF7, IRF8, IRF9, LGALS1, NCF4, NFAM1, OAS1, PDCD1, RAB36, RBX1, RFPL3, SAMM50, SMARCB1, SSTR3, ST13, STAT1, TRMT1, UFD1L, USP18. In one embodiment, the kit includes one or more components for measuring the expression levels of at least six, for example, at least seven, at least eight or more target genes selected from IRF1, IRF7, IRF8, IRF9, OAS1, PDCD1, ST13, STAT1, and USP18.

As contemplated herein, the one or more components or means for measuring the expression levels of the particular target genes can be selected from the group consisting of: an DNA array chip, an oligonucleotide array chip, a protein array chip, an antibody, a plurality of probes, for example, labeled probes, a set of RNA reverser-transcriptase sequencing components, and/or RNA or DNA, including cDNA, amplification primers. In one embodiment, the kit includes a set of labeled probes directed to a portion of an mRNA or cDNA sequence of the targeted genes as described herein. In one embodiment, the kit includes a set of primers and probes directed to a portion of an mRNA or cDNA sequence of the targeted genes as described herein. In one embodiment, the labeled probes are contained in a standardized 96-well plate. In one embodiment, the kit further includes primers or probes directed to a set of reference genes. Such reference genes can be, for example, constitutively expressed genes useful in normalizing or standardizing expression levels of the target gene expression levels described herein.

In one embodiment, the kit further includes a non-transitory storage medium containing instructions that are executable by a digital processing device to perform a method according to the present invention as described herein. In one embodiment, the kit includes an identification code that provides access to a server or computer network for analyzing the activity level of the JAK-STAT1/2 cellular signaling pathway based on the expression levels of the target genes and the methods described herein.

DETAILED DESCRIPTION OF THE INVENTION

Figure 1:
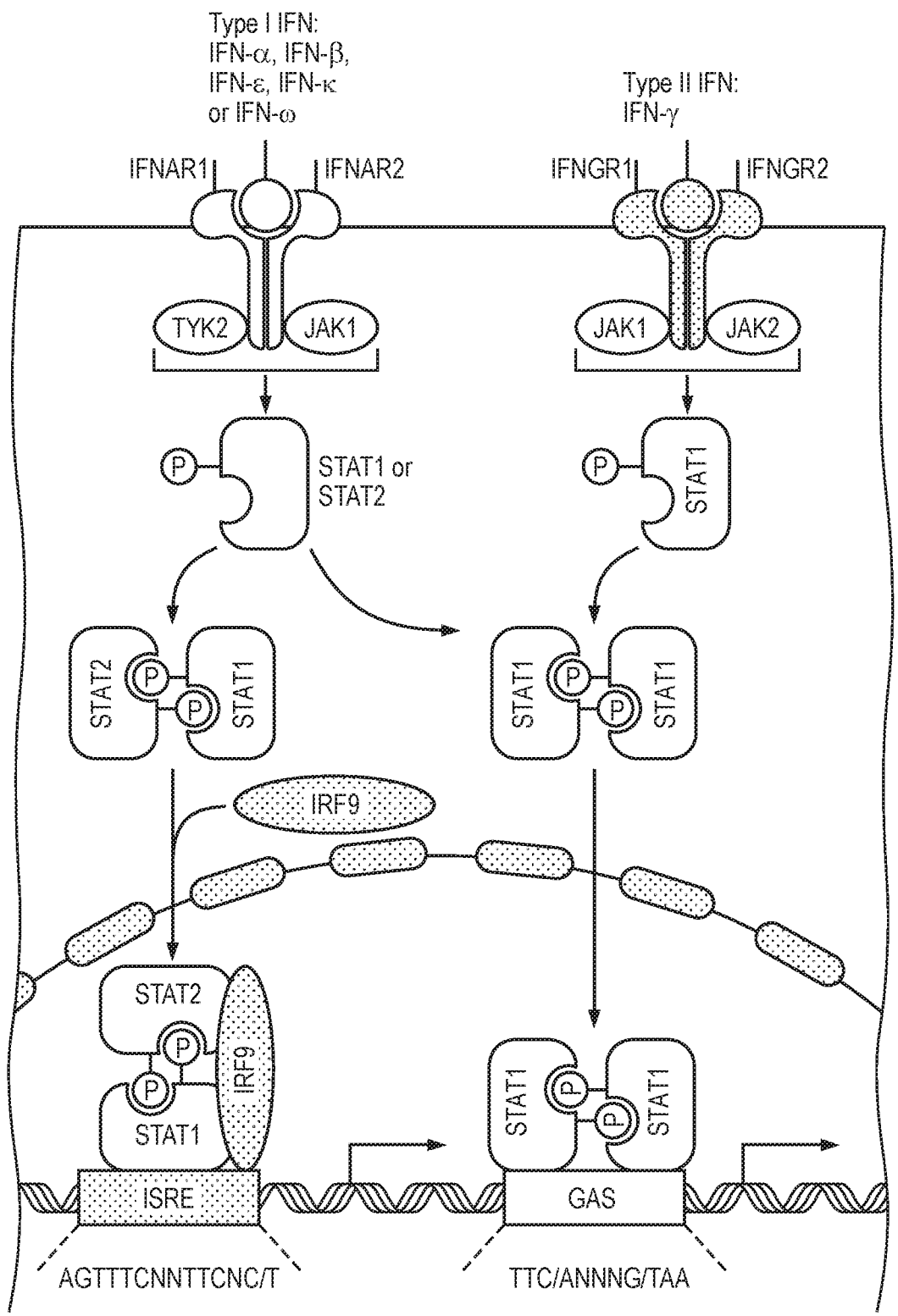
FIG. 1 shows schematically and exemplarily the JAK-STAT1/2 cellular signaling pathway. Different stimuli, such as IFNs, trigger the JAK-STAT1/2 pathway to phosphorylate latent, cytosolic STAT monomers, allowing them to form STAT1 homo and STAT1/2 heterodimers, which in turn bind to specific DNA target sites and regulate the transcription of genes. The type I interferons typically activate a STAT1/2 heterodimer as transcription factor, while type II interferons activate predominantly STAT1/1 homodimers. Both transcription factor complexes active target gene transcription through a separately defined response element, named ISRE and GAS, respectively (see also FIG. 1, which is based on Platanias L. C., "Mechanisms of type-I- and type-II-interferon-mediated signaling", Nature Reviews Immunology, Vol. 5, May 2015, pages 375 to 386).

Provided herein are methods and apparatuses, and in particular computer implemented methods and apparatuses, for determining the activity level of a JAK-STAT1/2 cellular signaling pathway in a subject, wherein the activity level of the JAK-STAT1/2 cellular signaling pathway is calculated by a) calculating an activity level of a JAK-STAT1/2 transcription factor element in a sample isolated from a subject, wherein the activity level of the JAK-STAT1/2 transcription factor element in the sample is associated with JAK-STAT1/2 cellular signaling, and wherein the activity level of the JAK-STAT1/2 transcription factor element in the sample is calculated by measuring the expression levels of a unique set of target genes, wherein the JAK-STAT1/2 transcription factor element controls transcription of the target genes, calculating the activity level of the JAK-STAT1/2 transcription factor element in the sample using a calibrated pathway model, wherein the calibrated pathway model compares the expression levels of the target genes in the sample with expression levels of the target genes in the calibrated pathway model which define an activity level of the JAK-STAT1/2 transcription factor element; and calculating the activity level of the JAK-STAT1/2 cellular signaling pathway in the sample based on the calculated activity level of the JAK-STAT1/2 transcription factor element in the sample.

In particular, the unique set of target genes whose expression levels is analyzed in the calibrated pathway model includes at least three, for example, at least four, at least five, at least six, at least seven, at least eight, at least nine, at least ten or more target genes selected from BID, GNAZ, IRF1, IRF7, IRF8, IRF9, LGALS1, NCF4, NFAM1, OAS1, PDCD1, RAB36, RBX1, RFPL3, SAMM50, SMARCB1, SSTR3, ST13, STAT1, TRMT1, UFD1L, USP18, and ZNRF3. It has been discovered that analyzing a specific set of target genes as described herein in the disclosed pathway model provides for an advantageously accurate JAK-STAT1/2 cellular signaling pathway activity determination. Accordingly, such status can be used to, for example but not limited to, identify the presence or absence of disease and/or particular disease state or advancement, diagnose a specific disease or disease state, or diagnose the presence or absence of a particular disease, derive a course of treatment based on the presence or absence of JAK-STAT1/2 signaling activity, monitor disease progression in order to, for example, adjust therapeutic protocols based on a predicted drug efficacy in light of the determined activity of the JAK-STAT1/2 signaling pathway in the sample, or develop JAK-STAT1/2 targeted therapeutics.

Definitions

All terms used herein are intended to have their plain and ordinary meaning as normally ascribed in the art unless otherwise specifically indicated herein.

Herein, the "level" of a TF element denotes the level of activity of the TF element regarding transcription of its target genes.

The term "subject" or "host", as used herein, refers to any living being. In some embodiments, the subject is an animal, for example a mammal, including a human. In a particular embodiment, the subject is a human. In one embodiment, the human is suspected of having a disorder mediated or exacerbated by an active JAK-STAT1/2 cellular signaling pathway, for example, a cancer. In one embodiment, the human has or is suspected of having a breast cancer.

The term "sample", as used herein, means any biological specimen isolated from a subject. Accordingly, "sample" as used herein is contemplated to encompasses the case where e.g. a tissue and/or cells and/or a body fluid of the subject have been isolated from the subject. Performing the claimed method may include where a portion of this sample is extracted, e.g., by means of Laser Capture Microdissection (LCM), or by scraping off the cells of interest from the slide, or by fluorescence-activated cell sorting techniques. In addition, the term "sample", as used herein, also encompasses the case where e.g. a tissue and/or cells and/or a body fluid of the subject has been taken from the subject and has been put on a microscope slide, and the claimed method is performed on the slide. In addition, the term "samples," as used herein, may also encompass circulating tumor cells or CTCs.

The term "JAK-STAT1/2 transcriptional factor element" or "JAK-STAT1/2 TF element" or "TF element" refers to a protein complex containing at least a STAT1-STAT2 heterodimer or a STAT1 homodimer, which is capable of binding to specific DNA sequences, preferably the ISRE (binding motif AGTTTCNNTTCNC/T) or GAS (binding motif TTC/ANNNG/TAA) response elements, respectively, thereby controlling transcription of target genes. Preferably, the term refers to either a protein or protein complex transcriptional factor that is formed by different stimuli such as IFNs triggered by the binding of the stimulating ligand to its receptor resulting in downstream signaling.

The term "target gene" as used herein, means a gene whose transcription is directly or indirectly controlled by a JAK-STAT1/2 transcription factor element. The "target gene" may be a "direct target gene" and/or an "indirect target gene" (as described herein).

As contemplated herein, target genes include at least BID, GNAZ, IRF1, IRF7, IRF8, IRF9, LGALS1, NCF4, NFAM1, OAS1, PDCD1, RAB36, RBX1, RFPL3, SAMM50, SMARCB1, SSTR3, ST13, STAT1, TRMT1, UFD1L, USP18, and ZNRF3.

As contemplated herein, the present invention includes:
A) A computer implemented method for determining the activity level of a JAK-STAT1/2 cellular signaling pathway in a subject performed by a computerized device having a processor comprising:
  a. calculating an activity level of a JAK-STAT1/2 transcription factor element in a sample isolated from the subject, wherein the activity level of the JAK-STAT1/2 transcription factor element in the sample is associated with JAK-STAT1/2 cellular signaling, and wherein the activity level of the JAK-STAT1/2 transcription factor element in the sample is calculated by:
    i. receiving data on the expression levels of at least three, for example, at least five, at least six, at least seven, at least eight, at least nive, at least ten or more target genes derived from the sample, wherein the JAK-STAT1/2 transcription factor element controls transcription of the at least three target genes, and wherein the at least three target genes are selected from BID, GNAZ, IRF1, IRF7, IRF8, IRF9, LGALS1, NCF4, NFAM1, OAS1, PDCD1, RAB36, RBX1, RFPL3, SAMM50, SMARCB1, SSTR3, ST13, STAT1, TRMT1, UFD1L, USP18, and ZNRF3;
    ii. calculating the activity level of the JAK-STAT1/2 transcription factor element in the sample using a calibrated pathway model, wherein the calibrated pathway model compares the expression levels of the at least three target genes in the sample with expression levels of the at least three target genes in the calibrated pathway model which define an activity level of the JAK-STAT1/2 transcription factor element; and,
  b. calculating the activity level of the JAK-STAT1/2 cellular signaling pathway in the sample based on the calculated activity level of the JAK-STAT1/2 transcription factor element in the sample.

In one embodiment, the at least three, for example, at least four, at least five, at least six, at least seven, at least eight or more target genes are selected from IRF1, IRF7, IRF8, IRF9, OAS1, PDCD1, ST13, STAT1, and USP18. In one embodiment, the activity level of the JAK-STAT1/2 cellular signaling pathway is determined to be either IFN type I activity or IFN type II activity by using two calibrated pathway models of which one is calibrated on IFN type I activity and the other is calibrated on IFN type II activity. In one embodiment, the method further comprises assigning a JAK-STAT1/2 cellular signaling pathway activity status to the calculated activity level of the JAK-STAT1/2 cellular signaling in the sample, wherein the activity status is indicative of either an active JAK-STAT1/2 cellular signaling pathway or a passive JAK-STAT1/2 cellular signaling pathway. In one embodiment, the method further comprises displaying the JAK-STAT1/2 cellular signaling pathway activity status. In one embodiment, the calibrated pathway model is a probabilistic model incorporating conditional probabilistic relationships that compare the expression levels of the at least three target genes in the sample with expression levels of the at least three target genes in the calibrated pathway model which define a level of the JAK-STAT1/2 transcription factor element to determine the activity level of the JAK-STAT1/2 transcription factor element in the sample. In one embodiment, the probabilistic model is a Bayesian network model. In one embodiment, the calibrated pathway model is a linear model incorporating relationships that compare the expression levels of the at least three target genes in the sample with expression levels of the at least three target genes in the calibrated pathway model which define a level of JAK-STAT1/2 transcription factor element to determine the activity level of the JAK-STAT1/2 transcription factor element in the sample.

B) A computer program product for determining the activity level of a JAK-STAT1/2 cellular signaling pathway in a subject comprising:
 a. a non-transitory computer readable storage medium having computer readable program code embodied therewith, the computer readable program code executable by at least one processor to:
  i. calculate an activity level of a JAK-STAT1/2 transcription factor element in a sample isolated from a subject, wherein the activity level of the JAK-STAT1/2 transcription factor element in the sample is associated with JAK-STAT1/2 cellular signaling, and wherein the activity level of the JAK-STAT1/2 transcription factor element in the sample is calculated by:
   1. receiving data on the expression levels of at least three, for example, at least four, at least five, at least six, at least seven, at least eight, at least nine, at least ten or more target genes derived from the sample, wherein the at least three target genes are selected from BID, GNAZ, IRF1, IRF7, IRF8, IRF9, LGALS1, NCF4, NFAM1, OAS1, PDCD1, RAB36, RBX1, RFPL3, SAMM50, SMARCB1, SSTR3, ST13, STAT1, TRMT1, UFD1L, USP18, and ZNRF3;
   2. calculating the activity level of the JAK-STAT1/2 transcription factor element in the sample using a calibrated pathway model, wherein the calibrated pathway model compares the expression levels of the at least three target genes in the sample with expression levels of the at least three target genes in the calibrated pathway model which define an activity level of JAK-STAT1/2 transcription factor element; and,
 b. calculate the activity level of the JAK-STAT1/2 cellular signaling pathway in the sample based on the calculated activity level of the JAK-STAT1/2 transcription factor element in the sample.

In one embodiment, the at least three, for example, at least four, at least five, at least six, at least seven, at least eight or more target genes are selected from IRF1, IRF7, IRF8, IRF9, OAS1, PDCD1, ST13, STAT1, and USP18. In one embodiment, the activity level of the JAK-STAT1/2 cellular signaling pathway is determined to be either IFN type I activity or IFN type II activity by using two calibrated pathway models of which one is calibrated on IFN type I activity and the other is calibrated on IFN type II activity. In one embodiment, the computer readable program code is executable by at least one processor to assign a JAK-STAT1/2 cellular signaling pathway activity status to the calculated activity level of the JAK-STAT1/2 cellular signaling in the sample, wherein the activity status is indicative of either an active JAK-STAT1/2 cellular signaling pathway or a passive JAK-STAT1/2 cellular signaling pathway. In one embodiment, the computer readable program code is executable by at least one processor to display the JAK-STAT1/2 signaling pathway activity status. In one embodiment, the calibrated pathway model is a probabilistic model incorporating conditional probabilistic relationships that compare the expression levels of the at least three target genes in the sample with expression levels of the at least three target genes in the calibrated pathway model which define a level of JAK-STAT1/2 transcription factor element to determine the activity level of JAK-STAT1/2 transcription factor element in the sample. In one embodiment, the probabilistic model is a Bayesian network model. In one embodiment, the calibrated pathway model is a linear model incorporating relationships that compare the expression levels of the at least three target genes in the sample with expression levels of the at least three target genes in the calibrated pathway model which define a level of a JAK-STAT1/2 transcription factor element to determine the activity level of the JAK-STAT1/2 transcription factor element in the sample.

C) A method of treating a subject suffering from a disease associated with an activated JAK-STAT1/2 cellular signaling pathway comprising:
 a. receiving information regarding the activity level of a JAK-STAT1/2 cellular signaling pathway derived from a sample isolated from the subject, wherein the activity level of the JAK-STAT1/2 cellular signaling pathway is determined by:
  i. calculating an activity level of a JAK-STAT1/2 transcription factor element in a sample isolated from the subject, wherein the activity level of the JAK-STAT1/2 transcription factor element in the sample is associated with JAK-STAT1/2 cellular signaling, and wherein the level of the JAK-STAT1/2 transcription factor element in the sample is calculated by:
   1. receiving data on the expression levels of at least three, for example, at least four, at least five, at least six, at least seven, at least eight, at least nine, at least ten or more target genes derived from the sample, wherein the JAK-STAT1/2 transcription factor element controls transcription of the at least three target genes, and wherein the at least three target genes are selected from BID, GNAZ, IRF1, IRF7, IRF8, IRF9, LGALS1, NCF4, NFAM1, OAS1, PDCD1, RAB36, RBX1, RFPL3, SAMM50, SMARCB1, SSTR3, ST13, STAT1, TRMT1, UFD1L, USP18, and ZNRF3;
   2. calculating the activity level of the JAK-STAT1/2 transcription factor element in the sample using a calibrated pathway model, wherein the calibrated pathway model compares the expression levels of the at least three target genes in the sample with expression levels of the at least three target genes in the calibrated pathway model which define an activity level of the JAK-STAT1/2 transcription factor element; and,
  ii. calculating the activity level of the JAK-STAT1/2 cellular signaling pathway in the sample based on the calculated activity level of the JAK-STAT1/2 transcription factor element in the sample; and,
 b. administering to the subject a JAK-STAT1/2 inhibitor if the information regarding the activity level of the JAK-STAT1/2 cellular signaling pathway is indicative of a pathogenically active JAK-STAT1/2 cellular signaling pathway.

In one embodiment, the at least three, for example, at least four, at least five, at least six, at least seven, at least eight or more target genes are selected from IRF1, IRF7, IRF8, IRF9, OAS1, PDCD1, ST13, STAT1, and USP18. In one embodiment, the activity level of the JAK-STAT1/2 cellular signaling pathway is determined to be either IFN type I activity or IFN type II activity by using two calibrated pathway models of which one is calibrated on IFN type I activity and the other is calibrated on IFN type II activity. In one embodiment, the calibrated pathway model is a probabilistic model incorporating conditional probabilistic relationships that compare the expression levels of the at least three target genes in the sample with expression levels of the at least three target genes in the calibrated pathway model which define a level of the JAK-STAT1/2 transcription factor element to determine the activity level of the JAK-STAT1/2 transcription factor element in the sample. In one embodiment, the probabilistic model is a Bayesian network model. In one embodiment, the calibrated pathway model is a linear model incorporating relationships that compare the expression levels of the at least three target genes in the sample with expression levels of the at least three target genes in the calibrated pathway model which define a level of JAK-STAT1/2 transcription factor element to determine the activity level of the JAK-STAT1/2 transcription factor element in the sample. In an illustrative embodiment, the JAK-STAT1/2 inhibitor is Ruxolitinib, Tofacitinib, Oclacitinib, Baricitinib, Filgotinib, Gandotinib, Lestaurtinib, Momelotinib, Pacritinib, or Fedratinib. In one embodiment, the disease is a cancer or an immune disorder. In one embodiment, the cancer is a breast cancer, a cervical cancer, an endometrial cancer, an ovarian cancer, a pancreatic cancer, or a prostate cancer. In one embodiment, the cancer is a breast cancer.

D) A kit for measuring expression levels of JAK-STAT1/2 cellular signaling pathway target genes comprising:
  a. a set of polymerase chain reaction primers directed to at least six, for example, at least seven, at least eight, at least nine, at least ten or more JAK-STAT1/2 cellular signaling pathway target genes derived from a sample isolated from a subject; and
  b. a set of probes directed to the at least six JAK-STAT1/2 cellular signaling pathway target genes;
     wherein the at least six target genes are selected from BID, GNAZ, IRF1, IRF7, IRF8, IRF9, LGALS1, NCF4, NFAM1, OAS1, PDCD1, RAB36, RBX1, RFPL3, SAMM50, SMARCB1, SSTR3, ST13, STAT1, TRMT1, UFD1L, USP18, and ZNRF3.

In one embodiment, the at least six, for example, at least seven, at least eight or more target genes are selected from IRF1, IRF7, IRF8, IRF9, OAS1, PDCD1, ST13, STAT1, and USP18. In one embodiment, the kit further comprises a computer program product for determining the activity level of a JAK-STAT1/2 cellular signaling pathway in the subject comprising: a. a non-transitory computer readable storage medium having computer readable program code embodied therewith, the computer readable program code executable by at least one processor to: i. calculate an activity level of a JAK-STAT1/2 transcription factor element in the sample, wherein the activity level of the JAK-STAT1/2 transcription factor element in the sample is associated with JAK-STAT1/2 cellular signaling, and wherein the activity level of the JAK-STAT1/2 transcription factor element in the sample is calculated by: 1. receiving data on the expression levels of the at least six target genes derived from the sample; 2. calculating the activity level of the JAK-STAT1/2 transcription factor element in the sample using a calibrated pathway model, wherein the calibrated pathway model compares the expression levels of the at least six target genes in the sample with expression levels of the at least six target genes in the calibrated pathway model which define an activity level of the JAK-STAT1/2 transcription factor element; and, ii. calculate the activity level of the JAK-STAT1/2 cellular signaling pathway in the sample based on the calculated activity level of the JAK-STAT1/2 transcription factor element in the sample.

E) A kit for determining the activity level of a JAK-STAT1/2 cellular signaling pathway in a subject comprising:
  a. one or more components capable of identifying expression levels of at least three, for example, at least four, at least five, at least six, at least seven, at least eight, at least nine, at least ten or more JAK-STAT1/2 cellular signaling pathway target genes derived from a sample of the subject, wherein the at least three target genes are selected from BID, GNAZ, IRF1, IRF7, IRF8, IRF9, LGALS1, NCF4, NFAM1, OAS1, PDCD1, RAB36, RBX1, RFPL3, SAMM50, SMARCB1, SSTR3, ST13, STAT1, TRMT1, UFD1L, USP18, and ZNRF3; and,
  b. optionally, a non-transitory computer readable storage medium having computer readable program code embodied therewith, the computer readable program code executable by at least one processor to:
     i. calculate an activity level of a JAK-STAT1/2 transcription factor element in the sample, wherein the activity level of the JAK-STAT1/2 transcription factor element in the sample is associated with JAK-STAT1/2 cellular signaling, and wherein the activity level of the JAK-STAT1/2 transcription factor element in the sample is calculated by:
        1. receiving data on the expression levels of the at least three target genes derived from the sample;
        2. calculating the activity level of the JAK-STAT1/2 transcription factor element in the sample using a calibrated pathway model, wherein the calibrated pathway model compares the expression levels of the at least three target genes in the sample with expression levels of the at least three target genes in the calibrated pathway model which define an activity level of the JAK-STAT1/2 transcription factor element; and,
     ii. calculate the activity level of the JAK-STAT1/2 cellular signaling pathway in the sample based on the calculated activity level of the JAK-STAT1/2 transcription factor element in the sample.

In one embodiment, the activity level of the JAK-STAT1/2 cellular signaling pathway is determined to be either IFN type I activity or IFN type II activity by using two calibrated pathway models of which one is calibrated on IFN type I activity and the other is calibrated on IFN type II activity.

Determining the Activity Level of the JAK-STAT1/2 Cellular Signaling Pathway

The present invention provides new and improved methods and apparatuses, and in particular computer implemented methods and apparatuses, as disclosed herein, to assess the functional state or activity of the JAK-STAT1/2 cellular signaling pathway.

In one aspect of the invention, provided herein is a method of determining JAK-STAT1/2 cellular signaling in a subject comprising the steps of:
  a. calculating an activity level of a JAK-STAT1/2 transcription factor element in a sample isolated from a subject, wherein the activity level of the JAK-STAT1/2 transcription factor element in the sample is associated with JAK-STAT1/2 cellular signaling, and wherein the activity level of the JAK-STAT1/2 transcription factor element in the sample is calculated by:
i. receiving data on the expression levels of at least three, for example, at least four, at least five, at least six, at least seven, at least eight, at least nine, at least ten or more target genes derived from the sample, wherein the JAK-STAT1/2 transcription factor element controls transcription of the at least three target genes, and wherein the at least three target genes are selected from BID, GNAZ, IRF1, IRF7, IRF8, IRF9, LGALS1, NCF4, NFAM1, OAS1, PDCD1, RAB36, RBX1, RFPL3, SAMM50, SMARCB1, SSTR3, ST13, STAT1, TRMT1, UFD1L, USP18, and ZNRF3,
ii. calculating the activity level of the JAK-STAT1/2 transcription factor element in the sample using a calibrated pathway model, wherein the calibrated pathway model compares the expression levels of the at least three target genes in the sample with expression levels of the at least three more target genes in the calibrated pathway model which define an activity level of the JAK-STAT1/2 transcription factor element; and,
b. calculating the activity level of the JAK-STAT1/2 cellular signaling pathway in the sample based on the calculated activity level of the JAK-STAT1/2 transcription factor element in the sample.

As contemplated herein, the method of calculating the activity level of the JAK-STAT1/2 cellular signaling pathway is performed by a computer processor.

Figure 2:
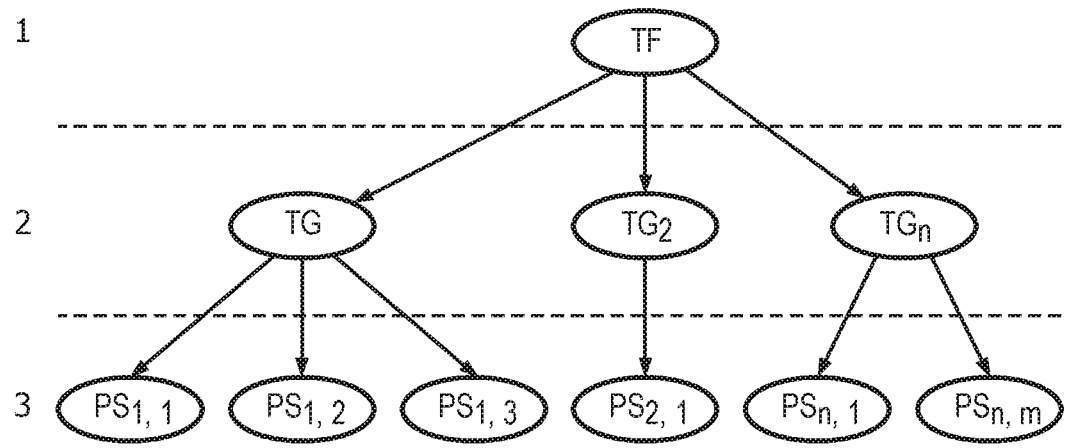
FIG. 2 shows schematically and exemplarily a mathematical model, herein, a Bayesian network model, useful in modelling the transcriptional program of the JAK-STAT1/2 cellular signaling pathway.

As a non-limiting generalized example, FIG. 2 provides an exemplary flow diagram used to determine the activity level of the JAK-STAT1/2 cellular signaling pathway based on a computer implemented mathematical model constructed of three nodes: (a) a transcription factor (TF) element (for example, but not limited to being, discretized into the states "absent" and "present" or as a continuous observable) in a first layer 1; (b) target genes $TG_1$, $TG_2$, $TG_n$ (for example, but not limited to being, discretized into the states "down" and "up" or as a continuous observable) in a second layer 2, and; (c) measurement nodes linked to the expression levels of the target genes in a third layer 3. The expression levels of the target genes can be determined by, for example, but not limited to, microarray probesets $PS_{1,1}$, $PS_{1,2}$, $PS_{1,3}$, $PS_{2,1}$, $PS_{n,1}$, $PS_{n,m}$ (for example, but limited to being, discretized into the states "low" and "high" or as a continuous observable), but could also be any other gene expression measurements such as, for example, RNAseq or RT-qPCR. The expression of the target genes depends on the activation of the respective transcription factor element, and the measured intensities of the selected probesets depend in turn on the expression of the respective target genes. The model is used to calculate JAK-STAT1/2 pathway activity by first determining probeset intensities, i.e., the expression level of the target genes, and calculating backwards in the calibrated pathway model what the probability is that the transcription factor element must be present.

The present invention makes it possible to determine the activity level of the JAK-STAT1/2 cellular signaling pathway in a subject by (i) determining an activity level of a JAK-STAT1/2 TF element in a sample of the subject, wherein the determining is based at least in part on evaluating a mathematical model relating expression levels of at least three, for example, at least four, at least five, at least six, at least seven, at least eight, at least nine, at least ten or more target genes of the JAK-STAT1/2 cellular signaling pathway, the transcription of which is controlled by the JAK-STAT1/2 TF element, to the activity level of the JAK-STAT1/2 TF element, and by (ii) calculating the activity level of the JAK-STAT1/2 cellular signaling pathway in the samplebased on the determined activity level of the JAK-STAT1/2 TF element in the sample. This preferably allows improving the possibilities of characterizing patients that have a disease, such as cancer, e.g., a breast, cervical, endometrial, ovarian, pancreatic or prostate cancer, which is at least partially driven by an abnormal activity of the JAK-STAT1/2 cellular signaling pathway, and that are therefore likely to respond to inhibitors of the JAK-STAT1/2 cellular signaling pathway. An important advantage of the present invention is that it makes it possible to determine the activity of the JAK-STAT1/2 cellular signaling pathway using a single sample, rather than requiring a plurality of samples extracted at different points in time.

Figure 3:
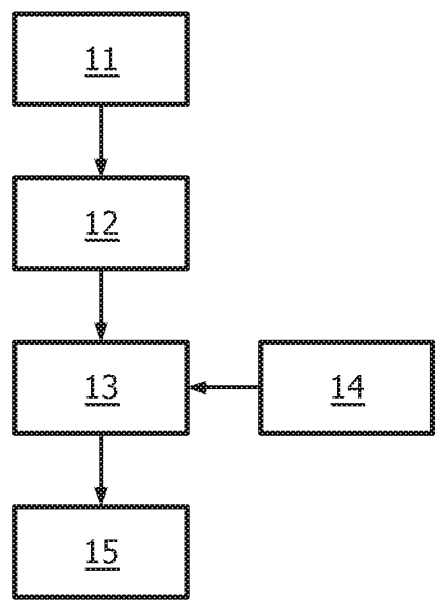
FIG. 3 shows an exemplary flow chart for calculating the activity level of the JAK-STAT1/2 cellular signaling pathway based on expression levels of target genes derived from a sample.

Generalized Workflow for Determining the Activity Level of JAK-STAT1/2 Cellular Signaling An example flow chart illustrating an exemplary calculation of the activity level of JAK-STAT1/2 cellular signaling from a sample isolated from a subject is provided in FIG. 3. First, the mRNA from a sample is isolated (11). Second, the mRNA expression levels of a unique set of at least three or more JAK-STAT1/2 target genes, as described herein, are measured (12) using methods for measuring gene expression that are known in the art. Next, the calculation of transcription factor element (13) is calculated using a calibrated pathway model (14), wherein the calibrated pathway model compares the expression levels of the at least three target genes in the sample with expression levels of the at least three target genes in the calibrated pathway model which have been correlated with a level of a JAK-STAT1/2 transcription factor element. Finally, the activity level of the JAK-STAT1/2 cellular signaling pathway is calculated in the sample based on the calculated levels of JAK-STAT1/2 transcription factor element in the sample (15). For example, the JAK-STAT1/2 signaling pathway is determined to be active if the activity is above a certain threshold, and can be categorized as passive if the activity falls below a certain threshold.

Target Genes

The present invention utilizes the analyses of the expression levels of unique sets of target genes. Particularly suitable target genes are described in the following text passages as well as the examples below (see, e.g., Tables 1 and 2 below).

Thus, according to an embodiment the target genes are selected from the group consisting of the target genes listed in Table 1 or Table 2 below.

In particular, the unique set of target genes whose expression is analyzed in the calibrated pathway model includes at least three or more target genes, for example, three, four, five, six, seven, eight, nine, ten or more, selected from BID, GNAZ, IRF1, IRF7, IRF8, IRF9, LGALS1, NCF4, NFAM1, OAS1, PDCD1, RAB36, RBX1, RFPL3, SAMM50, SMARCB1, SSTR3, ST13, STAT1, TRMT1, UFD1L, USP18, and ZNRF3.

In one embodiment, the at least three or more target genes, for example, three, four, five, six, seven, eight or more, are selected from IRF1, IRF7, IRF8, IRF9, OAS1, PDCD1, ST13, STAT1, and USP18.

In one embodiment, the activity level of the JAK-STAT1/2 cellular signaling pathway is determined to be either IFN type I activity or IFN type II activity by using two calibrated pathway models of which one is calibrated on IFN type I activity and the other is calibrated on IFN type II activity.

It has been found by the present inventors that the target genes in the shorter list are more probative for determining the activity of the JAK-STAT1/2 cellular signaling pathway.

Measuring Levels of Gene Expression

Data derived from the unique set of target genes described herein is further utilized to determine the activity level of the JAK-STAT1/2 cellular signaling pathway using the methods described herein.

Methods for analyzing gene expression levels in isolated samples are generally known. For example, methods such as Northern blotting, the use of PCR, nested PCR, quantitative real-time PCR (qPCR), RNA-seq, or microarrays can all be used to derive gene expression level data. All methods known in the art for analyzing gene expression of the target genes are contemplated herein.

Methods of determining the expression product of a gene using PCR based methods may be of particular use. In order to quantify the level of gene expression using PCR, the amount of each PCR product of interest is typically estimated using conventional quantitative real-time PCR (qPCR) to measure the accumulation of PCR products in real time after each cycle of amplification. This typically utilizes a detectible reporter such as an intercalating dye, minor groove binding dye, or fluorogenic probe whereby the application of light excites the reporter to fluoresce and the resulting fluorescence is typically detected using a CCD camera or photomultiplier detection system, such as that disclosed in U.S. Pat. No. 6,713,297 which is hereby incorporated by reference.

In some embodiments, the probes used in the detection of PCR products in the quantitative real-time PCR (qPCR) assay can include a fluorescent marker. Numerous fluorescent markers are commercially available. For example, Molecular Probes, Inc. (Eugene, Oreg.) sells a wide variety of fluorescent dyes. Non-limiting examples include Cy5, Cy3, TAMRA, R6G, R110, ROX, JOE, FAM, Texas Red™, and Oregon Green™. Additional fluorescent markers can include IDT ZEN Double-Quenched Probes with traditional 5' hydrolysis probes in qPCR assays. These probes can contain, for example, a 5' FAM dye with either a 3' TAMRA Quencher, a 3' Black Hole Quencher (BHQ, Biosearch Technologies), or an internal ZEN Quencher and 3' Iowa Black Fluorescent Quencher (IBFQ).

Fluorescent dyes useful according to the invention can be attached to oligonucleotide primers using methods well known in the art. For example, one common way to add a fluorescent label to an oligonucleotide is to react an N-Hydroxysuccinimide (NHS) ester of the dye with a reactive amino group on the target. Nucleotides can be modified to carry a reactive amino group by, for example, inclusion of an allyl amine group on the nucleobase. Labeling via allyl amine is described, for example, in U.S. Pat. Nos. 5,476,928 and 5,958,691, which are incorporated herein by reference. Other means of fluorescently labeling nucleotides, oligonucleotides and polynucleotides are well known to those of skill in the art.

Other fluorogenic approaches include the use of generic detection systems such as SYBR-green dye, which fluoresces when intercalated with the amplified DNA from any gene expression product as disclosed in U.S. Pat. Nos. 5,436,134 and 5,658,751 which are hereby incorporated by reference.

Another useful method for determining target gene expression levels includes RNA-seq, a powerful analytical tool used for transcriptome analyses, including gene expression level difference between different physiological conditions, or changes that occur during development or over the course of disease progression.

Another approach to determine gene expression levels includes the use of microarrays for example RNA and DNA microarray, which are well known in the art. Microarrays can be used to quantify the expression of a large number of genes simultaneously.

Calibrated Pathway Model

As contemplated herein, the expression levels of the unique set of target genes described herein are used to calculate the activity level of the JAK-STAT1/2 transcription factor element using a calibrated pathway model as further described below. The calibrated pathway model compares the expression levels of the at least three target genes in the sample with expression levels of the at least three target genes in the calibrated pathway model which define an activity level of the JAK-STAT1/2 transcription factor element.

As contemplated herein, the calibrated pathway model is based on the application of a mathematical model. For example, the calibrated model can be based on a probabilistic model, for example a Bayesian network, or a linear or pseudo-linear model.

In one embodiment, the calibrated pathway model is a probabilistic model incorporating conditional probabilistic relationships that compare the expression levels of the at least three target genes in the sample with expression levels of the at least three target genes in the calibrated pathway model which define a level of a JAK-STAT1/2 transcription factor element to determine the activity level of the JAK-STAT1/2 transcription factor element in the sample. In one embodiment, the probabilistic model is a Bayesian network model.

In an alternative embodiment, the calibrated pathway model can be a linear or pseudo-linear model. In an embodiment, the linear or pseudo-linear model is a linear or pseudo-linear combination model.

Figure 4:
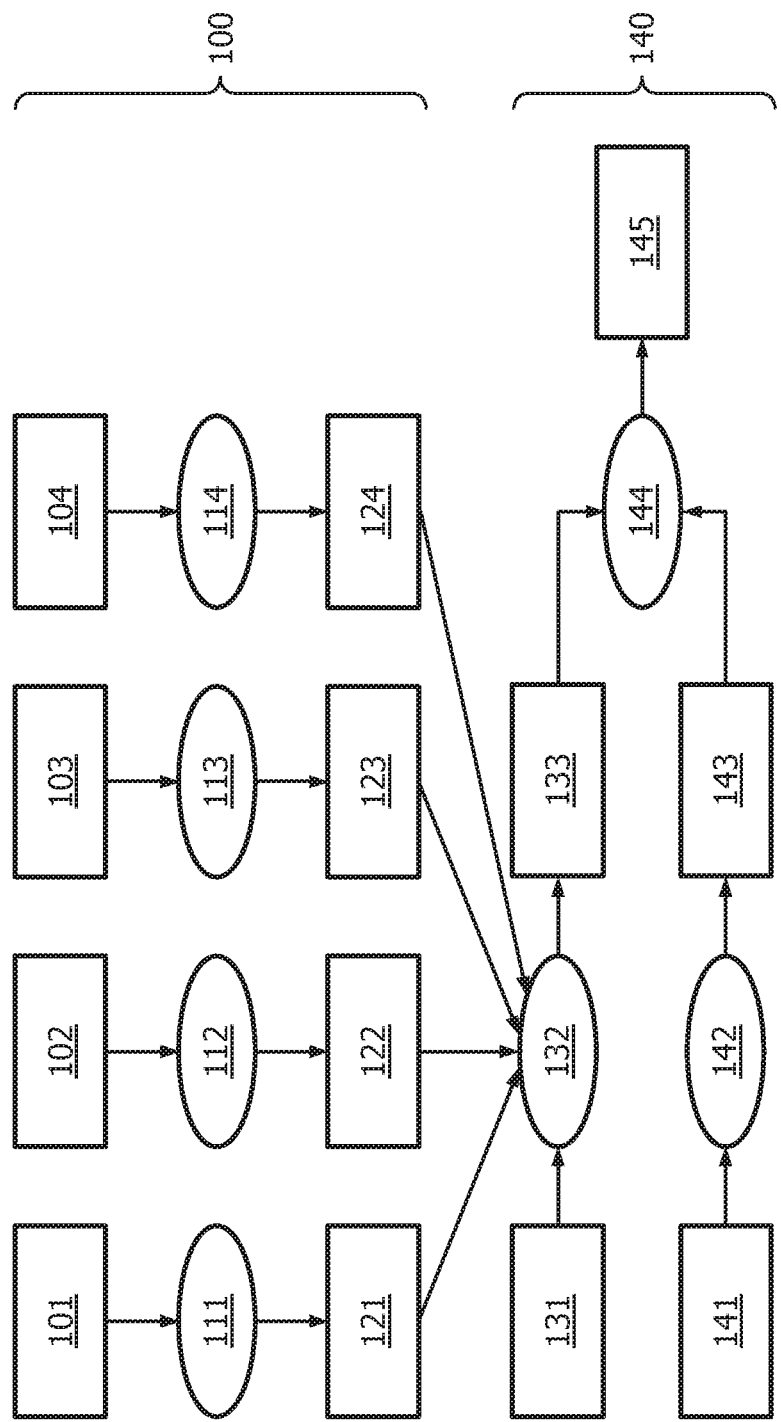
FIG. 4 shows an exemplary flow chart for obtaining a calibrated pathway model as described herein.

A non-limiting exemplary flow chart for a calibrated pathway model is shown in FIG. 4. As an initial step, the training data for the mRNA expression levels is collected and normalized. The data can be collected using, for example microarray probeset intensities (101), real-time PCR Cq values (102), raw RNAseq reads (103), or alternative measurement modalities (104) known in the art. The raw expression level data can then be normalized for each method, respectively, by normalization using a normalization algorithm, for example, frozen robust military analysis (fRMA) or MAS5.0 (111), normalization to average Cq of reference genes (112), normalization of reads into reads/fragments per kilobase of transcript per million mapped reads (RPKM/FPKM) (113), or normalization to w.r.t. reference genes/proteins (114). This normalization procedure leads to a normalized probeset intensity (121), normalized Cq values (122), normalized RPKM/FPKM (123), or normalized measurement (124) for each method, respectively, which indicate target gene expression levels within the training samples.

Once the training data has been normalized, a training sample ID or IDs (131) is obtained and the training data of these specific samples is obtained from one of the methods for determining gene expression (132). The final gene expression results from the training sample are output as training data (133). All of the data from various training samples are incorporated to calibrate the model (including for example, thresholds, CPTs, for example in the case of the probabilistic or Bayesian network, weights, for example, in the case of the linear or pseudo-linear model, etc) (144). In addition, the pathway's target genes and measurement nodes (141) are used to generate the model structure for example, as described in FIG. 2 (142). The resulting model structure (143) of the pathway is then incorporated with the training data (133) to calibrate the model (144), wherein the gene expression levels of the target genes is indicative of the transcription factor element activity. As a result of the transcription factor element calculations in the training samples, a calibrated pathway model (145) is calculated which assigns the JAK-STAT1/2 cellular signaling pathway activity level for a subsequently examined sample of interest, for example from a subject with a cancer, based on the target gene expression levels in the training samples.

Transcription Factor Element Calculation

Figure 5:
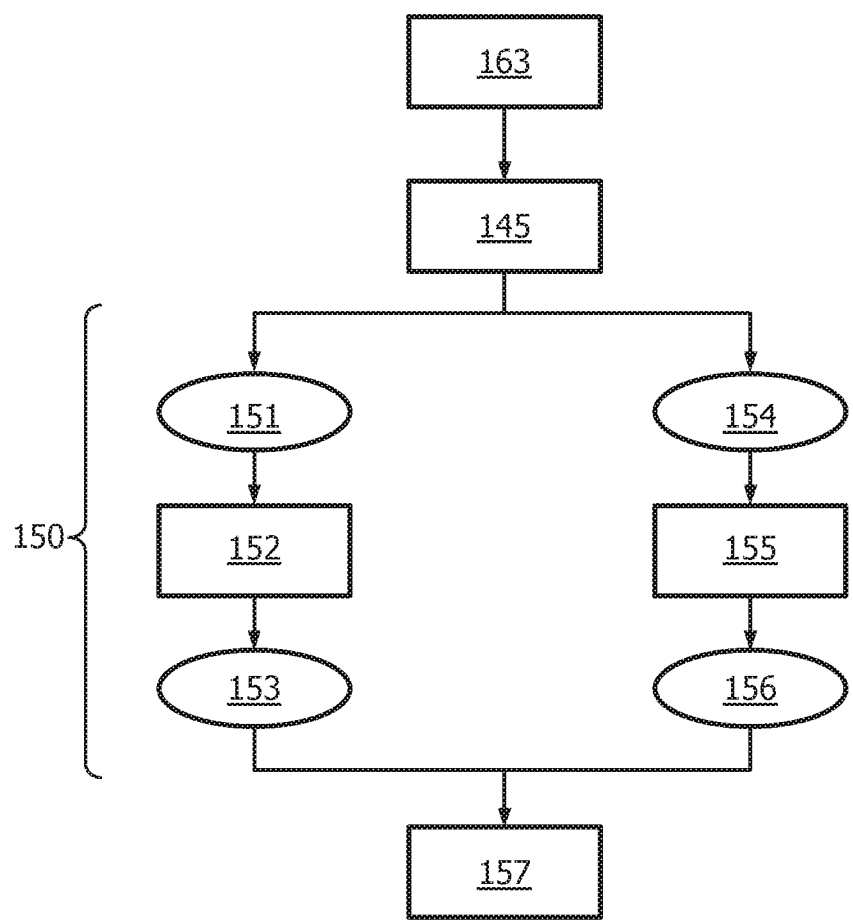
FIG. 5 shows an exemplary flow chart for calculating the Transcription Factor (TF) Element as described herein.

A non-limiting exemplary flow chart for calculating the Transcription Factor Element activity level is provided in FIG. 5. The expression level data (test data) (163) from a sample isolated from a subject is input into the calibrated pathway model (145). The mathematical model may be a probabilistic model, for example a Bayesian network model, a linear model, or pseudo-linear model.

The mathematical model may be a probabilistic model, for example a Bayesian network model, based at least in part on conditional probabilities relating the JAK-STAT1/2 TF element and expression levels of the at least three target genes of the JAK-STAT1/2 cellular signaling pathway measured in the sample of the subject, or the mathematical model may be based at least in part on one or more linear combination(s) of expression levels of the at least three target genes of the JAK-STAT1/2 cellular signaling pathway measured in the sample of the subject. In particular, the determining of the activity of the JAK-STAT1/2 cellular signaling pathway may be performed as disclosed in the published international patent application WO 2013/011479 A2 ("Assessment of cellular signaling pathway activity using probabilistic modeling of target gene expression"), and incorporated herein by reference. Briefly, the data is entered into a Bayesian network (BN) inference engine call (for example, a BNT toolbox) (154). This leads to a set of values for the calculated marginal BN probabilities of all the nodes in the BN (155). From these probabilities, the transcription factor (TF) node's probability (156) is determined and establishes the TF's element activity level (157).

Alternatively, the mathematical model may be a linear model. For example, a linear model can be used as described in the published international patent application WO 2014/102668 A2 ("Assessment of cellular signaling pathway activity using linear combination(s) of target gene expressions"), the contents of which are herewith incorporated in their entirety. Further details regarding the calculating/determining of cellular signaling pathway activity using mathematical modeling of target gene expression can also be found in Verhaegh W. et al., "Selection of personalized patient therapy through the use of knowledge-based computational models that identify tumor-driving signal transduction pathways", Cancer Research, Vol. 74, No. 11, 2014, pages 2936 to 2945. Briefly, the data is entered into a calculated weighted linear combination score (w/c) (151). This leads to a set of values for the calculated weighted linear combination score (152). From these weighted linear combination scores, the transcription factor (TF) node's weighted linear combination score (153) is determined and establishes the TF's element activity level (157).

Procedure for Discretized Observables

Figure 6:
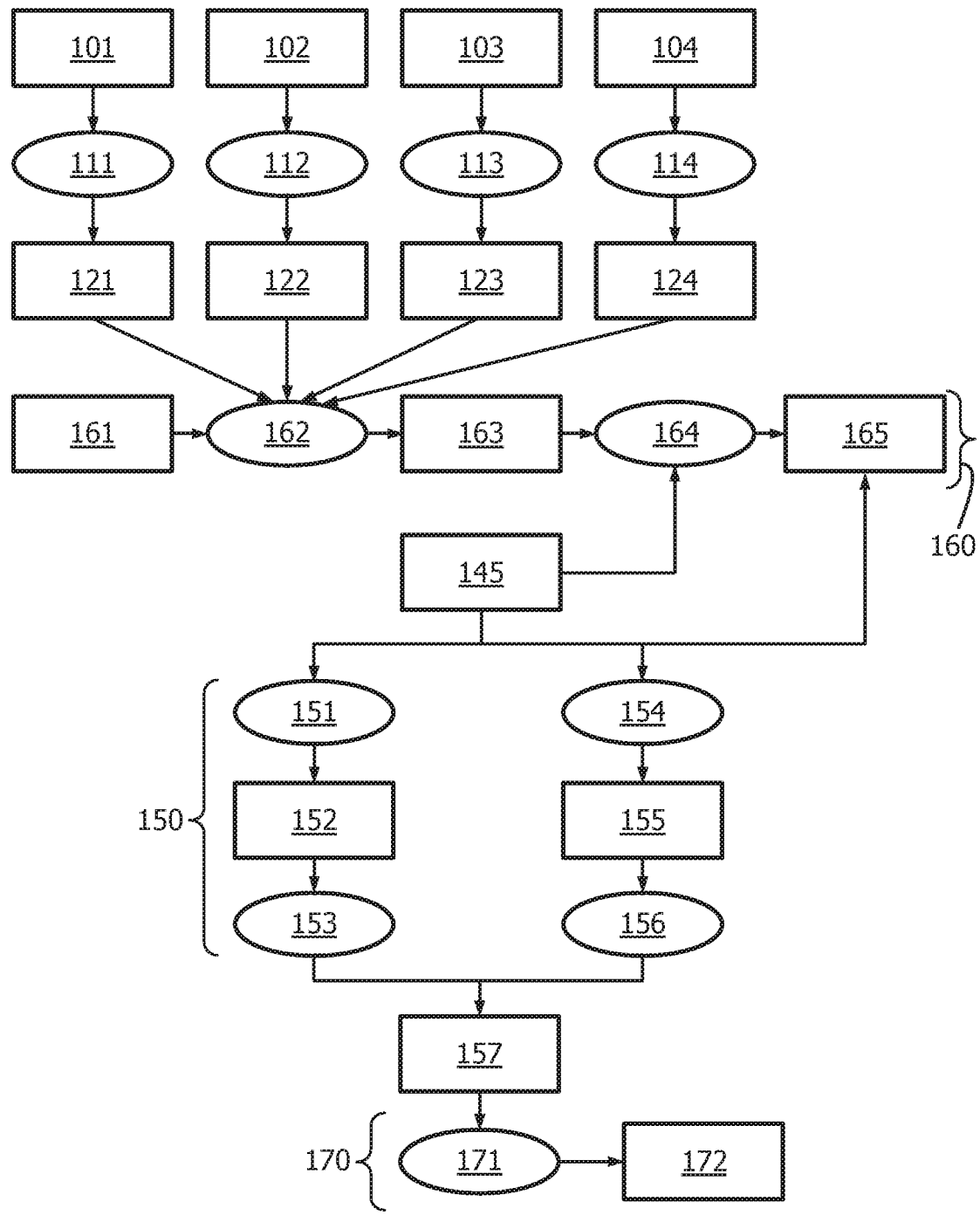
FIG. 6 shows an exemplary flow chart for calculating the JAK-STAT1/2 cellular signaling pathway activity level using discretized observables.

A non-limiting exemplary flow chart for calculating the activity level of a JAK-STAT1/2 cellular signaling pathway as a discretized observable is shown in FIG. 6. First, the test sample is isolated and given a test sample ID (161). Next, the test data for the mRNA expression levels is collected and normalized (162). The test data can be collected using the same methods as discussed for the training samples in FIG. 5, using microarray probeset intensities (101), real-time PCR Cq values (102), raw RNAseq reads (103), or an alternative measurement modalities (104). The raw expression level data can then be normalized for each method, respectively, by normalization using an algorithm, for example fRMA or MAS5.0 (111), normalization to average Cq of reference genes (112), normalization of reads into RPKM/FPKM (113), and normalization to w.r.t. reference genes/proteins (114). This normalization procedure leads to a normalized probeset intensity (121), normalized Cq values (122), normalized RPKM/FPKM (123), or normalized measurement (124) for each method, respectively.

Once the test data has been normalized, the resulting test data (163) is analyzed in a thresholding step (164) based on the calibrated pathway model (145), resulting in the thresholded test data (165). In using discrete observables, in one non-limiting example, every expression above a certain threshold is, for example, given a value of 1 and values below the threshold are given a value of 0, or in an alternative embodiment, the probability mass above the threshold as described herein is used as a thresholded value. Based on the calibrated pathway model, this value represents the TF's element activity level (157), which is then used to calculate the pathway's activity level (171). The final output gives the pathway's activity level (172) in the test sample being examined from the subject.

Procedure for Continuous Observables

Figure 7:
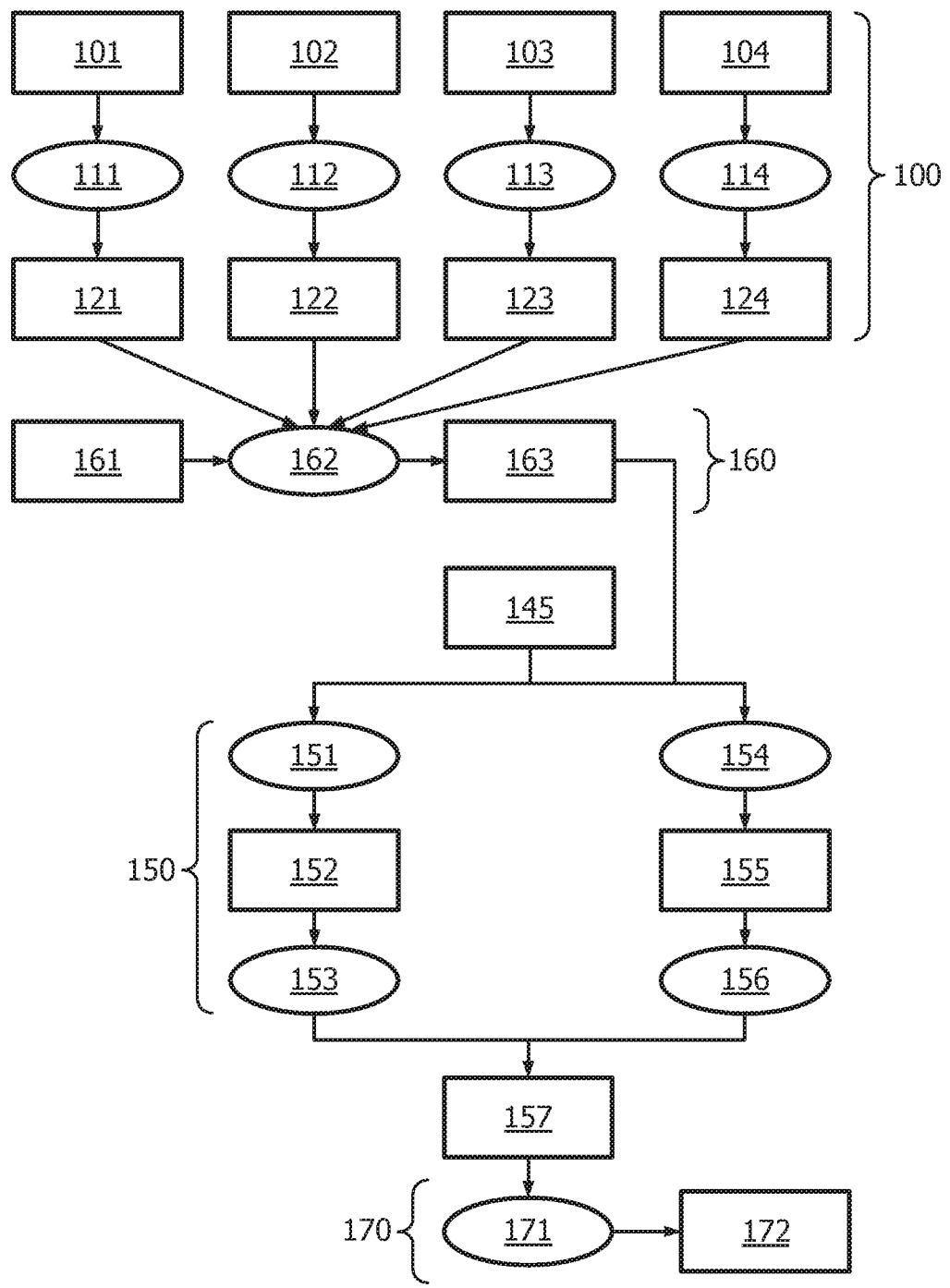
FIG. 7 shows an exemplary flow chart for calculating the JAK-STAT1/2 cellular signaling pathway activity level using continuous observables.

A non-limiting exemplary flow chart for calculating the activity level of a JAK-STAT1/2 cellular signaling pathway as a continuous observable is shown in FIG. 7. First, the test sample is isolated and given a test sample ID (161). Next, the test data for the mRNA expression levels is collected and normalized (162). The test data can be collected using the same methods as discussed for the training samples in FIG. 5, using microarray probeset intensities (101), real-time PCR Cq values (102), raw RNAseq reads (103), or an alternative measurement modalities (104). The raw expression level data can then be normalized for each method, respectively, by normalization using an algorithm, for example fRMA (111), normalization to average Cq of reference genes (112), normalization of reads into RPKM/FPKM (113), and normalization to w.r.t. reference genes/proteins (114). This normalization procedure leads to a a normalized probeset intensity (121), normalized Cq values (122), normalized RPKM/FPKM (123), or normalized measurement (124) for each method, respectively.

Once the test data has been normalized, the resulting test data (163) is analyzed in the calibrated pathway model (145). In using continuous observables, as one non-limiting example, the expression levels are converted to values between 0 and 1 using a sigmoid function as described in further detail below. The transcription factor element calculation as described herein is used to interpret the test data in combination with the calibrated pathway model, the resulting value represents the TF's element activity level (157), which is then used to calculate the pathway's activity level (171). The final output then gives the pathway's activity level (172) in the test sample.

Target Gene Expression Level Determination Procedure

Figure 8:
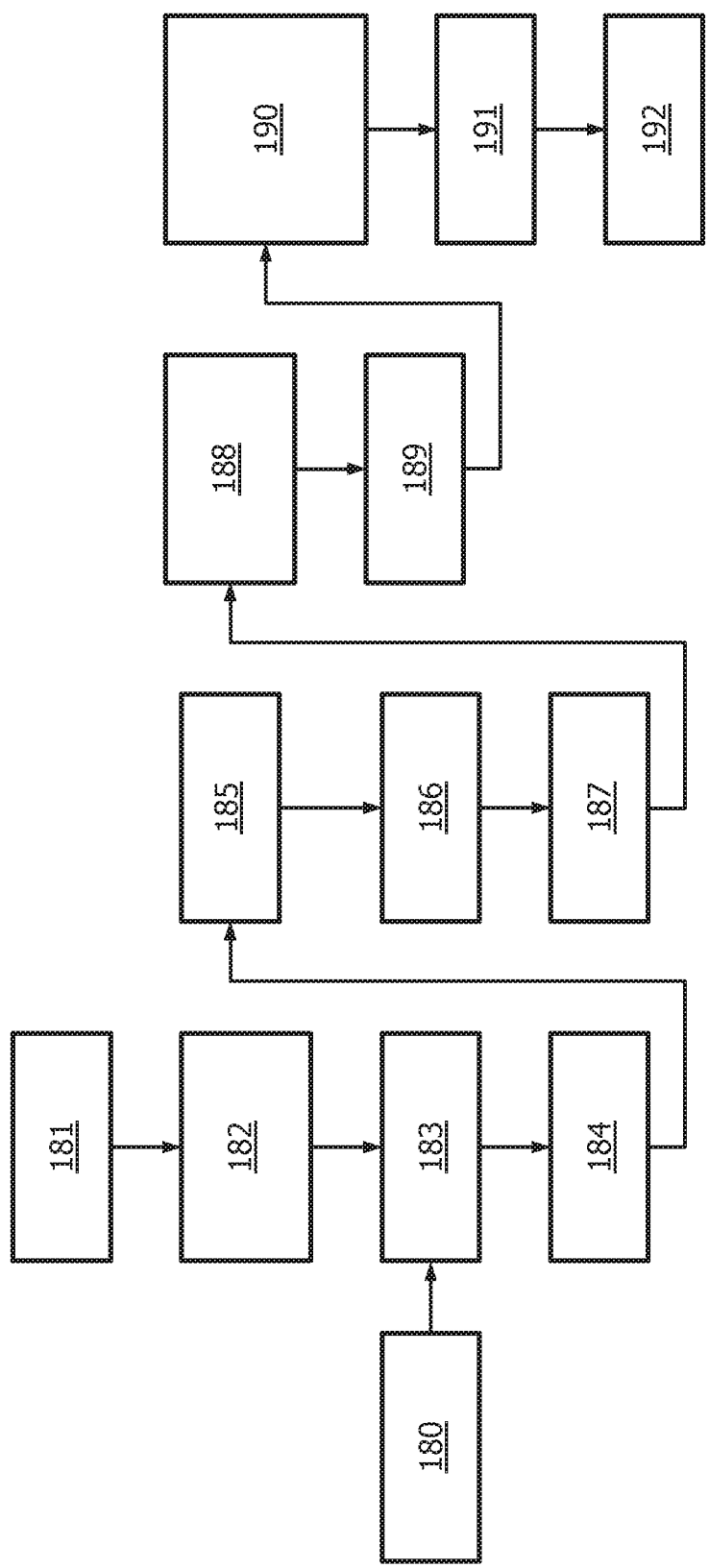
FIG. 8 shows an exemplary flow chart for determining Cq values from RT-qPCR analysis of the target genes of the JAK-STAT1/2 cellular signaling pathway.

A non-limiting exemplary flow chart for deriving target gene expression levels from a sample isolated from a subject is shown in FIG. 8. In one exemplary embodiment, samples are received and registered in a laboratory. Samples can include, for example, Formalin-Fixed, Paraffin-Embedded (FFPE) samples (181) or fresh frozen (FF) samples (180). FF samples can be directly lysed (183). For FFPE samples, the paraffin can be removed with a heated incubation step upon addition of Proteinase K (182). Cells are then lysed (183), which destroys the cell and nuclear membranes which makes the nucleic acid (NA) available for further processing. The nucleic acid is bound to a solid phase (184) which could for example, be beads or a filter. The nucleic acid is then washed with washing buffers to remove all the cell debris which is present after lysis (185). The clean nucleic acid is then detached from the solid phase with an elution buffer (186). The DNA is removed by DNAse treatment to ensure that only RNA is present in the sample (187). The nucleic acid sample can then be directly used in the RT-qPCR sample mix (188). The RT-qPCR sample mixes contains the RNA sample, the RT enzyme to prepare cDNA from the RNA sample and a PCR enzyme to amplify the cDNA, a buffer solution to ensure functioning of the enzymes and can potentially contain molecular grade water to set a fixed volume of concentration. The sample mix can then be added to a multiwell plate (i.e., 96 well or 384 well plate) which contains dried RT-qPCR assays (189). The RT-qPCR can then be run in a PCR machine according to a specified protocol (190). An example PCR protocol includes i) 30 minutes at 50° C.; ii) 5 minutes at 95° C.; iii) 15 seconds at 95° C.; iv) 45 seconds at 60° C.; v) 50 cycles repeating steps iii and iv. The Cq values are then determined with the raw data by using the second derivative method (191). The Cq values are exported for analysis (192).

Computer Programs and Computer Implemented Methods

As contemplated herein, the calculation of JAK-STAT1/2 signaling in the sample is performed on a computerized device having a processor capable of executing a readable program code for calculating the JAK-STAT1/2 cellular signaling pathway activity in the sample according to the methods described above. Accordingly, the computerized device can include means for receiving expression level data, wherein the data is expression levels of at least three, for example, at least four, at least five, at least six, at least seven, at least eight, at least nine, at least ten or more target genes derived from the sample, a means for calculating the activity level of a JAK-STAT1/2 transcription factor element in the sample using a calibrated pathway model, wherein the calibrated pathway model compares the expression levels of the at least three target genes in the sample with expression levels of the at least three target genes in the calibrated pathway model which have been correlated with a level of the JAK-STAT1/2 transcription factor element; a means for calculating the activity level of the JAK-STAT1/2 cellular signaling pathway in the sample based on the calculated activity level of JAK-STAT1/2 transcription factor element in the sample; and a means for assigning a JAK-STAT1/2 cellular signaling pathway activity probability or status to the calculated activity level of the JAK-STAT1/2 cellular signaling pathway in the sample, and a means for displaying the JAK-STAT1/2 signaling pathway activity probability or status.

In accordance with another disclosed aspect, a non-transitory storage medium stores instructions that are executable by a digital processing device to perform a method according to the present invention as described herein. The non-transitory storage medium may be a computer-readable storage medium, such as a hard drive or other magnetic storage medium, an optical disk or other optical storage medium, a random access memory (RAM), read only memory (ROM), flash memory, or other electronic storage medium, a network server, or so forth. The digital processing device may be a handheld device (e.g., a personal data assistant or smartphone), a notebook computer, a desktop computer, a tablet computer or device, a remote network server, or so forth.

In accordance with another disclosed aspect, an apparatus comprises a digital processor configured to perform a method according to the present invention as described herein.

In accordance with another disclosed aspect, a computer program comprises program code means for causing a digital processing device to perform a method according to the present invention as described herein. The digital processing device may be a handheld device (e.g., a personal data assistant or smartphone), a notebook computer, a desktop computer, a tablet computer or device, a remote network server, or so forth.

In one embodiment, a computer program or system is provided for predicting the activity status of a JAK-STAT1/2 transcription factor element in a human cancer sample that includes a means for receiving data corresponding to the expression level of at least three JAK-STAT1/2 target genes in a sample from a host. In some embodiments, a means for receiving data can include, for example, a processor, a central processing unit, a circuit, a computer, or the data can be received through a website.

In one embodiment, a computer program or system is provided for predicting the activity status of a JAK-STAT1/2 transcription factor element in a human cancer sample that includes a means for displaying the JAK-STAT1/2 pathway signaling status in a sample from a host. In some embodiments, a means for displaying can include a computer monitor, a visual display, a paper print out, a liquid crystal display (LCD), a cathode ray tube (CRT), a graphical keyboard, a character recognizer, a plasma display, an organic light-emitting diode (OLED) display, or a light emitting diode (LED) display, or a physical print out.

In accordance with another disclosed aspect, a signal represents a determined activity of a JAK-STAT1/2 cellular signaling pathway in a subject, wherein the determined activity results from performing a method according to the present invention as described herein. The signal can be a digital signal or it can be an analog signal.

In one aspect of the present invention, a computer implemented method is provided for predicting the activity status of a JAK-STAT1/2 signaling pathway in a human cancer sample performed by a computerized device having a processor comprising: a) calculating an activity level of a JAK-STAT1/2 transcription factor element in a human cancer sample, wherein the activity level of the JAK-STAT1/2 transcription factor element in the human cancer sample is associated with JAK-STAT1/2 cellular signaling, and wherein the activity level of the JAK-STAT1/2 transcription factor element in the human cancer sample is calculated by i) receiving data on the expression levels of at least three, for example, at least four, at least five, at least six, at least seven, at least eight, at least nine, at least ten or more target genes derived from the human cancer sample, wherein the JAK-STAT1/2 transcription factor controls transcription of the at least three target genes, and wherein the at least three target genes are selected from BID, GNAZ, IRF1, IRF7, IRF8, IRF9, LGALS1, NCF4, NFAM1, OAS1, PDCD1, RAB36, RBX1, RFPL3, SAMM50, SMARCB1, SSTR3, ST13, STAT1, TRMT1, UFD1L, USP18, and ZNRF3; ii) calculating the activity level of the JAK-STAT1/2 transcription factor element in the human cancer sample using a calibrated pathway model, wherein the calibrated pathway model compares the expression levels of the at least three target genes in the human cancer sample with expression levels of the at least three target genes in the calibrated pathway model which have been correlated with an activity level of the JAK-STAT1/2 transcription factor element; b) calculating the activity level of the JAK-STAT1/2 cellular signaling pathway in the human cancer sample based on the calculated activity level of the JAK-STAT1/2 transcription factor element in the human cancer sample; c) assigning a JAK-STAT1/2 cellular signaling pathway activity status to the calculated activity level of the JAK-STAT1/2 cellular signaling pathway in the human cancer sample, wherein the activity status is indicative of either an active JAK-STAT1/2 cellular signaling pathway or a passive JAK-STAT1/2 cellular signaling pathway; and d) displaying the JAK-STAT1/2 signaling pathway activity status.

In one aspect of the invention, a system is provided for determining the activity level of a JAK-STAT1/2 cellular signaling pathway in a subject comprising a) a processor capable of calculating an activity level of a JAK-STAT1/2 transcription factor element in a sample derived from the subject; b) a means for receiving data, wherein the data is an expression level of at least three, for example, at least four, at least five, at least six, at least seven, at least eight, at least nine, at least 10 or more target genes derived from the sample; c) a means for calculating the activity level of the JAK-STAT1/2 transcription factor element in the sample using a calibrated pathway model, wherein the calibrated pathway model compares the expression levels of the at least three target genes in the sample with expression levels of the at least three target genes in the calibrated pathway model which define an activity level of the JAK-STAT1/2 transcription factor element; d) a means for calculating the activity level of the JAK-STAT1/2 cellular signaling pathway in the sample based on the calculated activity level of JAK-STAT1/2 transcription factor element in the sample; a means for assigning a JAK-STAT1/2 cellular signaling pathway activity status to the calculated activity level of the JAK-STAT1/2 cellular signaling pathway in the sample, wherein the activity status is indicative of either an active JAK-STAT1/2 cellular signaling pathway or a passive JAK-STAT1/2 cellular signaling pathway; and f) a means for displaying the JAK-STAT1/2 signaling pathway activity status.

JAK-STAT1/2 Mediated Diseases and Disorders and Methods of Treatment

As contemplated herein, the methods and apparatuses of the present invention can be utilized to assess JAK-STAT1/2 cellular signaling pathway activity in a subject, for example a subject suspected of having, or having, a disease or disorder wherein the status of the JAK-STAT1/2 signaling pathway is probabtive, either wholly or partially, of disease presence or progression. In one embodiment, provided herein is a method of treating a subject comprising receiving information regarding the activity status of a JAK-STAT1/2 cellular signaling pathway derived from a sample isolated from the subject using the methods described herein and administering to the subject a JAK-STAT1/2 inhibitor if the information regarding the level of JAK-STAT1/2 cellular signaling pathway is indicative of an active JAK-STAT1/2 signaling pathway. In a particular embodiment, the JAK-STAT1/2 cellular signaling pathway activity indication is set at a cutoff value of odds of the JAK-STAT1/2 cellular signaling pathway being active of 10:1, 5:1, 4:1, 2:1, 1:1, 1:2, 1:4, 1:5, 1:10. JAK-STAT1/2 inhibitors are known and include, but are not limited to, Ruxolitinib, Tofacitinib, Oclacitinib, Baricitinib, Filgotinib, Gandotinib, Lestaurtinib, Momelotinib, Pacritinib, or Fedratinib.

The JAK-STAT1/2 pathway plays a role in a large number of diseases, such as in various cancer types like, for example, gastroesophageal cancer, Hepatocellular carcinoma, lung carcinoma and gastric cancer, and other cancer types and cancer subtypes that have an active JAK-STAT1/2 signaling pathway as a cancer driving pathway, in immune system-mediated diseases like inflammatory bowel disease, rheumatoid arthritis, psoriasis, SLE, multiple sclerosis, et cetera, and in inflammatory diseases like asthma, atherosclerosis, diabetes, psychiatric diseases like depression and schizophrenia, acne, endometriosis, et cetera. With such diseases, measuring the JAK-STAT1/2 pathway activity profile in immune cell types in tissue and blood is expected to be helpful to diagnose, subtype, and predict and/or monitor response to immunomodulatory, especially immunosuppressive and targeted immunosuppressive, therapy and monitoring immune response status. Prediction of response to drugs can be used to match an anti-STAT1/2 pathway drug to a patient. For example, anti-STAT1 drug pravastatin as treatment for Schizophrenia (Phase IV clinical trial), pre-eclampsia (Phase I), hyperlipidaemia (Phase I/II/III/IV), cirrhosis (Phase II/III), gastroesophageal cancer (Phase IV), myeloid leukaemia (Phase I/II), pneumonia (Phase 0), Tofacitinib for treatment of Rheumatoid arthritis (Phase juvenile idiopathic arthritis (Phase I/II/III), psoriasis (Phase I/II/III), ankylosing spondylitis (Phase II), keratoconjunctivitis sicca (Phase II), ulcerative colitis (Phase III), AZD for treatment of Hepatocellular carcinoma, lung carcinoma and gastric cancer (Phase I), essential thrombocythaemia myelofibrosis and post-polycythaemia vera (Phase I), and Oligodeoxy-nucleotide decoy for treatment of head and neck cancer (Phase O) (see also Miklossy G. et al., "Therapeutic modulators of STAT signaling for human diseases", Nature Reviews Drug Discovery, Vol. 12, No. 8, August 2013, pages 611 to 629).

The sample(s) to be used in accordance with the present invention can be an extracted sample, that is, a sample that has been extracted from the subject. Examples of the sample include, but are not limited to, a tissue, cells, blood and/or a body fluid of a subject. It can be, e.g., a sample obtained from a cancer lesion, or from a lesion suspected for cancer, or from a metastatic tumor, or from a body cavity in which fluid is present which is contaminated with cancer cells (e.g., pleural or abdominal cavity or bladder cavity), or from other body fluids containing cancer cells, and so forth, for example, via a biopsy procedure or other sample extraction procedure. The cells of which a sample is extracted may also be tumorous cells from hematologic malignancies (such as leukemia or lymphoma). In some cases, the cell sample may also be circulating tumor cells, that is, tumor cells that have entered the bloodstream and may be extracted using suitable isolation techniques, e.g., apheresis or conventional venous blood withdrawal. Aside from blood, a body fluid of which a sample is extracted may be urine, gastrointestinal contents, or anextravasate.

In one aspect of the present invention, the methods and apparatuses described herein are used to identify an active JAK-STAT1/2 cellular signaling pathway in a subject suffering from a cancer, and administering to the subject an anti-cancer agent, for example a JAK-STAT1/2 inhibitor, selected from, but not limited to, Ruxolitinib, Tofacitinib, Oclacitinib, Baricitinib, Filgotinib, Gandotinib, Lestaurtinib, Momelotinib, Pacritinib, or Fedratinib.

Another aspect of the present invention relates to a method (as described herein), further comprising:

determining whether the JAK-STAT1/2 cellular signaling pathway is operating abnormally in the subject based on the calculated activity of the JAK-STAT1/2 cellular signaling pathway in the subject.

Here, the term "abnormally" denotes disease-promoting activity of the JAK-STAT1/2 cellular signaling pathway, for example, a tumor-promoting activity.

The present invention also relates to a method (as described herein) further comprising:

recommending prescribing a drug, for example, a JAK-STAT1/2 inhibitor, for the subject that corrects for abnormal operation of the JAK-STAT1/2 cellular signaling pathway, wherein the recommending is performed if the JAK-STAT1/2 cellular signaling pathway is determined to be operating abnormally in the subject based on the calculated/determined activity of the JAK-STAT1/2 cellular signaling pathway.

The present invention also relates to a method (as described herein), wherein the calculating/determining comprises:

calculating the activity of the JAK-STAT1/2 cellular signaling pathway in the subject based at least on expression levels of two, three or more target genes of a set of target genes of the JAK-STAT1/2 cellular signaling pathway measured in the sample of the subject.

The present invention as described herein can, e.g., also advantageously be used in connection with:

diagnosis based on the determined activity of the JAK-STAT1/2 cellular signaling pathway in the subject;

prognosis based on the determined activity of the JAK-STAT1/2 cellular signaling pathway in the subject;

drug prescription based on the determined activity of the JAK-STAT1/2 cellular signaling pathway in the subject;

prediction of drug efficacy based on the determined activity of the JAK-STAT1/2 cellular signaling pathway in the subject;

prediction of adverse effects based on the determined activity of the JAK-STAT1/2 cellular signaling pathway in the subject;

monitoring of drug efficacy;

drug development;

assay development;

pathway research;

cancer staging;

enrollment of the subject in a clinical trial based on the determined activity of the JAK-STAT1/2 cellular signaling pathway in the subject;

selection of subsequent test to be performed; and selection of companion diagnostics tests.

Further advantages will be apparent to those of ordinary skill in the art upon reading and understanding the attached figures, the following description and, in particular, upon reading the detailed examples provided herein below.

It shall be understood that an embodiment of the present invention can also be any combination of the dependent claims or above embodiments with the respective independent claim.

These and other aspects of the invention will be apparent from and elucidated with reference to the embodiments described hereinafter.

EXAMPLES

The following examples merely illustrate exemplary methods and selected aspects in connection therewith. The teaching provided therein may be used for constructing several tests and/or kits, e.g., to detect, predict and/or diagnose the abnormal activity of the JAK-STAT1/2 cellular signaling pathway. Furthermore, upon using methods as described herein drug prescription can advantageously be guided, drug response prediction and monitoring of drug efficacy (and/or adverse effects) can be made, drug resistance can be predicted and monitored, e.g., to select subsequent test(s) to be performed (like a companion diagnostic test). The following examples are not to be construed as limiting the scope of the present invention.

Example 1: Mathematical Model Construction

As described in detail in the published international patent application WO 2013/011479 A2 ("Assessment of cellular signaling pathway activity using probabilistic modeling of target gene expression"), by constructing a probabilistic model, e.g., a Bayesian network model, and incorporating conditional probabilistic relationships between expression levels of at least three, for example, at least four, at least five, at least six, at least seven, at least nine, at least ten or more target genes of a cellular signaling pathway, herein, the JAK-STAT1/2 cellular signaling pathway, and the level of a transcription factor (TF) element, herein, the JAK-STAT1/2 TF element, the TF element controlling transcription of the at least three target genes of the cellular signaling pathway, such a model may be used to determine the activity of the cellular signaling pathway with a high degree of accuracy. Moreover, the probabilistic model can be readily updated to incorporate additional knowledge obtained by later clinical studies, by adjusting the conditional probabilities and/or adding new nodes to the model to represent additional information sources. In this way, the probabilistic model can be updated as appropriate to embody the most recent medical knowledge.

In another easy to comprehend and interpret approach described in detail in the published international patent application WO 2014/102668 A2 ("Assessment of cellular signaling pathway activity using linear combination(s) of target gene expressions"), the activity of a cellular signaling pathway, herein, the JAK-STAT1/2 cellular signaling pathway, may be determined by constructing and evaluating a linear or (pseudo-)linear model incorporating relationships between expression levels of at least three, for example, at least four, at least five, at least six, at least seven, at least nine, at least ten or more target genes of the cellular signaling pathway and the level of a transcription factor (TF) element, herein, the JAK-STAT1/2 TF element, the TF element controlling transcription of the at least three target genes of the cellular signaling pathway, the model being based at least in part on one or more linear combination(s) of expression levels of the at least three target genes.

In both approaches, the expression levels of the at least three target genes may, for example, be measurements of the level of mRNA, which can be the result of, e.g., (RT)-PCR and microarray techniques using probes associated with the target genes mRNA sequences, and of RNA-sequencing. In another embodiment, the expression levels of the at least three target genes can be measured by protein levels, e.g., the concentrations and/or activity of the protein(s) encoded by the target genes.

The aforementioned expression levels may optionally be converted in many ways that might or might not suit the application better. For example, four different transformations of the expression levels, e.g., microarray-based mRNA levels, may be:

"continuous data", i.e., expression levels as obtained after preprocessing of microarrays using well known algorithms such as MAS5.0 and fRMA, "z-score", i.e., continuous expression levels scaled such that the average across all samples is 0 and the standard deviation is 1, "discrete", i.e., every expression above a certain threshold is set to 1 and below it to 0 (e.g., the threshold for a probeset may be chosen as the (weighted) median of its value in a set of a number of positive and the same number of negative clinical samples), "fuzzy", i.e., the continuous expression levels are converted to values between 0 and 1 using a sigmoid function of the following format: $1/(1+\exp((\text{thr}-\text{expr})/\text{se}))$, with expr being the continuous expression levels, thr being the threshold as mentioned before and se being a softening parameter influencing the difference between 0 and 1.

One of the simplest linear models that can be constructed is a model having a node representing the transcription factor (TF) element, herein, the JAK-STAT1/2 TF element, in a first layer and weighted nodes representing direct measurements of the target genes expression levels, e.g., by one probeset that is particularly highly correlated with the particular target gene, e.g., in microarray or (q)PCR experiments, in a second layer. The weights can be based either on calculations from a training data set or based on expert knowledge. This approach of using, in the case where possibly multiple expression levels are measured per target gene (e.g., in the case of microarray experiments, where one target gene can be measured with multiple probesets), only one expression level per target gene is particularly simple. A specific way of selecting the one expression level that is used for a particular target gene is to use the expression level from the probeset that is able to separate active and passive samples of a training data set the best. One method to determine this probeset is to perform a statistical test, e.g., the t-test, and select the probeset with the lowest p-value. The training data set's expression levels of the probeset with the lowest p-value is by definition the probeset with the least likely probability that the expression levels of the (known) active and passive samples overlap. Another selection method is based on odds-ratios. In such a model, one or more expression level(s) are provided for each of the at least three target genes and the one or more linear combination(s) comprise a linear combination including for each of the at least three target genes a weighted term, each weighted term being based on only one expression level of the one or more expression level(s) provided for the respective target gene. If the only one expression level is chosen per target gene as described above, the model may be called a "most discriminant probesets" model.

In an alternative to the "most discriminant probesets" model, it is possible, in the case where possibly multiple expression levels are measured per target gene, to make use of all the expression levels that are provided per target gene. In such a model, one or more expression level(s) are provided for each of the at least three target genes and the one or more linear combination(s) comprise a linear combination of all expression levels of the one or more expression level(s) provided for the at least three target genes. In other words, for each of the at least three target genes, each of the one or more expression level(s) provided for the respective target gene may be weighted in the linear combination by its own (individual) weight. This variant may be called an "all probesets" model. It has an advantage of being relatively simple while making use of all the provided expression levels.

Both models as described above have in common that they are what may be regarded as "single-layer" models, in which the level of the TF element is calculated based on a linear combination of expression levels of the one or more probeset of the one or more target genes.

After the level of the TF element, herein, the JAK-STAT1/2 TF element, has been determined by evaluating the respective model, the determined TF element level can be thresholded in order to infer the activity of the cellular signaling pathway, herein, the JAK-STAT1/2 cellular signaling pathway. An exemplary method to calculate such an appropriate threshold is by comparing the determined TF element levels wlc of training samples known to have a passive cellular signaling pathway and training samples with an active cellular signaling pathway. A method that does so and also takes into account the variance in these groups is given by using a threshold $$thr = \frac{\sigma_{wlc_{pas}} \mu_{wlc_{act}} + \sigma_{wlc_{act}} \mu_{wlc_{pas}}}{\sigma_{wlc_{pas}} + \sigma_{wlc_{act}}} \quad (1)$$

where $\sigma$ and $\mu$ are the standard deviation and the mean of the determined TF element levels wlc for the training samples. In case only a small number of samples are available in the active and/or passive training samples, a pseudocount may be added to the calculated variances based on the average of the variances of the two groups:

$$\tilde{v} = \frac{v_{wlc_{act}} + v_{wlc_{pas}}}{2} \quad (2)$$

$$\tilde{v}_{wlc_{act}} = \frac{x\tilde{v} + (n_{act} - 1)v_{wlc_{act}}}{x + n_{act} - 1}$$

$$\tilde{v}_{wlc_{pas}} = \frac{x\tilde{v} + (n_{pas} - 1)v_{wlc_{pas}}}{x + n_{pas} - 1}$$

where v is the variance of the determined TF element levels wlc of the groups, x is a positive pseudocount, e.g., 1 or 10, and nact and npas are the number of active and passive samples, respectively. The standard deviation $\sigma$ can next be obtained by taking the square root of the variance v.

The threshold can be subtracted from the determined TF element levels wlc for ease of interpretation, resulting in a cellular signaling pathway's activity score in which negative values correspond to a passive cellular signaling pathway and positive values correspond to an active cellular signaling pathway.

As an alternative to the above-described "single-layer" models, a "two-layer" may also be used in an example. In such a model, a summary value is calculated for every target gene using a linear combination based on the measured intensities of its associated probesets ("first (bottom) layer"). The calculated summary value is subsequently combined with the summary values of the other target genes of the cellular signaling pathway using a further linear combination ("second (upper) layer"). Again, the weights can be either learned from a training data set or based on expert knowledge or a combination thereof. Phrased differently, in the "two-layer" model, one or more expression level(s) are provided for each of the at least three target genes and the one or more linear combination(s) comprise for each of the at least three target genes a first linear combination of all expression levels of the one or more expression level(s) provided for the respective target gene ("first (bottom) layer"). The model is further based at least in part on a further linear combination including for each of the at least three target genes a weighted term, each weighted term being based on the first linear combination for the respective target gene ("second (upper) layer").

The calculation of the summary values can, in an exemplary version of the "two-layer" model, include defining a threshold for each target gene using the training data and subtracting the threshold from the calculated linear combination, yielding the target gene summary. Here the threshold may be chosen such that a negative target gene summary value corresponds to a down-regulated target gene and that a positive target gene summary value corresponds to an up-regulated target gene. Also, it is possible that the target gene summary values are transformed using, e.g., one of the above-described transformations (fuzzy, discrete, etc.), before they are combined in the "second (upper) layer".

After the level of the TF element has been determined by evaluating the "two-layer" model, the determined TF element level can be thresholded in order to infer the activity of the cellular signaling pathway, as described above.

In the following, the models described above are collectively denoted as "(pseudo-) linear" models. A more detailed description of the training and use of probabilistic models, e.g., a Bayesian network model, is provided in Example 3 below.

Example 2: Selection of Target Genes

A transcription factor (TF) is a protein complex (i.e., a combination of proteins bound together in a specific structure) or a protein that is able to regulate transcription from target genes by binding to specific DNA sequences, thereby controlling the transcription of genetic information from DNA to mRNA. The mRNA directly produced due to this action of the TF complex is herein referred to as a "direct target gene" (of the transcription factor). Cellular signaling pathway activation may also result in more secondary gene transcription, referred to as "indirect target genes". In the following, (pseudo-)linear models or Bayesian network models (as exemplary mathematical models) comprising or consisting of direct target genes as direct links between cellular signaling pathway activity and mRNA level, are exemplified, however the distinction between direct and indirect target genes is not always evident. Herein, a method to select direct target genes using a scoring function based on available scientific literature data is presented. Nonetheless, an accidental selection of indirect target genes cannot be ruled out due to limited information as well as biological variations and uncertainties. In order to select the target genes, the MEDLINE database of the National Institute of Health accessible at "www.ncbi.nlm.nih.gov/pubmed" and herein further referred to as "Pubmed" was employed to generate a lists of target genes. Furthermore, three additional lists of target genes were selected based on the probative nature of their expression.

Publications containing putative JAK-STAT1/2 target genes were searched for by using queries such as ("JAK-STAT1/2" AND "target gene") in the period of the first and second quarter of 2017. The resulting publications were further analyzed manually following the methodology described in more detail below.

Specific cellular signaling pathway mRNA target genes were selected from the scientific literature, by using a ranking system in which scientific evidence for a specific target gene was given a rating, depending on the type of scientific experiments in which the evidence was accumulated. While some experimental evidence is merely suggestive of a gene being a direct target gene, like for example an mRNA increasing as detected by means of an increasing intensity of a probeset on a microarray of a cell line in which it is known that the JAK-STAT1/2 cellular signaling pathway is active, other evidence can be very strong, like the combination of an identified JAK-STAT1/2 cellular signaling pathway TF binding site and retrieval of this site in a chromatin immunoprecipitation (ChIP) assay after stimulation of the specific cellular signaling pathway in the cell and increase in mRNA after specific stimulation of the cellular signaling pathway in a cell line.

Several types of experiments to find specific cellular signaling pathway target genes can be identified in the scientific literature:

1. ChIP experiments in which direct binding of a TF of the cellular signaling pathway of interest to its binding site on the genome is shown. Example: By using chromatin immunoprecipitation (ChIP) technology subsequently putative functional JAK-STAT1/2 TF binding sites in the DNA of cell lines with and without active induction of the JAK-STAT1/2 cellular signaling pathway, e.g., by stimulation with JAK-STAT1/2, were identified, as a subset of the binding sites recognized purely based on nucleotide sequence. Putative functionality was identified as ChIP-derived evidence that the TF was found to bind to the DNA binding site.
2. Electrophoretic Mobility Shift (EMSA) assays which show in vitro binding of a TF to a fragment of DNA containing the binding sequence. Compared to ChIP-based evidence EMSA-based evidence is less strong, since it cannot be translated to the in vivo situation.
3. Stimulation of the cellular signaling pathway and measuring mRNA expression using a microarray, RNA sequencing, quantitative PCR or other techniques, using JAK-STAT1/2 cellular signaling pathway-inducible cell lines and measuring mRNA profiles measured at least one, but preferably several time points after induction—in the presence of cycloheximide, which inhibits translation to protein, thus the induced mRNAs are assumed to be direct target genes.
4. Similar to 3, but alternatively measure the mRNAs expression further downstream with protein abundance measurements, such as western blot.
5. Identification of TF binding sites in the genome using a bioinformatics approach. Example for the JAK-STAT1/2 TF element: Using the ISRE binding motif 'AGTTTCNNTTCNC/T' and the GAS binding motif 'TTC/ANNNG/TAA', the potential binding sites were identified in gene promoter regions.
6. Similar as 3, only in the absence of cycloheximide.
7. Similar to 4, only in the absence of cycloheximide.

In the simplest form one can give every potential gene 1 point for each of these experimental approaches in which the gene was identified as being a target gene of the JAK-STAT1/2 family of transcription factors. Using this relative ranking strategy, one can make a list of most reliable target genes.

Alternatively, ranking in another way can be used to identify the target genes that are most likely to be direct target genes, by giving a higher number of points to the technology that provides most evidence for an in vivo direct target gene. In the list above, this would mean 7 points for experimental approach 1), 6 for 2), and going down to 1 point for experimental approach 7). Such a list may be called a "general list of target genes".

Despite the biological variations and uncertainties, the inventors assumed that the direct target genes are the most likely to be induced in a tissue-independent manner. A list of these target genes may be called an "evidence curated list of target genes". Such an evidence curated list of target genes has been used to construct computational models of the JAK-STAT1/2 cellular signaling pathway that can be applied to samples coming from different tissue sources.

The following will illustrate exemplary how the selection of an evidence curated target gene list specifically was constructed for the JAK-STAT1/2 cellular signaling pathway.

A scoring function was introduced that gave a point for each type of experimental evidence, such as ChIP, EMSA, differential expression, knock down/out, luciferase gene reporter assay, sequence analysis, that was reported in a publication. The same experimental evidence is sometimes mentioned in multiple publications resulting in a corresponding number of points, e.g., two publications mentioning a ChIP finding results in twice the score that is given for a single ChIP finding. Further analysis was performed to allow only for genes that had diverse types of experimental evidence and not only one type of experimental evidence, e.g., differential expression. Those genes that had more than one type of experimental evidence available were selected (as shown in Table 1).

A further selection of the evidence curated list of target genes (listed in Table 2) was made by the inventors. The target genes of the evidence curated list that were proven to be more probative in determining the activity of the JAK-STAT1/2 signaling pathway from the training samples were selected. Herein, available expression data sets of blood monocytes from 11 healthy donors from data set GSE38351 were used. 19 samples were STAT1/2 inactive, including 11 samples with monocytes incubated without any stimulation, and 8 samples with monocytes that were isolated immediately after drawing blood. The JAK-STAT1/2 active group included 7 samples stimulated with IFNα2a samples and 7 samples stimulated with IFNγ. The gene expression values for the "evidence curated list of target genes" (23 target genes list) from Table 1 were compared between STAT1/2 active and inactive samples from the GSE38351 data set. If the expression level of a target gene was obviously differentiated between the pathway active and inactive groups, which signifies that the target gene can be used to distinguish between the pathway active and inactive groups, then the target gene was selected. This resulted in the "9 target genes shortlist" shown in Table 2.

TABLE 1

"Evidence curated list of target genes" (23 target genes list) of the JAK-STAT1/2 cellular signaling pathway used in the JAK-STAT1/2 cellular signaling pathway models and associated probesets used to measure the mRNA expression level of the target genes.

| Target gene | Probeset | Target gene | Probeset |
| --- | --- | --- | --- |
| BID | 229321_s_at | SAMM50 | 201569_s_at |
|  | 227143_s_at |  | 201570_at |
|  | 204493_at |  | 243239_at |
|  | 211725_s_at |  | 230396_at |
| GNAZ | 220105_at | SMARCB1 | 212167_s_at |
|  | 204993_at |  | 206532_at |
| IRF1 | 202531_at |  | 231324_at |
| IRF7 | 208436_s_at |  | 228897_at |

TABLE 1-continued

"Evidence curated list of target genes" (23 target genes list) of the JAK-STAT1/2 cellular signaling pathway used in the JAK-STAT1/2 cellular signaling pathway models and associated probesets used to measure the mRNA expression level of the target genes.

| Target gene | Probeset | Target gene | Probeset |
| --- | --- | --- | --- |
| IRF8 | 204057_at |  | 228898_s_at |
| IRF9 | 220788_s_at | SSTR3 | 214491_at |
|  | 225122_at |  | 1553178_a_at |
|  | 231635_x_at | ST13 | 208666_s_at |
|  | 203882_at |  | 208667_s_at |
| LGALS1 | 201105_at |  | 207040_s_at |
| NCF4 | 205147_x_at | STAT1 | 200887_s_at |
|  | 207677_s_at |  | 232375_at |
| NFAM1 | 243099_at |  | 209969_s_at |
|  | 230322_at | TRMT1 | 203701_s_at |
| OAS1 | 205552_s_at |  | 210463_x_at |
| PDCD1 | 207634_at |  | 216454_at |
| RAB36 | 211471_s_at | UFD1L | 209103_s_at |
|  | 1555158_at | USP18 | 219211_at |
| RBX1 | 218117_at | ZNRF3 | 226360_at |
| RFPL3 | 207936_x_at |  | 244820_at |
|  |  |  | 243014_at |

TABLE 2

"9 target genes shortlist" of target genes of the JAK-STAT1/2 cellular signaling pathway genes. (The associated probesets are the same as in based on the evidence curated list of target Table 1.)

Target gene

IRF1
IRF7
IRF8
IRF9
OAS1
PDCD1
ST13
STAT1
USP18

Example 3: Training and Using the Mathematical Model

Before the mathematical model can be used to infer the activity of the cellular signaling pathway, herein, the JAK-STAT1/2 cellular signaling pathway, in a subject, the model must be appropriately trained.

If the mathematical model is a probabilistic model, e.g., a Bayesian network model, based at least in part on conditional probabilities relating the JAK-STAT1/2 TF element and expression levels of the at least three target genes of the JAK-STAT1/2 cellular signaling pathway measured in a sample, the training may preferably be performed as described in detail in the published international patent application WO 2013/011479 A2 ("Assessment of cellular signaling pathway activity using probabilistic modeling of target gene expression").

If the mathematical model is based at least in part on one or more linear combination(s) of expression levels of the at least three target genes of the JAK-STAT1/2 cellular signaling pathway measured in the sample, the training may preferably be performed as described in detail in the published international patent application WO 2014/102668 A2 ("Assessment of cellular signaling pathway activity using linear combination(s) of target gene expressions").

Herein, an exemplary Bayesian network model as shown in FIG. 2 was used to model the transcriptional program of the JAK-STAT1/2 cellular signaling pathway in a simple manner. The model consists of three types of nodes: (a) a transcription factor (TF) element (with states "absent" and "present") in a first layer 1; (b) target genes $TG_1$, $TG_2$, $TG_n$ (with states "down" and "up") in a second layer 2, and; (c) measurement nodes linked to the expression levels of the target genes in a third layer 3. These can be microarray probesets $PS_{1,1}$, $PS_{1,2}$, $PS_{1,3}$, $PS_{2,1}$, $PS_{n,1}$, $PS_{n,m}$ (with states "low" and "high"), as preferably used herein, but could also be other gene expression measurements such as RNAseq or RT-qPCR.

A suitable implementation of the mathematical model, herein, the exemplary Bayesian network model, is based on microarray data. The model describes (i) how the expression levels of the target genes depend on the activation of the TF element, and (ii) how probeset intensities, in turn, depend on the expression levels of the respective target genes. For the latter, probeset intensities may be taken from fRMA pre-processed Affymetrix HG-U133Plus2.0 microarrays, which are widely available from the Gene Expression Omnibus (GEO, www.ncbi.nlm.nih.gov/geo) and ArrayExpress (www.ebi.ac.uk/arrayexpress).

As the exemplary Bayesian network model is a simplification of the biology of a cellular signaling pathway, herein, the JAK-STAT1/2 cellular signaling pathway, and as biological measurements are typically noisy, a probabilistic approach was opted for, i.e., the relationships between (i) the TF element and the target genes, and (ii) the target genes and their respective probesets, are described in probabilistic terms. Furthermore, it was assumed that the activity of the oncogenic cellular signaling pathway which drives tumor growth is not transiently and dynamically altered, but long term or even irreversibly altered. Therefore the exemplary Bayesian network model was developed for interpretation of a static cellular condition. For this reason complex dynamic cellular signaling pathway features were not incorporated into the model.

Once the exemplary Bayesian network model is built and calibrated (see below), the model can be used on microarray data of a new sample by entering the probeset measurements as observations in the third layer 3, and inferring backwards in the calibrated pathway model what the probability must have been for the TF element to be "present". Here, "present" is considered to be the phenomenon that the TF element is bound to the DNA and is controlling transcription of the cellular signaling pathway's target genes, and "absent" the case that the TF element is not controlling transcription. This probability is hence the primary read-out that may be used to indicate activity of the cellular signaling pathway, herein, the JAK-STAT1/2 cellular signaling pathway, which can next be translated into the odds of the cellular signaling pathway being active by taking the ratio of the probability of it being active vs. it being passive (i.e., the odds are given by p/(1−p), where p is the predicted probability of the cellular signaling pathway being active).

In the exemplary Bayesian network model, the probabilistic relations have been made quantitative to allow for a quantitative probabilistic reasoning. In order to improve the generalization behavior across tissue types, the parameters describing the probabilistic relationships between (i) the TF element and the target genes have been carefully hand-picked. If the TF element is "absent", it is most likely that the target gene is "down", hence a probability of 0.95 is chosen for this, and a probability of 0.05 is chosen for the target gene being "up". The latter (non-zero) probability is to account for the (rare) possibility that the target gene is regulated by other factors or that it is accidentally observed as being "up" (e.g. because of measurement noise). If the TF element is "present", then with a probability of 0.70 the target gene is considered "up", and with a probability of 0.30 the target gene is considered "down". The latter values are chosen this way, because there can be several causes why a target gene is not highly expressed even though the TF element is present, e.g., because the gene's promoter region is methylated. In the case that a target gene is not up-regulated by the TF element, but down-regulated, the probabilities are chosen in a similar way, but reflecting the down-regulation upon presence of the TF element. The parameters describing the relationships between (ii) the target genes and their respective probesets have been calibrated on experimental data. For the latter, in this example, microarray data was used from patients samples which are known to have an active JAK-STAT1/2 cellular signaling pathway whereas normal, healthy samples from the same dataset were used as passive JAK-STAT1/2 cellular signaling pathway samples, but this could also be performed using cell line experiments or other patient samples with known cellular signaling pathway activity status. The resulting conditional probability tables are given by:

| A: for upregulated target genes | | |
|---|---|---|
|  | $PS_{i,j}$ = low | $PS_{i,j}$ = high |
| $TG_i$ = down | $\dfrac{AL_{i,j} + 1}{AL_{i,j} + AH_{i,j} + 2}$ | $\dfrac{AH_{i,j} + 1}{AL_{i,j} + AH_{i,j} + 2}$ |
| $TG_i$ = up | $\dfrac{PL_{i,j} + 1}{PL_{i,j} + PH_{i,j} + 2}$ | $\dfrac{PH_{i,j} + 1}{PL_{i,j} + PH_{i,j} + 2}$ |

| B: for downregulated target genes | | |
|---|---|---|
|  | $PS_{i,j}$ = low | $PS_{i,j}$ = high |
| $TG_i$ = down | $\dfrac{PL_{i,j} + 1}{PL_{i,j} + PH_{i,j} + 2}$ | $\dfrac{PH_{i,j} + 1}{PL_{i,j} + PH_{i,j} + 2}$ |
| $TG_i$ = up | $\dfrac{AL_{i,j} + 1}{AL_{i,j} + AH_{i,j} + 2}$ | $\dfrac{AH_{i,j} + 1}{AL_{i,j} + AH_{i,j} + 2}$ |

In these tables, the variables $AL_{i,j}$, $AH_{i,j}$, $PL_{i,j}$, and $PH_{i,j}$ indicate the number of calibration samples with an "absent" (A) or "present" (P) transcription complex that have a "low" (L) or "high" (H) probeset intensity, respectively. Dummy counts have been added to avoid extreme probabilities of 0 and 1.

To discretize the observed probeset intensities, for each probeset $PS_{i,j}$ a threshold $t_{i,j}$ was used, below which the observation is called "low", and above which it is called "high". This threshold has been chosen to be the (weighted) median intensity of the probeset in the used calibration dataset. Due to the noisiness of microarray data, a fuzzy method was used when comparing an observed probeset intensity to its threshold, by assuming a normal distribution with a standard deviation of 0.25 (on a log 2 scale) around the reported intensity, and determining the probability mass below and above the threshold.

If instead of the exemplary Bayesian network described above, a (pseudo-)linear model as described in Example 1 above is employed, the weights indicating the sign and magnitude of the correlation between the nodes and a threshold to call whether a node is either "absent" or "present" would need to be determined before the model could be used to infer cellular signaling pathway activity in a test sample. One could use expert knowledge to fill in the weights and the threshold a priori, but typically the model would be trained using a representative set of training samples, of which preferably the ground truth is known, e.g., expression data of probesets in samples with a known "present" transcription factor complex (=active cellular signaling pathway) or "absent" transcription factor complex (=passive cellular signaling pathway).

Known in the field are a multitude of training algorithms (e.g., regression) that take into account the model topology and changes the model parameters, here, the weights and the threshold, such that the model output, here, a weighted linear score, is optimized. Alternatively, it is also possible to calculate the weights directly from the expression observed levels without the need of an optimization algorithm.

A first method, named "black and white"-method herein, boils down to a ternary system, in which each weight is an element of the set $\{-1, 0, 1\}$. If this is put in a biological context, the −1 and 1 correspond to target genes or probesets that are down- and up-regulated in case of cellular signaling pathway activity, respectively. In case a probeset or target gene cannot be statistically proven to be either up- or down-regulated, it receives a weight of 0. In one example, a left-sided and right-sided, two sample t-test of the expression levels of the active cellular signaling pathway samples versus the expression levels of the samples with a passive cellular signaling pathway can be used to determine whether a probe or gene is up- or down-regulated given the used training data. In cases where the average of the active samples is statistically larger than the passive samples, i.e., the p-value is below a certain threshold, e.g., 0.3, the target gene or probeset is determined to be up-regulated. Conversely, in cases where the average of the active samples is statistically lower than the passive samples, the target gene or probeset is determined to be down-regulated upon activation of the cellular signaling pathway. In case the lowest p-value (left- or right-sided) exceeds the aforementioned threshold, the weight of the target gene or probeset can be defined to be 0.

A second method, named "log odds"-weights herein, is based on the logarithm (e.g., base e) of the odds ratio. The odds ratio for each target gene or probeset is calculated based on the number of positive and negative training samples for which the probeset/target gene level is above and below a corresponding threshold, e.g., the (weighted) median of all training samples. A pseudo-count can be added to circumvent divisions by zero. A further refinement is to count the samples above/below the threshold in a somewhat more probabilistic manner, by assuming that the probeset/target gene levels are e.g. normally distributed around its observed value with a certain specified standard deviation (e.g., 0.25 on a 2-log scale), and counting the probability mass above and below the threshold. Herein, an odds ratio calculated in combination with a pseudo-count and using probability masses instead of deterministic measurement values is called a "soft" odds ratio.

Further details regarding the determining of cellular signaling pathway activity using mathematical modeling of target gene expression can be found in Verhaegh W. et al., "Selection of personalized patient therapy through the use of knowledge-based computational models that identify tumor-driving signal transduction pathways", Cancer Research, Vol. 74, No. 11, 2014, pages 2936 to 2945.

Herein, we have used publically available mRNA expression data from Affymetrix U133Plus2.0 of blood monocytes from healthy donors which were stimulated in vitro by cytokines: IFNα2a (IFN type I) and IFNγ (IFN type II). Because the STAT1/2 pathway can be activated by either IFN type I or by IFN type II, with slightly different effects on the target gene expression levels, two different calibration data sets were used, representative for the two ways of STAT1/2 activation, being defined as stimulation with respectively IFN type I and IFN type II stimuli. Blood monocytes from healthy donors without any stimulation form the control group. Hence, two different models were separately calibrated on calibration samples with either IFNα2a stimulation (IFN type I) or IFNγ stimulation (IFN type II), using the same target gene list (see Table 1).

Figure 9:
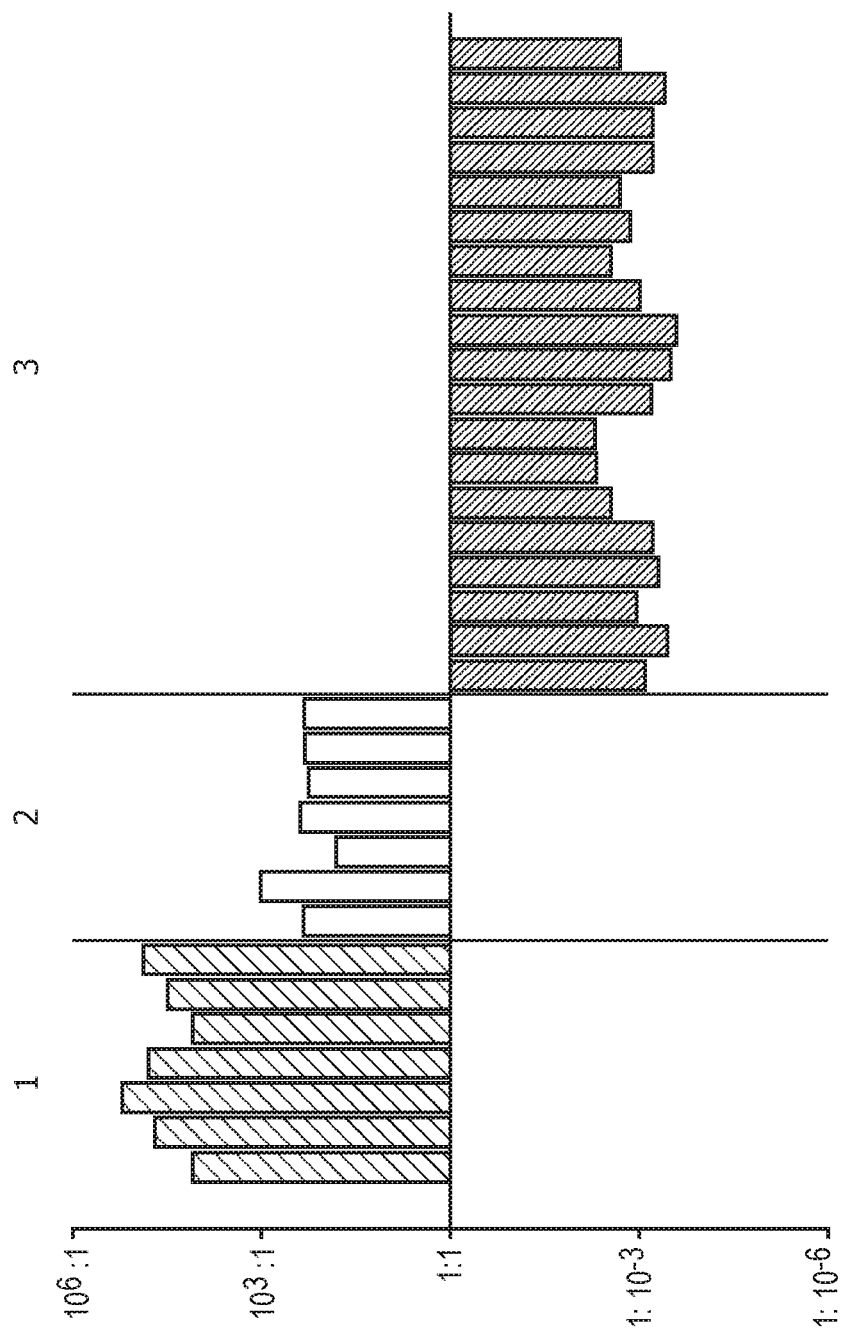
FIG. 9 shows IFN type I calibration results of the Bayesian network model based on the evidence curated list of target genes (23 target genes list) from Table 1 and the methods as described herein using publically available expression data sets of blood monocytes from 11 healthy donors from data set GSE38351.
Figure 10:
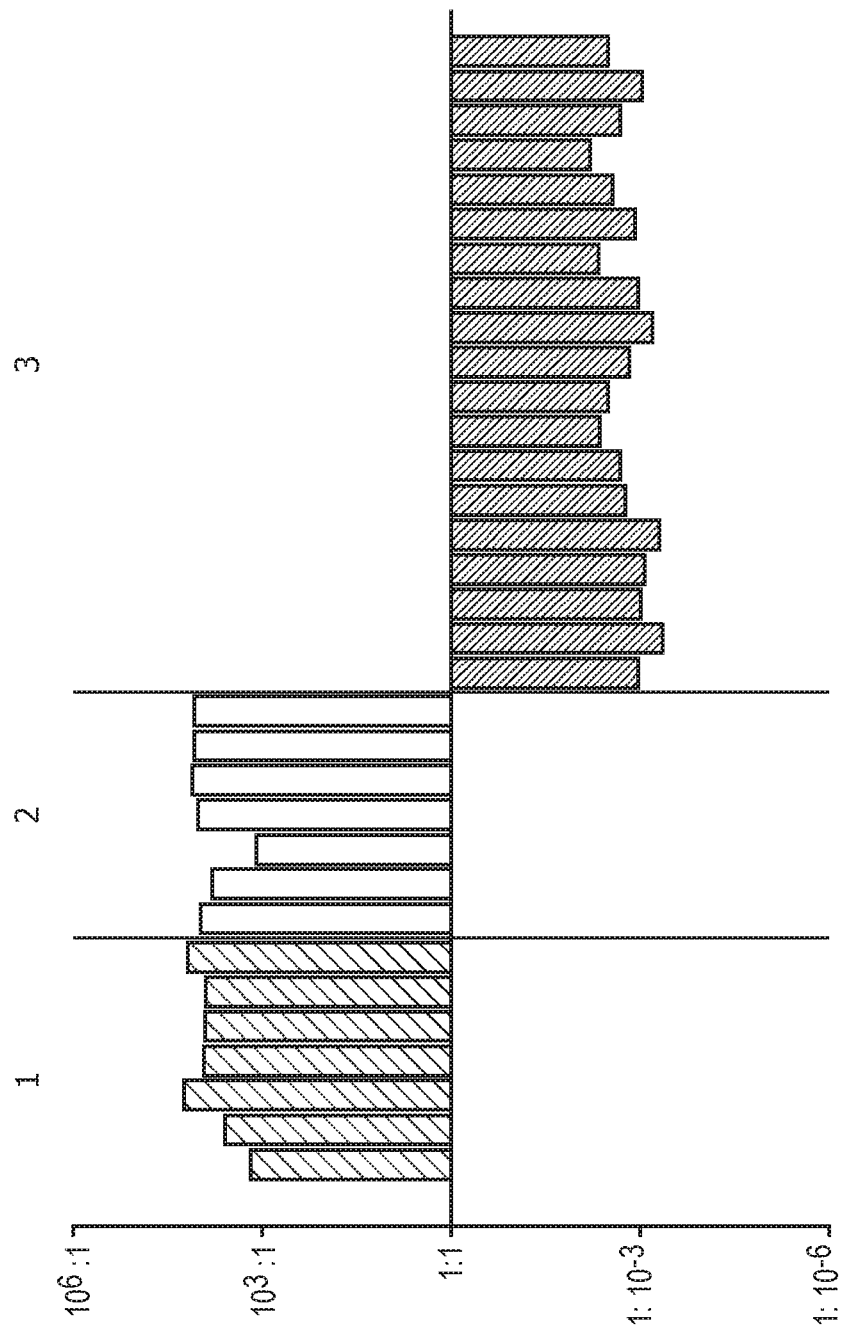
FIG. 10 shows IFN type II calibration results of the Bayesian network model based on the evidence curated list of target genes (23 target genes list) from Table 1 and the methods as described herein using publically available expression data sets of blood monocytes from 11 healthy donors from data set GSE38351.

In the following, calibration results of the Bayesian network model on data sets with IFN type I stimulation and IFN type 2 simulation are shown in FIGS. 9 and 10.

FIG. 9 shows IFN type I calibration results of the Bayesian network model based on the evidence curated list of target genes (23 target genes list) from Table 1 and the methods as described herein using publically available expression data sets of blood monocytes from 11 healthy donors from data set GSE38351. 19 samples, including 11 samples with blood monocytes incubated without any stimulation and 8 samples blood with monocytes that were isolated immediately after drawing blood, are used as control group, i.e., an inactive calibration samples (group 3). The training group, i.e., the active calibration samples, included 7 samples stimulated with IFNα2a (IFN type I; group 1). The model was tested on another 7 samples from the same donors stimulated with IFNγ (IFN type II; group 2). In the diagram, the vertical axis indicates the odds that the TF element is "present" resp. "absent", which corresponds to the JAK-STAT1/2 cellular signaling pathway being active resp. passive, wherein values above the horizontal axis correspond to the TF element being more likely "present"/active and values below the horizontal axis indicate that the odds that the TF element is "absent"/passive are larger than the odds that it is "present"/active. The JAK-STAT1/2 IFN type I model was able to separate clearly the inactive from the active calibration samples.

FIG. 10 shows IFN type II calibration results of the Bayesian network model based on the evidence curated list of target genes (23 target genes list) from Table 1 and the methods as described herein using publically available expression data sets of blood monocytes from 11 healthy donors from data set GSE38351. 19 samples, including 11 samples with blood monocytes incubated without any stimulation and 8 samples blood with monocytes that were isolated immediately after drawing blood, are used as control group, i.e., the inactive calibration samples (group 3). The training group, i.e., the active calibration samples, included 7 samples stimulated with IFNγ (IFN type II; group 1). The model was tested on another 7 samples from the same donors stimulated with IFNα2a (IFN type I; group 2). In the diagram, the vertical axis indicates the odds that the TF element is "present" resp. "absent", which corresponds to the JAK-STAT1/2 cellular signaling pathway being active resp. passive, wherein values above the horizontal axis correspond to the TF element being more likely "present"/active and values below the horizontal axis indicate that the odds that the TF element is "absent"/passive are larger than the odds that it is "present"/active. The JAK-STAT1/2 IFN type II model was able to separate clearly the inactive from the active calibration samples.

By comparing the pathway activity levels between the JAK-STAT1/2 IFN type I model (FIG. 9) and the JAK-STAT1/2 IFN type II model (FIG. 10) on identical samples, one can infer whether JAK-STAT1/2 activity is induced by type I or by type II stimulation. For the samples stimulated with IFNα2a (IFN type I; group 1), the type I model activity scores in FIG. 9 are higher than the type II model activity scores in FIG. 10, clearly agreeing with their IFN type I stimulation. For the samples stimulated with IFNγ (IFN type II; group 2), the JAK-STAT1/2 IFN type II model activity scores in FIG. 10 are higher than the JAK-STAT1/2 IFN type I model activity scores in FIG. 9, agreeing with their IFN type II stimulation. For samples with unknown stimulation, such a comparison can indicate which type of stimulation has triggered JAK-STAT1/2 activation.

In the following, validation results of the trained exemplary Bayesian network model using the evidence curated list of target genes (23 target genes list) of Table 1 are shown in FIGS. 11 to 16.

Figure 11:
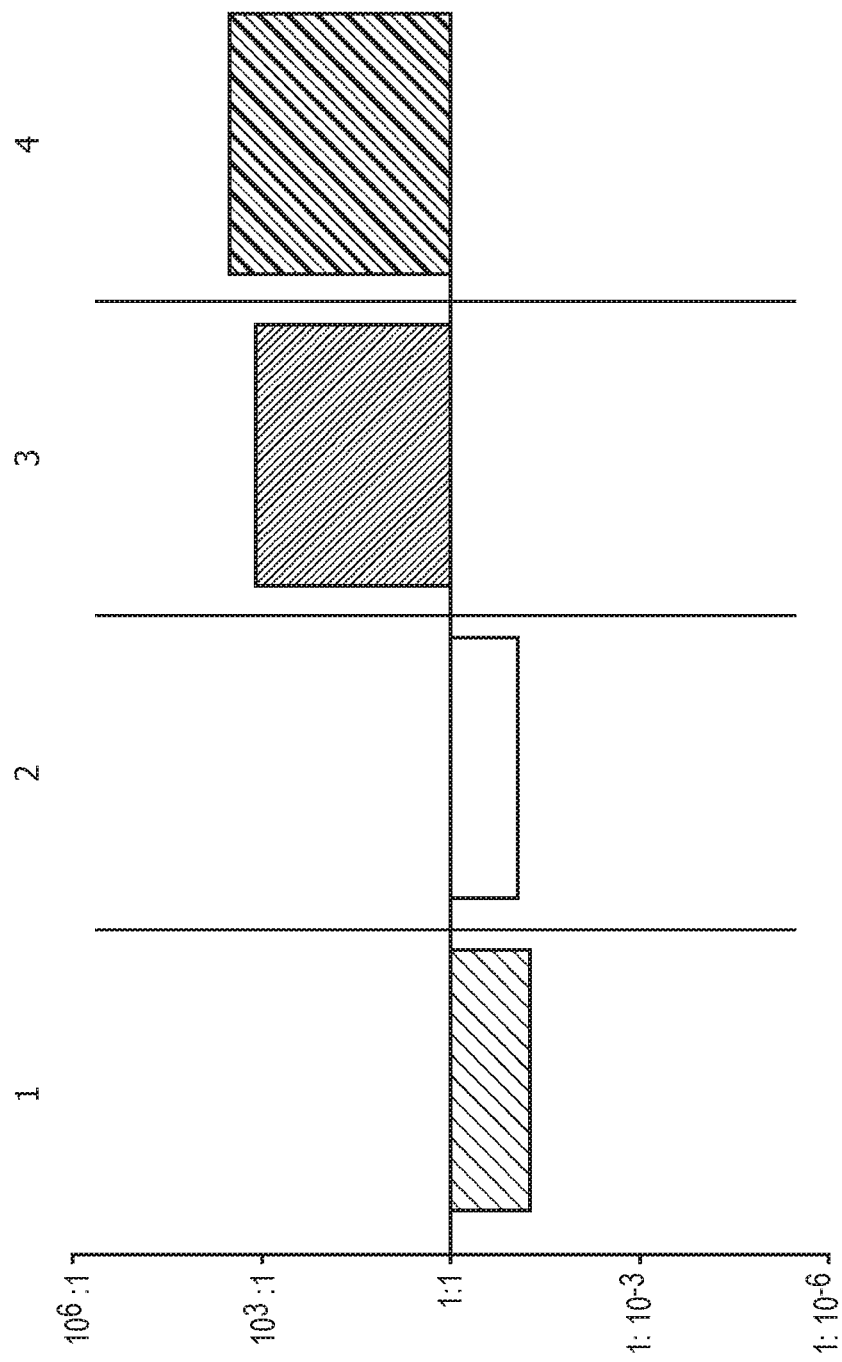
FIG. 11 shows JAK-STAT1/2 cellular signaling pathway activity predictions of the trained exemplary IFN type I Bayesian network model using the evidence curated list of target genes (23 target genes list) from Table 1.

FIG. 11 shows JAK-STAT1/2 cellular signaling pathway activity predictions of the trained exemplary IFN type I Bayesian network model using the evidence curated list of target genes (23 target genes list) from Table 1. NK cells of peripheral blood mononuclear cells (PBMC) of five healthy controls have been isolated either directly (group 1) or after culturing for 6 h without stimulation (group 2) (data set GSE15743). With 6 hours of stimulation with 100 ng/ml and 1 ng/ml recombinant IFNα-2b (IFN type I stimulus) (group 3 and group 4, respectively), JAK-STAT1/2 is activated. In the diagram, the vertical axis indicates the odds that the TF element is "present" resp. "absent", which corresponds to the JAK-STAT1/2 cellular signaling pathway being active resp. passive, wherein values above the horizontal axis correspond to the TF element being more likely "present"/active and values below the horizontal axis indicate that the odds that the TF element is "absent"/passive are larger than the odds that it is "present"/active. The JAK-STAT1/2 IFN type I model correctly predicts high JAK-STAT1/2 activity for samples with IFNα-2b (IFN type I) stimulation, and samples stimulated with high dose IFNα-2b having high pathway activity as well.

Figure 12:
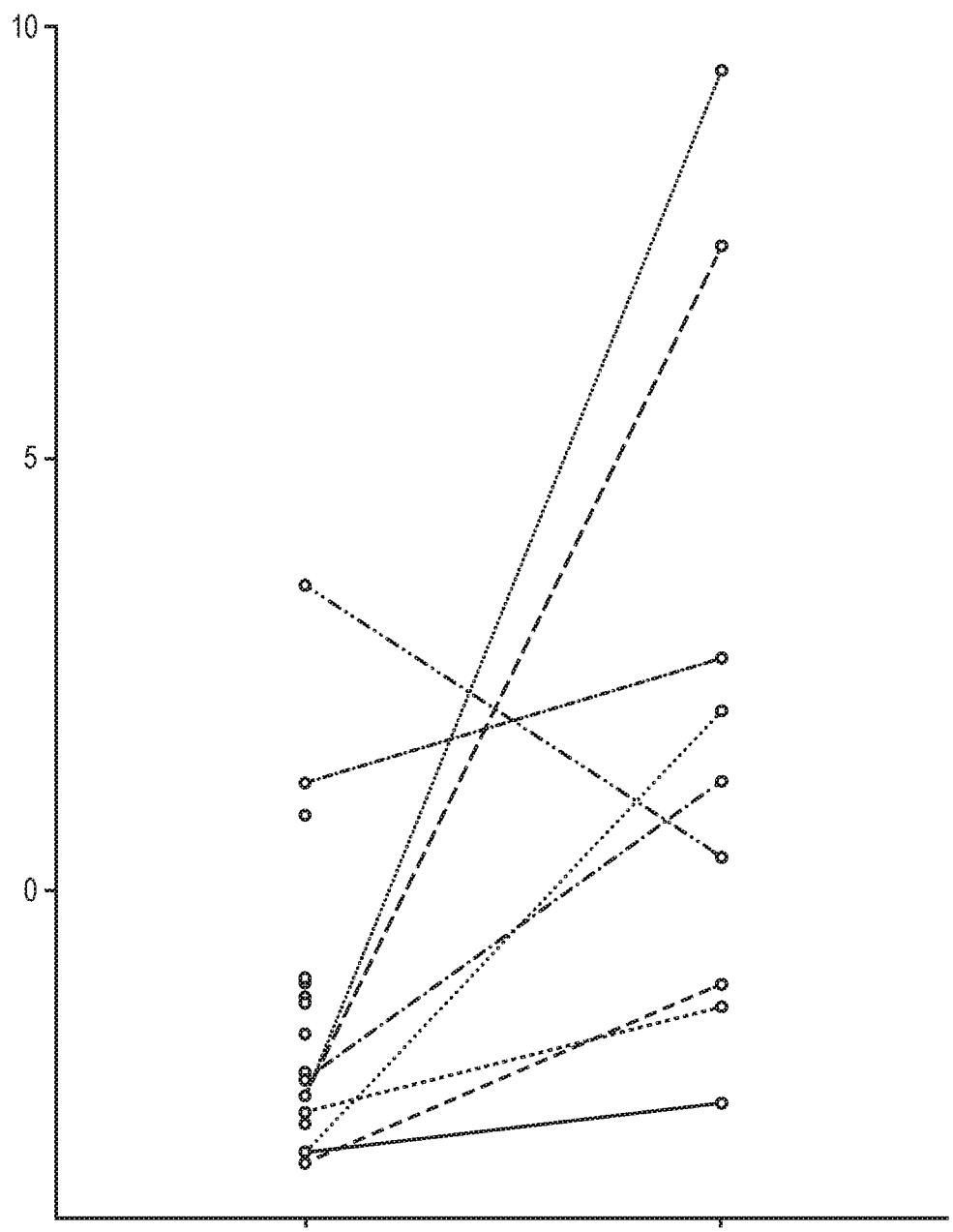
FIG. 12 shows JAK-STAT1/2 cellular signaling pathway activity predictions of the trained exemplary IFN type I Bayesian network model using the evidence curated list of target genes (23 target genes list) from Table 1.

FIG. 12 shows JAK-STAT1/2 cellular signaling pathway activity predictions of the trained exemplary IFN type I Bayesian network model using the evidence curated list of target genes (23 target genes list) from Table 1. Plasmacytoid dendritic cells (pDCs) were separated from healthy donors and MS (Multiple Sclerosis) patients before and after initiation of treatment with IFN-β (IFN type I) (data set GSE37750). In the diagram, the single dots on the left side of the graph represent healthy donors that are in the control group. As can be seen from the activity values given in log 2(odds) on the vertical axis of the graph, the samples from the control group are JAK-STAT1/2 inactive. In contrast, the connected dots represent the STAT1/2 activity values of 9 patients with MS before treatment (left side of the graph) and after treatment (right side of the graph). Each line connects the STAT1/2 activity before and after treatment for each patient, which shows that STAT1/2 activities are significantly higher after treatment for 8 patients. The JAK-STAT1/2 IFN type I model correctly predicts that JAK-STAT1/2 activity levels increase after treatment with IFN-β.

Figure 13:
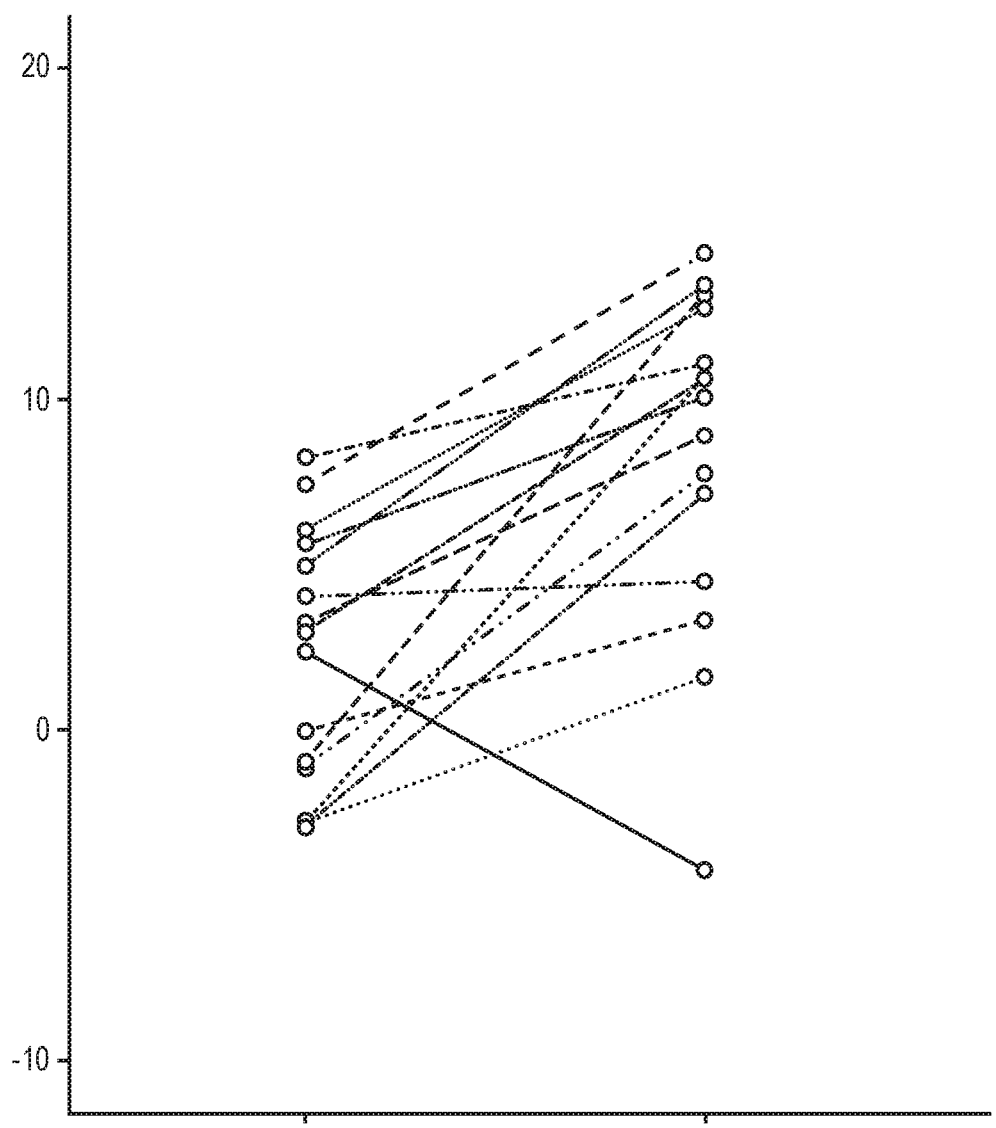
FIG. 13 shows JAK-STAT1/2 cellular signaling pathway activity predictions of the trained exemplary IFN type I Bayesian network model using the evidence curated list of target genes (23 target genes list) from Table 1.

FIG. 13 shows JAK-STAT1/2 cellular signaling pathway activity predictions of the trained exemplary IFN type I Bayesian network model using the evidence curated list of target genes (23 target genes list) from Table 1. In data set GSE14386, peripheral blood mononuclear cells (PBMCs) were derived from patients with so called "clinically isolated syndrome (CIS)", suggestive for the diagnosis of multiple sclerosis (MS), and stimulated with plate-immobilized αCD3 (1 µg/ml) and αCD28 (5 µg/ml) mAb (BD Biosciences) in the absence (group 1) or presence (group 2) of IFNβ-1α (IFN type I) (1000 U/ml) for 24 hours. In the diagram, the connected dots represent the STAT1/2 activity values of 14 patients with a CIS before treatment (left side of the graph) and after treatment (right side of the graph). The results show that STAT1/2 activities are significantly higher after treatment for all 14 patients. The JAK-STAT1/2 IFN type I model correctly predicts that JAK-STAT1/2 activity levels increase after incubation with IFNβ-1α (IFN type I).

Figure 14:
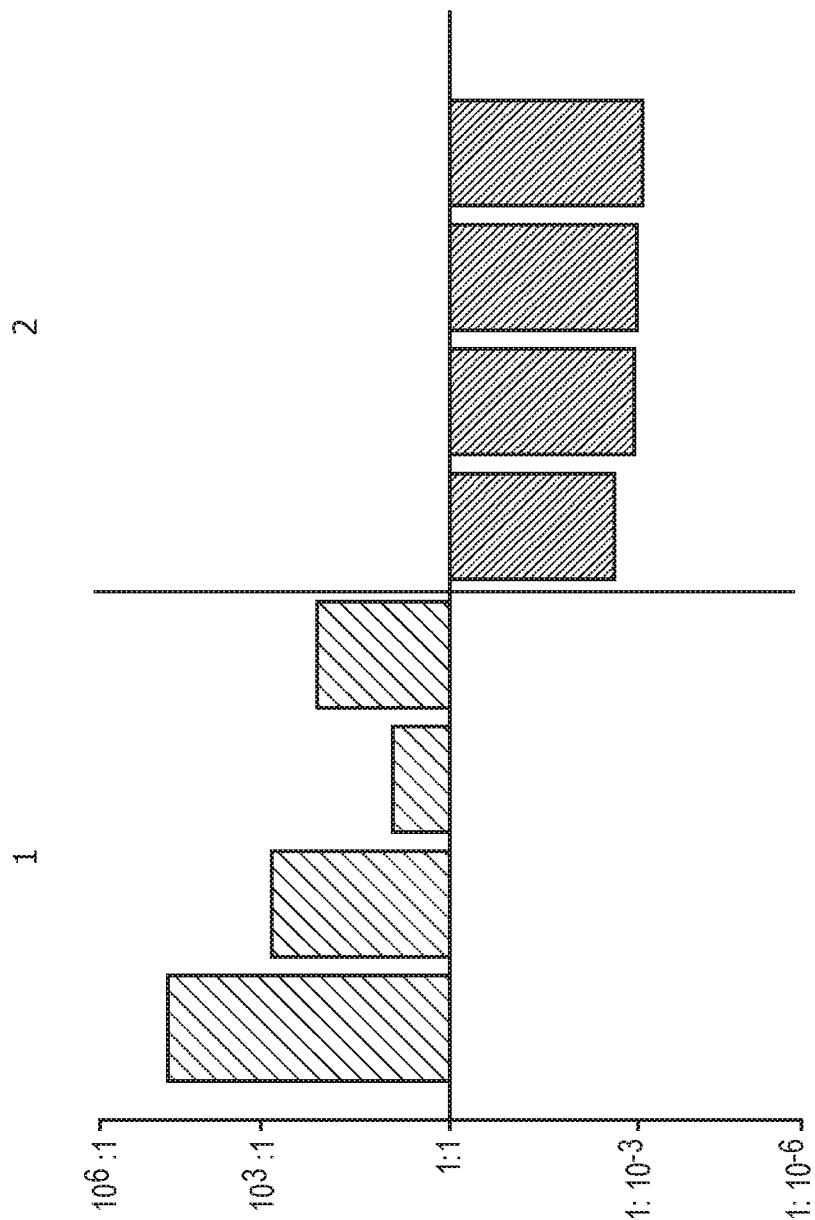
FIG. 14 shows JAK-STAT1/2 cellular signaling pathway activity predictions of the trained exemplary IFN type II Bayesian network model using the evidence curated list of target genes (23 target genes list) from Table 1.

FIG. 14 shows JAK-STAT1/2 cellular signaling pathway activity predictions of the trained exemplary IFN type II Bayesian network model using the evidence curated list of target genes (23 target genes list) from Table 1. Dendritic cells (DCs) were matured for 6 hours with Toll-like receptor (TLR) 4 in the presence of IFNγ (IFN type II) in data set GSE11327. RNA of DCs was isolated after 6, 12, 24, or 48 hours of maturation (group 1; the four bars represent four sequential points in time: 6, 12, 24, 48 hours). In the diagram, the vertical axis indicates the odds that the TF element is "present" resp. "absent", which corresponds to the JAK-STAT1/2 cellular signaling pathway being active resp. passive, wherein values above the horizontal axis correspond to the TF element being more likely "present"/active and values below the horizontal axis indicate that the odds that the TF element is "absent"/passive are larger than the odds that it is "present"/active. The JAK-STAT1/2 IFN type II model correctly predicts higher JAK-STAT activity levels in the DCs (group 1) and inactive STAT1/2 in the unstimulated control group (group 2).

Figure 15:
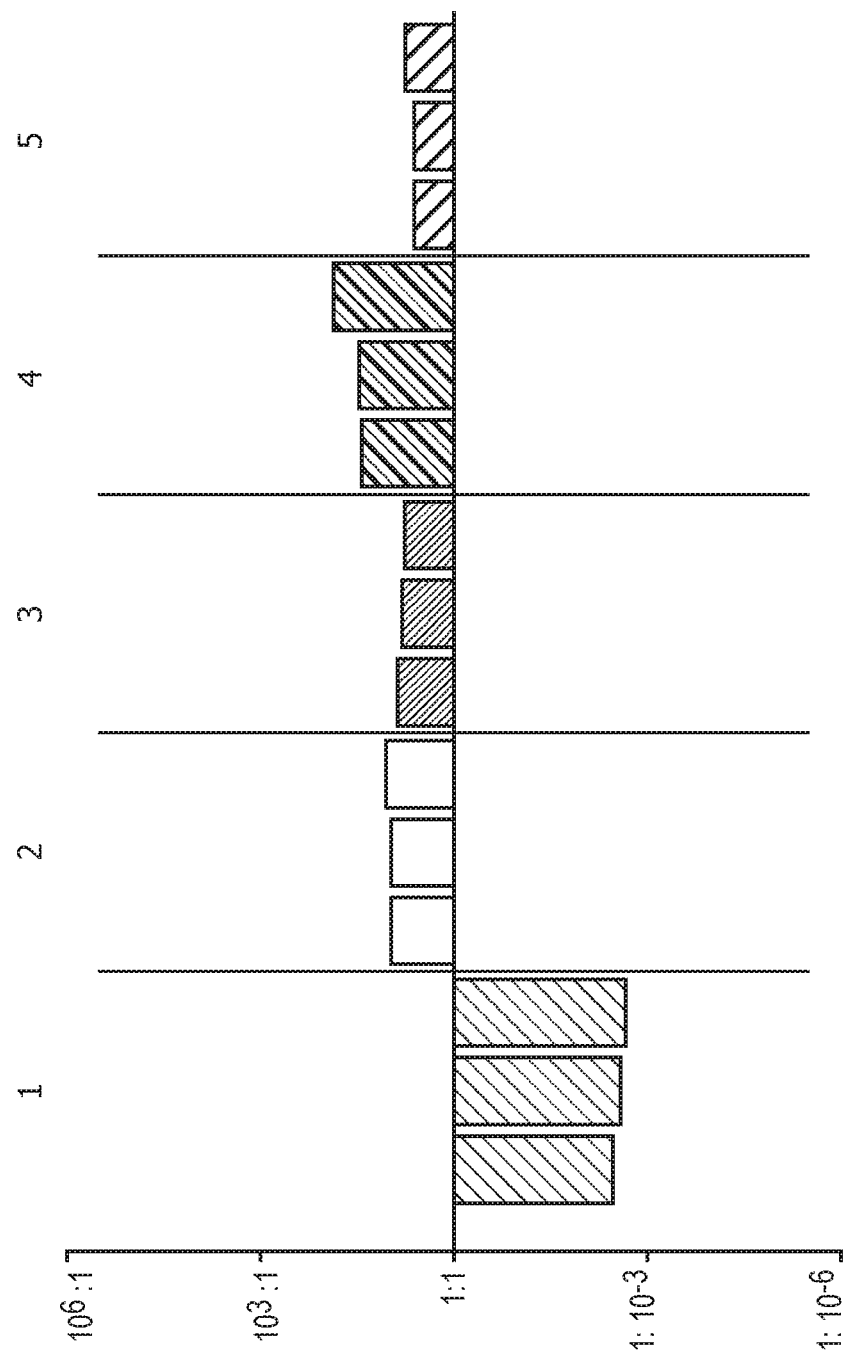
FIG. 15 shows JAK-STAT1/2 cellular signaling pathway activity predictions of the trained exemplary IFN type II Bayesian network model using the evidence curated list of target genes (23 target genes list) from Table 1.

FIG. 15 shows JAK-STAT1/2 cellular signaling pathway activity predictions of the trained exemplary IFN type II Bayesian network model using the evidence curated list of target genes (23 target genes list) from Table 1. THP1-SP110b cells were treated with IFNγ (type II IFN) in data set GSE58096. In the diagram, the vertical axis indicates the odds that the TF element is "present" resp. "absent", which corresponds to the JAK-STAT1/2 cellular signaling pathway being active resp. passive, wherein values above the horizontal axis correspond to the TF element being more likely "present"/active and values below the horizontal axis indicate that the odds that the TF element is "absent"/passive are larger than the odds that it is "present"/active. The JAK-STAT1/2 IFN type II model correctly predicts higher JAK-STAT activity levels in the cells that were treated with IFNγ (IFN type II) for 2 days (group 2), cells that were treated with Dox plus IFNγ for 2 days (group 3), cells that were treated with IFNγ for 4 days (group 4), and cells that were treated with Dox plus IFNγ for 4 days (group 5), compared to the untreated control group (group 1).

Figure 16:
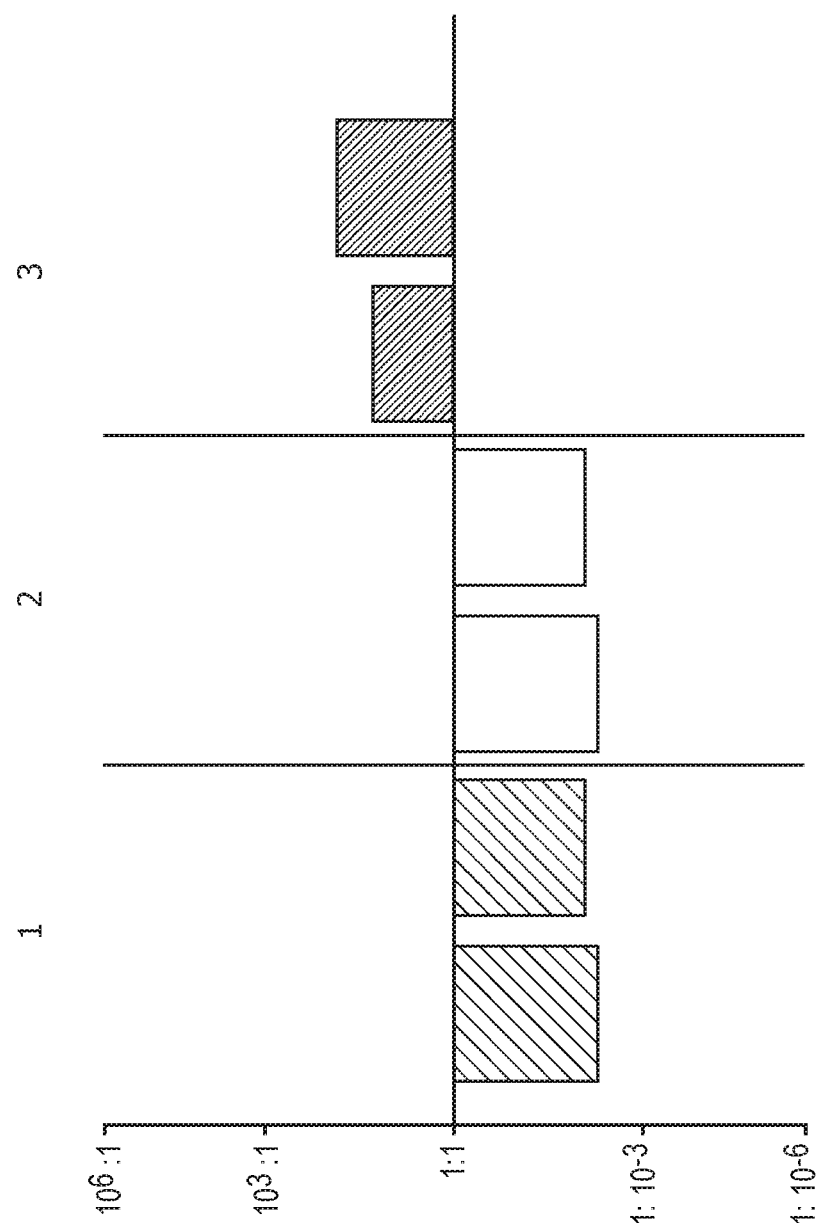
FIG. 16 shows JAK-STAT1/2 cellular signaling pathway activity predictions of the trained exemplary IFN type II Bayesian network model using the evidence curated list of target genes (23 target genes list) from Table 1.

FIG. 16 shows JAK-STAT1/2 cellular signaling pathway activity predictions of the trained exemplary IFN type II Bayesian network model using the evidence curated list of target genes (23 target genes list) from Table 1. Peripheral blood mononuclear cells were cultured in RPMI 1640 supplemented with 10% fetal bovine serum and 10 ng/mL M-CSF in the presence or absence of 100 U/mL IFNγ for 24 h (data set GSE11864). In the diagram, the vertical axis indicates the odds that the TF element is "present" resp. "absent", which corresponds to the JAK-STAT1/2 cellular signaling pathway being active resp. passive, wherein values above the horizontal axis correspond to the TF element being more likely "present"/active and values below the horizontal axis indicate that the odds that the TF element is "absent"/passive are larger than the odds that it is "present"/active. The JAK-STAT1/2 IFN type II model correctly predicts that JAK-STAT1/2 is inactive in fresh blood monocytes (group 1) and in the cells that were cultured in M-CSF (group 2), whereas cells that were stimulated with IFNγ show high JAK-STAT1/2 activity levels (group 3).

Figure 17:
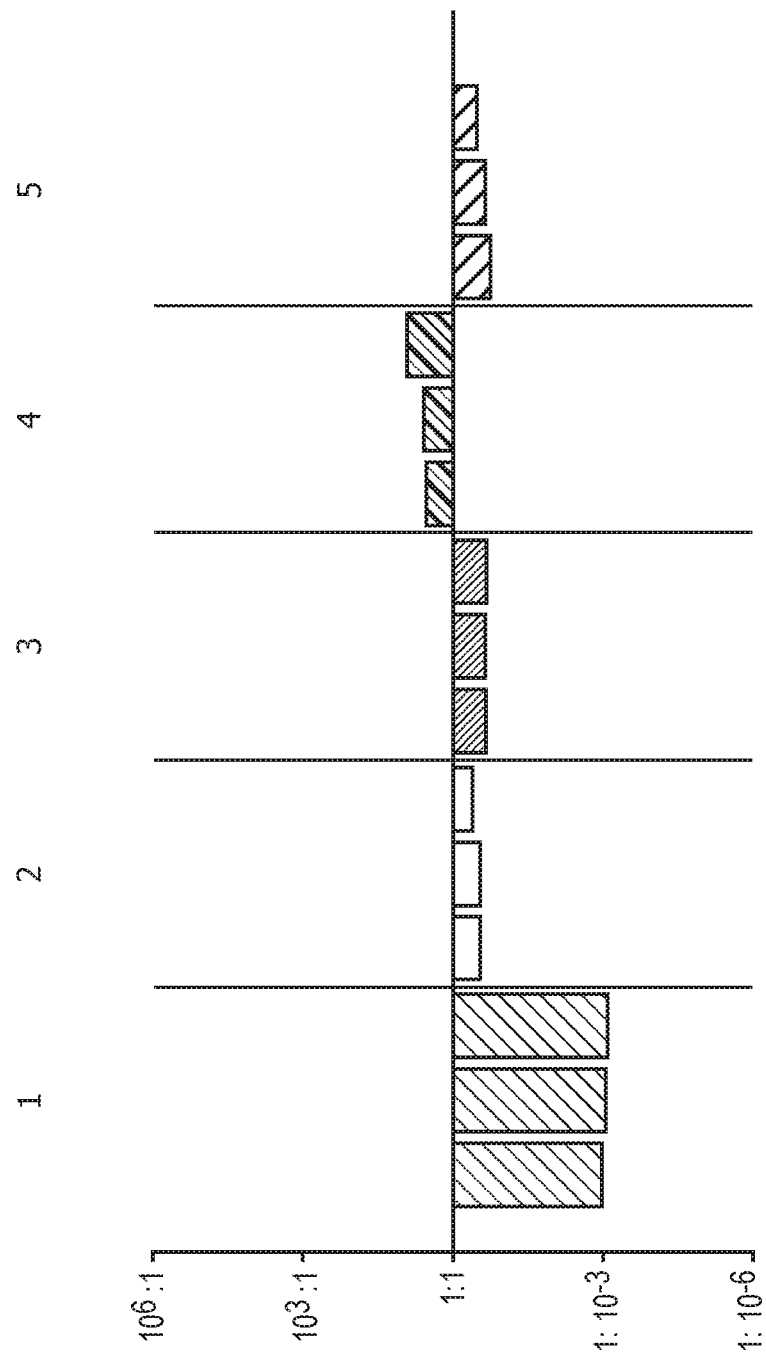
FIG. 17 shows JAK-STAT1/2 cellular signaling pathway activity predictions of the trained exemplary IFN type I Bayesian network model using the evidence curated list of target genes (23 target genes list) from Table 1.
Figure 18:
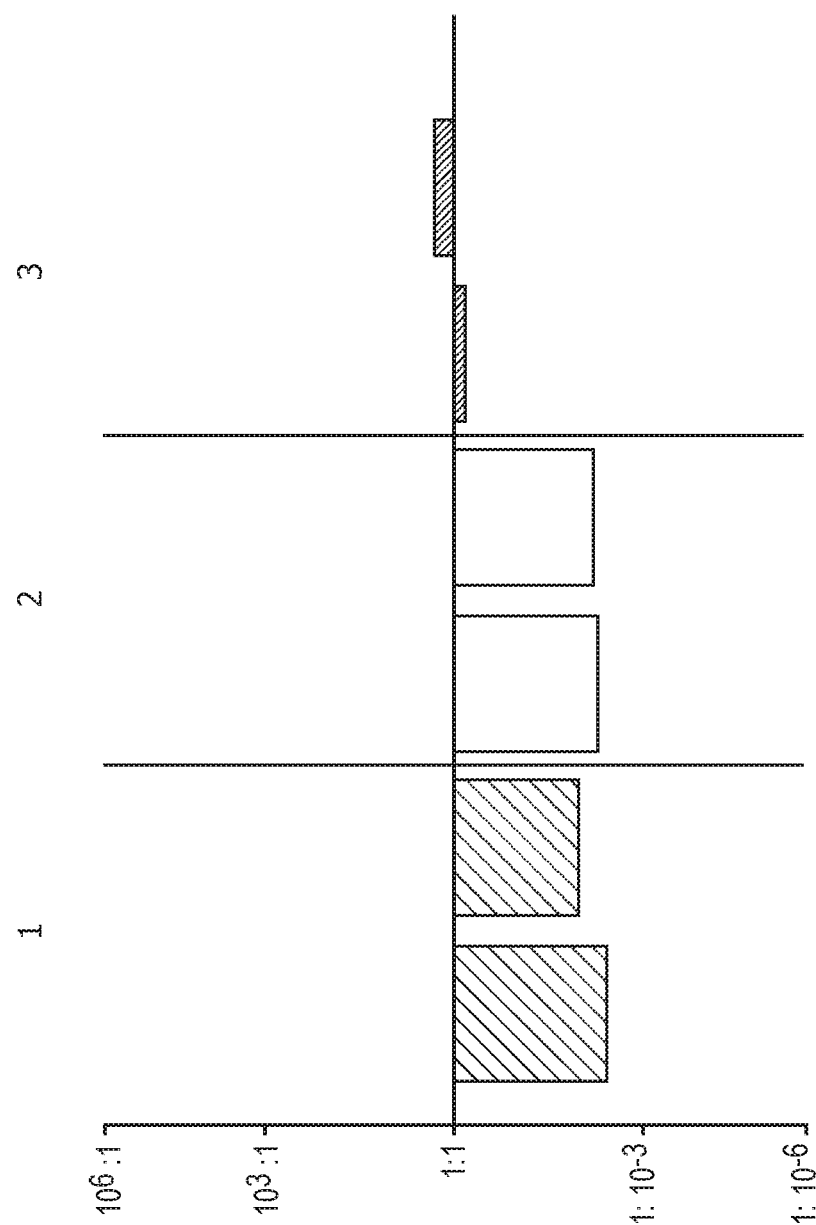
FIG. 18 shows JAK-STAT1/2 cellular signaling pathway activity predictions of the trained exemplary IFN type I Bayesian network model using the evidence curated list of target genes (23 target genes list) from Table 1.

Further validation results of the trained exemplary Bayesian network model using the evidence curated list of target genes (23 target genes list) are shown in FIGS. 17 and 18. Here, the JAK-STAT1/2 IFN type I model and the JAK-STAT1/2 IFN type II model were applied to the same data sets in order to investigate differences in the JAK-STAT1/2 cellular signaling pathway activity prediction results.

FIG. 17 shows JAK-STAT1/2 cellular signaling pathway activity predictions of the trained exemplary IFN type I Bayesian network model using the evidence curated list of target genes (23 target genes list) from Table 1. The IFN type I calibrated JAK-STAT1/2 Bayesian network model was applied to the same data set GSE58096 as in FIG. 15, with five groups representing the same samples. In the diagram, the vertical axis indicates the odds that the TF element is "present" resp. "absent", which corresponds to the JAK-STAT1/2 cellular signaling pathway being active resp. passive, wherein values above the horizontal axis correspond to the TF element being more likely "present"/active and values below the horizontal axis indicate that the odds that the TF element is "absent"/passive are larger than the odds that it is "present"/active. The JAK-STAT1/2 IFN type I model predicted activity levels of IFNγ-induced JAK-STAT1/2 activity at a lower activity level compared to the IFN type II-calibrated JAK-STAT1/2 model. In the prediction result from the JAK-STAT1/2 IFN type II model in FIG. 15, four groups, which were treated with IFNγ, were considered to be active, while here only one group is considered to be active, which is the cells treated with IFNγ for 4 days (group 4), whereas JAK-STAT1/2 is considered to be inactive based on the JAK-STAT1/2 IFN type I model for cells that were treated with IFNγ for 2 days (group 2), cells that were treated with Dox plus IFNγ for 2 days (group 3), and cells that were treated with Dox plus IFNγ for 4 days (group 5). This is a good example to prove that separately calibrated JAK-STAT1/2 models on respectively IFN type I and type II induced cell models can distinguish between STAT 1/2 activity that is induced by respectively IFN type I and IFN type II, because the JAK-STAT1/2 IFN type II model results in FIG. 15 show higher activity levels for groups 2 to 5 than the JAK-STAT1/2 IFN type I model in FIG. 17.

FIG. 18 shows JAK-STAT1/2 cellular signaling pathway activity predictions of the trained exemplary IFN type I Bayesian network model using the evidence curated list of target genes (23 target genes list) from Table 1. The IFN type I calibrated JAK-STAT1/2 Bayesian network model was applied to the same data set GSE11864 as in FIG. 16, with three groups representing the same samples. In the diagram, the vertical axis indicates the odds that the TF element is "present" resp. "absent", which corresponds to the JAK-STAT1/2 cellular signaling pathway being active resp. passive, wherein values above the horizontal axis correspond to the TF element being more likely "present"/active and values below the horizontal axis indicate that the odds that the TF element is "absent"/passive are larger than the odds that it is "present"/active. While the JAK-STAT1/2 IFN type I model clearly shows higher activity in the samples in group 3 compared to groups 1 and 2, a comparison of the activity scores for the samples in group 3 between the type I model and the type II model from FIG. 16 reveals a higher activity score for the latter model, indicating that the samples from group 3 correspond to an IFN type II activation of JAK-STAT1/2.

Figure 19:
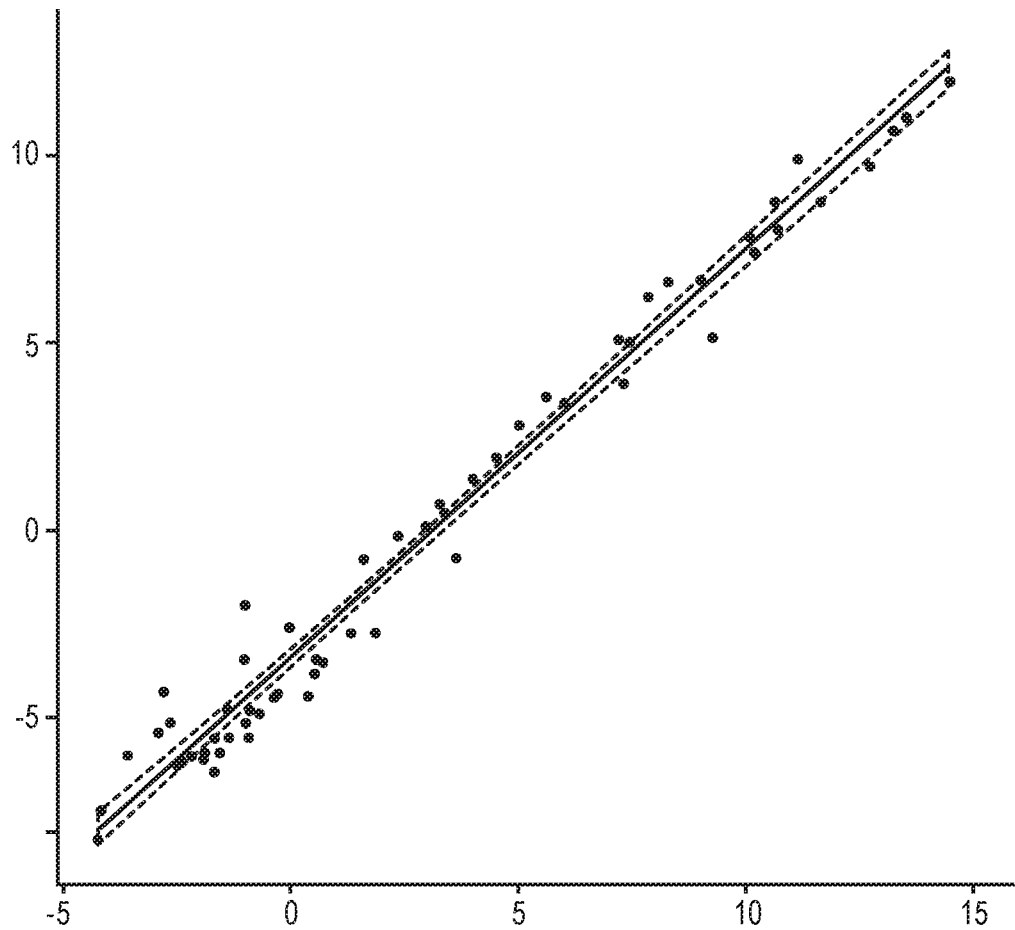
FIG. 19 shows the correlation between the trained exemplary IFN type I Bayesian network model using the evidence curated list of target genes (23 target genes list) from Table 1 and the 9 target gene shortlist from Table 2, respectively.
Figure 20:
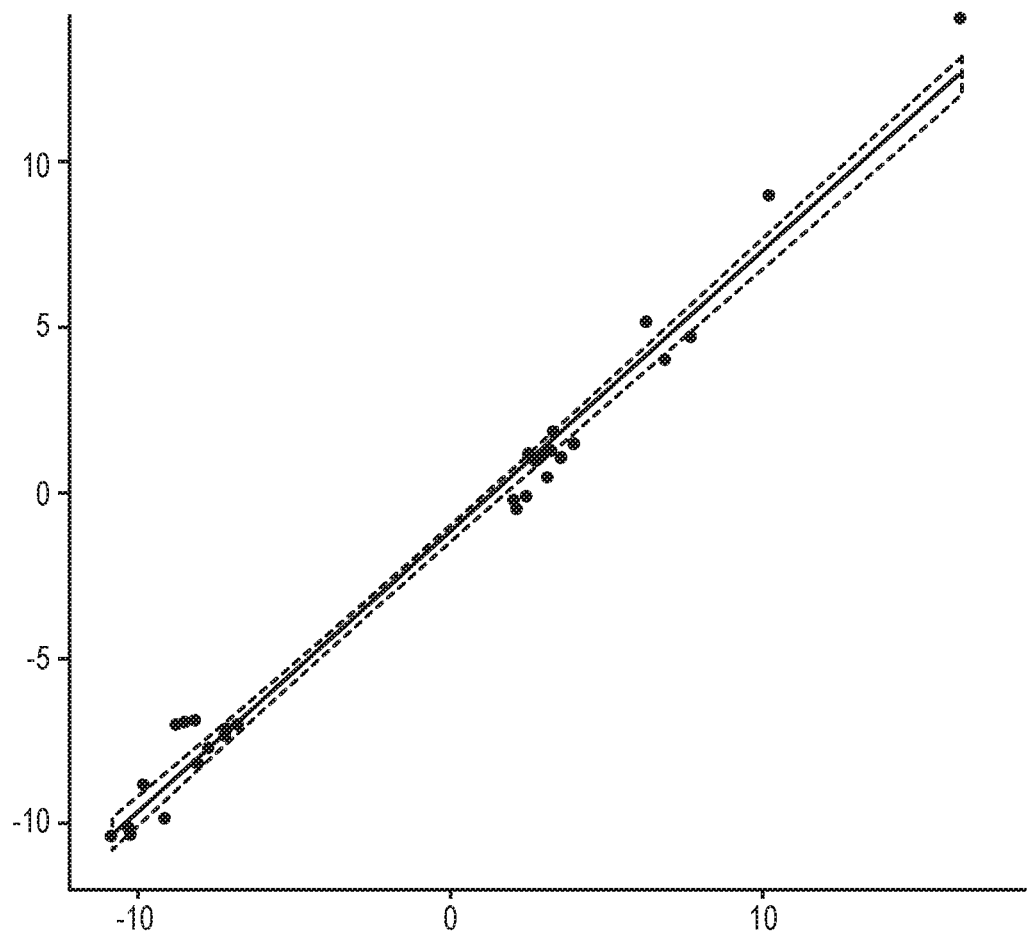
FIG. 20 shows the correlation between the trained exemplary IFN type II Bayesian network model using the evidence curated list of target genes (23 target genes list) from Table 1 and the 9 target gene shortlist from Table 2, respectively.

Further validation results of the trained exemplary Bayesian network models using the evidence curated list of target genes (23 target genes list) from Table 1 and the 9 target gene shortlist from Table 2 are shown in FIGS. 19 and 20. Here, the evidence curated list of target genes (23 target genes list) of Table 1 is compared with the 9 target gene shortlist of Table 2 for the same data sets for both the both the JAK-STAT1/2 IFN type I model and the JAK-STAT1/2 IFN type II model.

FIG. 19 shows the correlation between the trained exemplary IFN type I Bayesian network model using the evidence curated list of target genes (23 target genes list) from Table 1 and the 9 target gene shortlist from Table 2, respectively. In the diagram, the horizontal axis indicates the odds (on a log 2 scale) that the TF element is "present" resp. "absent", which corresponds to the JAK-STAT1/2 cellular signaling pathway being active resp. passive, as predicted by the trained exemplary IFN type I Bayesian network model using the evidence curated list of target genes (23 target genes list) from Table 1. The vertical axis indicates the same information, as predicted by the trained exemplary IFN type I Bayesian network model using the 9 target gene shortlist from Table 2 (data sets GSE15743, GSE37750, GSE14386). The two models are significantly correlated with a p-value of 2.2e-16 and a correlation coefficient of 0.988.

FIG. 20 shows the correlation between the trained exemplary IFN type II Bayesian network model using the evidence curated list of target genes (23 target genes list) from Table 1 and the 9 target gene shortlist from Table 2, respectively. In the diagram, the horizontal axis indicates the odds (on a log 2 scale) that the TF element is "present" resp. "absent", which corresponds to the JAK-STAT1/2 cellular signaling pathway being active resp. passive, as predicted by the trained exemplary IFN type II Bayesian network model using the evidence curated list of target genes (23 target genes list) from Table 1. The vertical axis indicates the same information, as predicted by the trained exemplary IFN type I Bayesian network model using the 9 target gene shortlist from Table 2 (data sets GSE58096, GSE11327, GSE11864). The two models are significantly correlated with a p-value of 2.2e-16 and a correlation coefficient of 0.992.

Figure 21:
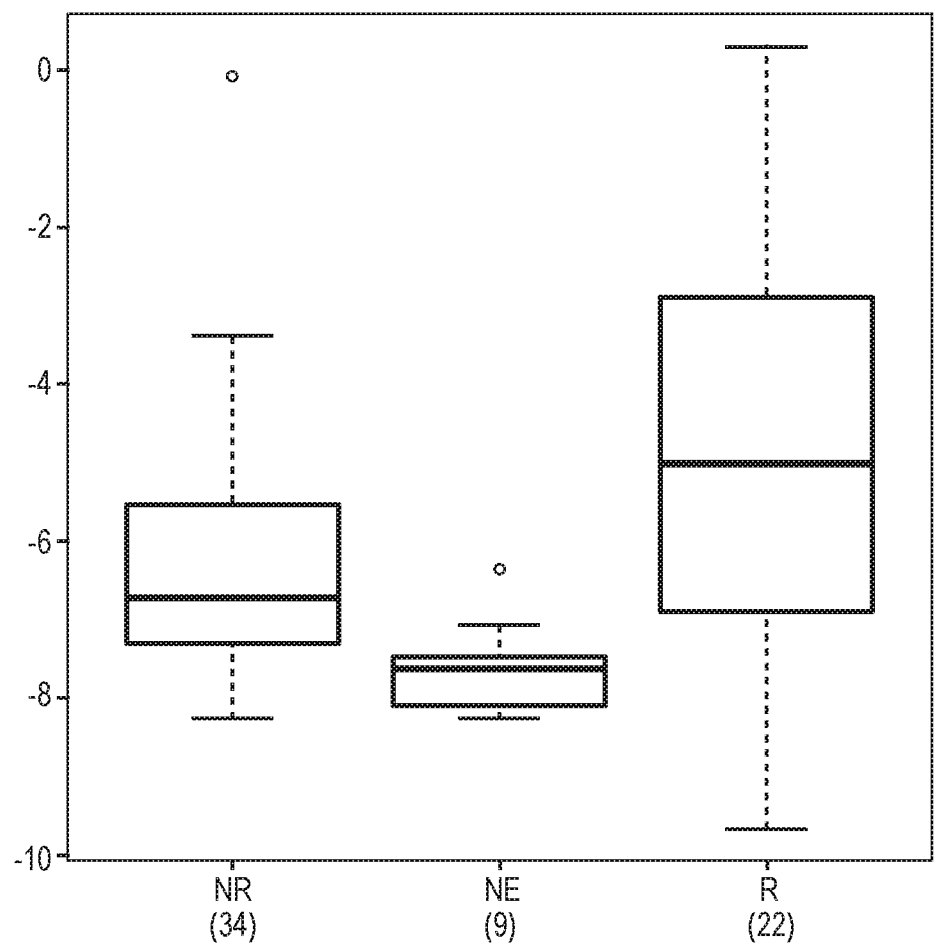
FIG. 21 shows further validation results of the trained exemplary Bayesian network model using the evidence curated list of target genes (23 target genes list) from Table 1.

Further validation results of the trained exemplary Bayesian network model using the evidence curated list of target genes (23 target genes list) from Table 1 are shown in FIG. 21. The diagram shows the results of a clinical study, in which patients with metastatic melanoma were treated with MAGE-A3 immunotherapy (six or more doses of the immunotherapeutic), and responders and non-responders were identified. From the 65 samples that were included in the study, 9 samples were not evaluable (NE), 22 samples were responders (R), and 34 samples were non-responders (NR). In the diagram, the each box represents the distribution of the STAT1/2 pathway activity score for each group (NR, R, NR). It shows that the group of responders (R) has a significantly higher STAT1/2 pathway score compared to the non-responders (NR). The group that was not evaluable (NE) has an even lower STAT1/2 pathway score.

Instead of applying the mathematical model, e.g., the exemplary Bayesian network model, on mRNA input data coming from microarrays or RNA sequencing, it may be beneficial in clinical applications to develop dedicated assays to perform the sample measurements, for instance on an integrated platform using qPCR to determine mRNA levels of target genes. The RNA/DNA sequences of the disclosed target genes can then be used to determine which primers and probes to select on such a platform.

Validation of such a dedicated assay can be done by using the microarray-based mathematical model as a reference model, and verifying whether the developed assay gives similar results on a set of validation samples. Next to a dedicated assay, this can also be done to build and calibrate similar mathematical models using RNA sequencing data as input measurements.

The set of target genes which are found to best indicate specific cellular signaling pathway activity, e.g., Tables 1 and 2, based on microarray/RNA sequencing based investigation using the mathematical model, e.g., the exemplary Bayesian network model, can be translated into a multiplex quantitative PCR assay to be performed on a sample and/or a computer to interpret the expression measurements and/or to infer the activity of the JAK-STAT1/2 cellular signaling pathway. To develop such a test (e.g., FDA-approved or a CLIA waived test in a central service lab or a laboratory developed test for research use only) for cellular signaling pathway activity, development of a standardized test kit is required, which needs to be clinically validated in clinical trials to obtain regulatory approval.

The present invention relates to a method comprising determining an activity level of a JAK-STAT1/2 cellular signaling pathway in a subject based at least on expression levels of at least three, for example, at least four, at least five, at least six, at least seven, at least eight, at least nine, at least ten or more target genes of the JAK-STAT1/2 cellular signaling pathway measured in a sample. The present invention further relates to an apparatus comprising a digital processor configured to perform such a method, a non-transitory storage medium storing instructions that are executable by a digital processing device to perform such a method, and a computer program comprising program code means for causing a digital processing device to perform such a method.

The method may be used, for instance, in diagnosing an (abnormal) activity of the JAK-STAT1/2 cellular signaling pathway, in prognosis based on the determined activity level of the JAK-STAT1/2 cellular signaling pathway, in the enrollment in a clinical trial based on the determined activity level of the JAK-STAT1/2 cellular signaling pathway, in the selection of subsequent test(s) to be performed, in the selection of companion diagnostics tests, in clinical decision support systems, or the like. In this regard, reference is made to the published international patent application WO 2013/011479 A2 ("Assessment of cellular signaling pathway activity using probabilistic modeling of target gene expression"), to the published international patent application WO 2014/102668 A2 ("Assessment of cellular signaling pathway activity using linear combination(s) of target gene expressions"), and to Verhaegh W. et al., "Selection of personalized patient therapy through the use of knowledge-based computational models that identify tumor-driving signal transduction pathways", Cancer Research, Vol. 74, No. 11, 2014, pages 2936-2945, which describe these applications in more detail.

This specification has been described with reference to embodiments, which are illustrated by the accompanying Examples. The invention can, however, be embodied in different forms and should not be construed as limited to the embodiments set forth herein. Given the teaching herein, one of ordinary skill in the art will be able to modify the invention for a desired purpose and such variations are considered within the scope of the disclosure.

| Sequence Listing: | |
|---|---|
| Seq. No. | Gene: |
| Seq. 1 | BID |
| Seq. 2 | GNAZ |
| Seq. 3 | IRF1 |
| Seq. 4 | IRF7 |
| Seq. 5 | IRF8 |
| Seq. 6 | IRF9 |
| Seq. 7 | LGALS1 |
| Seq. 8 | NCF4 |
| Seq. 9 | NFAM1 |
| Seq. 10 | OAS1 |
| Seq. 11 | PDCD1 |
| Seq. 12 | RAB36 |
| Seq. 13 | RBX1 |
| Seq. 14 | RFPL3 |
| Seq. 15 | SAMM50 |
| Seq. 16 | SMARCB1 |
| Seq. 17 | SSTR3 |
| Seq. 18 | ST13 |
| Seq. 19 | STAT1 |
| Seq. 20 | TRMT1 |
| Seq. 21 | UFD1L |
| Seq. 22 | USP18 |
| Seq. 23 | ZNRF3 |

The invention claimed is:

1. A method of treating a subject suffering from a disease associated with an activated JAK-STAT1/2 cellular signaling pathway, comprising:
   a. receiving information regarding the activity level of a JAK-STAT1/2 cellular signaling pathway derived from a sample isolated from the subject, wherein the activity level of the JAK-STAT1/2 cellular signaling pathway is determined by:
      i. calculating an activity level of a JAK-STAT1/2 transcription factor element in a sample isolated from the subject, wherein the activity level of the JAK-STAT1/2 transcription factor element in the sample is associated with JAK-STAT1/2 cellular signaling, and wherein the activity level of the JAK-STAT1/2 transcription factor element in the sample is calculated by:
         1. receiving data on the expression levels of at least three target genes derived from the sample, wherein the JAK-STAT1/2 transcription factor element controls transcription of the at least three target genes, and wherein the at least three target genes are selected from BID, GNAZ, IRF1, IRF7, IRF8, IRF9, LGALS1, NCF4, NFAM1, OAS1, PDCD1, RAB36, RBX1, RFPL3, SAMM50, SMARCB1, SSTR3, ST13, STAT1, TRMT1, UFD1L, USP18, and ZNRF3;
         2. calculating the activity level of the JAK-STAT1/2 transcription factor element in the sample using a calibrated pathway model, wherein the calibrated pathway model compares the expression levels of the at least three target genes in the sample with expression levels of the at least three target genes in the calibrated pathway model which define an activity level of JAK-STAT1/2 transcription factor element;
      ii. calculating the activity level of the JAK-STAT1/2 cellular signaling pathway in the sample based on the calculated activity level of the JAK-STAT1/2 transcription factor element in the sample; and
   b. determining that the JAK-STAT1/2 cellular signaling pathway is operating abnormally in the subject based on the calculated activity level of the JAK-STAT1/2 cellular signaling pathway in the sample; and
   c. administering to the subject a JAK-STAT1/2 inhibitor when the information regarding the activity level of the JAK-STAT1/2 cellular signaling pathway is indicative of an abnormal JAK-STAT1/2 cellular signaling pathway;
   wherein the activity level of the JAK-STAT1/2 cellular signaling pathway is determined to be either IFN type I activity or IFN type II activity by using two calibrated pathway models of which one is calibrated on IFN type I activity and the other is calibrated on IFN type II activity.

2. The method of claim 1, further comprising assigning a JAK-STAT1/2 cellular signaling pathway activity status to the calculated activity level of the JAK-STAT1/2 cellular signaling pathway in the sample, wherein the activity status is indicative of either an active JAK-STAT1/2 cellular signaling pathway or a passive JAK-STAT1/2 cellular signaling pathway.

3. The method of claim 2, further comprising displaying the JAK-STAT1/2 cellular signaling pathway activity status.

4. The method of claim 1, wherein the calibrated pathway model is a probabilistic model incorporating conditional probabilistic relationships that compare the expression levels of the at least three target genes in the sample with expression levels of the at least three target genes in the calibrated pathway model which define a level of the JAK-STAT1/2 transcription factor element to determine the activity level of JAK-STAT1/2 transcription factor element in the sample.

5. The method of claim 1, wherein the calibrated pathway model is a linear model incorporating relationships that compare the expression levels of the at least three target genes in the sample with expression levels of the at least three target genes in the calibrated pathway model which define a level of the JAK-STAT1/2 transcription factor element to determine the activity level of the JAK-STAT1/2 transcription factor element in the sample.

6. The method of claim 1, wherein the at least three target genes comprise at least six target genes selected from IRF1, IRF7, IRF8, IRF9, OAS1, PDCD1, ST13, STAT1, and USP18.

7. The method of claim 1, wherein the JAK-STAT1/2 inhibitor is Ruxolitinib, Tofacitinib, Oclacitinib, Baricitinib, Filgotinib, Gandotinib, Lestaurtinib, Momelotinib, Pacritinib, or Fedratinib.

8. The method of claim 1, wherein the disease is a cancer or an immune disorder.

* * * * *